United States Patent
Boitano et al.

(10) Patent No.: US 12,403,185 B2
(45) Date of Patent: *Sep. 2, 2025

(54) USE OF ANTI-CD137 ANTIBODY DRUG CONJUGATE (ADC) IN ALLOGENEIC CELL THERAPY

(71) Applicant: Heidelberg Pharma Research GmbH, Ladenburg (DE)

(72) Inventors: Anthony Boitano, Newton, MA (US); Michael Cooke, Boston, MA (US)

(73) Assignee: Heidelberg Pharma Research GmbH, Ladenburg (DE)

( * ) Notice: Subject to any disclaimer, the term of this patent is extended or adjusted under 35 U.S.C. 154(b) by 1024 days.

This patent is subject to a terminal disclaimer.

(21) Appl. No.: 17/155,936

(22) Filed: Jan. 22, 2021

(65) Prior Publication Data

US 2021/0228696 A1   Jul. 29, 2021

Related U.S. Application Data

(63) Continuation of application No. PCT/US2019/043119, filed on Jul. 23, 2019.

(60) Provisional application No. 62/702,292, filed on Jul. 23, 2018.

(51) Int. Cl.
| | |
|---|---|
| *A61K 39/00* | (2006.01) |
| *A61K 38/07* | (2006.01) |
| *A61K 38/12* | (2006.01) |
| *A61K 40/11* | (2025.01) |
| *A61K 40/31* | (2025.01) |
| *A61K 40/41* | (2025.01) |
| *A61K 40/50* | (2025.01) |
| *A61K 47/64* | (2017.01) |
| *A61K 47/65* | (2017.01) |
| *A61K 47/68* | (2017.01) |
| *A61P 37/06* | (2006.01) |

(52) U.S. Cl.
CPC ........... *A61K 39/001* (2013.01); *A61K 38/07* (2013.01); *A61K 38/12* (2013.01); *A61K 40/11* (2025.01); *A61K 40/31* (2025.01); *A61K 40/418* (2025.01); *A61K 47/6415* (2017.08); *A61K 47/65* (2017.08); *A61K 47/6831* (2017.08); *A61K 47/6849* (2017.08); *A61P 37/06* (2018.01); *A61K 40/50* (2025.01); *A61K 2239/31* (2023.05); *A61K 2239/38* (2023.05)

(58) Field of Classification Search
CPC ...... A61K 39/001; A61K 35/17; A61K 38/07; A61K 38/12; A61K 47/6415; A61K 47/65; A61K 47/6831; A61K 47/6849; A61K 39/4631; A61K 39/46434; A61K 2239/26; A61K 2239/31; A61K 39/4611; A61K 2239/38; A61K 47/6889; A61K 2300/00; A61K 39/46431; A61P 37/06; A61P 35/00; C07K 2317/77; C07K 16/2878

See application file for complete search history.

(56) References Cited

U.S. PATENT DOCUMENTS

| | | | |
|---|---|---|---|
| 10,875,926 B2 | 12/2020 | Xu et al. | |
| 2011/0177104 A1 | 7/2011 | Kwon et al. | |
| 2017/0216356 A1 | 8/2017 | Eshhar et al. | |
| 2017/0360954 A1 | 12/2017 | Nixon et al. | |
| 2021/0077530 A1* | 3/2021 | Mamonkin | ........ A61K 39/4611 |

FOREIGN PATENT DOCUMENTS

| | | | |
|---|---|---|---|
| EP | 0 239 400 | 8/1994 | |
| EP | 0 425 235 | 9/1996 | |
| EP | 0 349 578 | 10/1998 | |
| EP | 0 527 839 | 12/1998 | |
| EP | 0 592 106 | 11/2004 | |
| EP | 0 519 596 | 2/2005 | |
| EP | 0 589 877 | 10/2005 | |
| KR | 100500283 B1 * | 7/2005 | ............ C07K 16/18 |
| WO | 91/09967 | 7/1991 | |
| WO | 1996/029348 | 9/1996 | |
| WO | 98/13059 | 4/1998 | |
| WO | 02/088172 | 11/2002 | |
| WO | 2004/010947 | 2/2004 | |
| WO | 2004/032828 | 4/2004 | |
| WO | 2005/035584 | 4/2005 | |
| WO | 2005/037992 | 4/2005 | |
| WO | 2005/081711 | 9/2005 | |
| WO | 2006/034488 | 3/2006 | |
| WO | 2006/126835 | 11/2006 | |
| WO | 2010/132389 | 11/2010 | |
| WO | 2011/031063 | 3/2011 | |

(Continued)

OTHER PUBLICATIONS

Mo F et al. Engineered off-the-shelf therapeutic T cells resist host immune rejection (Nat Biotechnol. Jan. 2021; 39(1): 56-63) (Year: 2021).*

(Continued)

*Primary Examiner* — Karen A. Canella
*Assistant Examiner* — John J Skoko, III
(74) *Attorney, Agent, or Firm* — Grüneberg and Myers PLLC

(57) ABSTRACT

The invention provides methods of using allogeneic cells in therapy by combining allogeneic cell therapy with anti-CD137 antibody drug conjugates (ADCs). Disclosed are methods of treating or preventing a host versus graft (HvG) rejection in a human subject receiving allogeneic cell therapy by administering to the human subject an anti-CD137 ADC.

23 Claims, 6 Drawing Sheets
Specification includes a Sequence Listing.

(56) References Cited

FOREIGN PATENT DOCUMENTS

| | | | |
|---|---|---|---|
| WO | 2012/032433 | 3/2012 | |
| WO | 2012/145183 | 10/2012 | |
| WO | 2014/055771 | 4/2014 | |
| WO | WO-2015077615 A1 * | 5/2015 | ............ A61K 35/17 |
| WO | 2015/119923 | 8/2015 | |
| WO | 2015/179236 | 11/2015 | |
| WO | 2015/188047 | 12/2015 | |
| WO | 2016/029073 | 2/2016 | |
| WO | 2016/110584 | 7/2016 | |
| WO | 2016/134358 | 8/2016 | |
| WO | WO-2016142049 A1 * | 9/2016 | ............ A61K 38/12 |
| WO | 2017/049452 | 3/2017 | |
| WO | 2017/077085 | 5/2017 | |
| WO | 2017/130076 | 8/2017 | |
| WO | 2017/149077 | 9/2017 | |
| WO | 2017/181034 | 10/2017 | |
| WO | 2018/017761 | 1/2018 | |
| WO | 2018/091740 | 5/2018 | |
| WO | 2018/098370 | 5/2018 | |
| WO | 2018/116178 | 6/2018 | |
| WO | 2018/127787 | 7/2018 | |
| WO | 2018/134787 | 7/2018 | |
| WO | 2018/156740 | 8/2018 | |
| WO | 2018/191502 | 10/2018 | |
| WO | 2019/014328 | 1/2019 | |
| WO | 2019/020774 | 1/2019 | |
| WO | 2019/027754 | 2/2019 | |
| WO | 2019/036855 | 2/2019 | |
| WO | 2019/037711 | 2/2019 | |
| WO | 2019/105468 | 6/2019 | |

OTHER PUBLICATIONS

Wang Y et al. Development and Properties of Valine-Alanine based Antibody-Drug Conjugates with Monomethyl Auristatin E as the Potent Payload (Int J Mol Sci. Sep. 2017; 18(9): 1860.) (Year: 2017).*

Shimabukuro-Vornhagen A et al. Cytokine release syndrome (Journal for ImmunoTherapy of Cancer vol. 2018 6, 56 1-14). (Year: 2018).*

Palfi A et al. CD19—a potential target for Amanitin-based ADCs (AACR 2017 poster, uploaded Mar. 31, 2017) (Year: 2017).*

Pahl A et al. Amanitins and their development as a payload for antibody-drug conjugates (Drug Discovery Today: Technologies 2018 30, 85-89) (Year: 2018).*

KR 100500283B1 (Kim JY et al.) English translation provided by Google Patents. (Year: 2024).*

Maude SL et al. Chimeric Antigen Receptor T Cells for Sustained Remissions in Leukemia. N Engl J Med. 2014 371(16):1507-1517. (Year: 2014).*

Qasim W et al. Molecular remission of infant B-ALL after infusion of universal TALEN gene-edited CAR T cells. (Sci. Transl. Med. 2017 9, eaaj2013 1-8) (Year: 2017).*

Turtle CJ et al. Anti-CD19 Chimeric Antigen Receptor-Modified T Cell Therapy for B Cell Non-Hodgkin Lymphoma and Chronic Lymphocytic Leukemia: Fludarabine and Cyclophosphamide Lymphodepletion Improves In Vivo Expansion and Persistence of CAR-T Cells and Clinical Outcomes. (Blood 2015 126 (23): 184) (Year: 2015).*

Antonow et al., "Synthesis of DNA-interactive Pyrrolo[2,1-c][1,4]benzodiazepines (PBDs)", Chem Rev., vol. 111, Dec. 17, 2010, pp. 2815-2864.

Barbas III et al., "Assembly of combinatorial antibody libraries on phage surfaces: The gene III site", Proc. Natl. Acad. Sci. USA, vol. 88, Sep. 1991, pp. 7978-7982.

Bird et al., "Single-Chain Antigen-Binding Proteins", Science, vol. 242, Oct. 21, 1988, pp. 423-426.

Bradley A. Katz, "Structural and Mechanistic Determinants of Affinity and Specificity of Ligands Discovered or Engineered by Phage Display", Annu. Rev. Biophys. Biomol. Struct., vol. 26, 1997, pp. 27-45.

Brian K. Kay, "Biologically displayed random peptides as reagents in mapping protein-protein interactions", Perspectives in Drug Discovery and Design, vol. 2, Mar. 9, 1995, pp. 251-268.

Cannons et al., "4-1BB Ligand Induces Cell Division, Sustains Survival, and Enhances Effector Function of CD4 and CD8 T Cells with Similar Efficacy", The Journal of Immunology, vol. 167, May 29, 2001, pp. 1313-1324.

Carl et al., "A Novel Connector Linkage Applicable in Prodrug Design", Journal of Medicinal Chemistry, vol. 24, No. 5, May 1981, pp. 479-480.

Chakravarty et al., "Plasmin-Activated Prodrugs for Cancer Chemotherapy.2. Synthesis and Biological Activity of Peptidyl Derivatives of Doxorubicin", J. Med. Chem., vol. 26, No. 5, 1983, pp. 638-644.

Chari et al., "Immunoconjugates Containing Novel Maytansinoids: Promising Anticancer Drugs", Cancer Research, vol. 52, Jan. 1, 1992, pp. 127-131.

Chin et al., "Structure of the 4-1BB/4-1BBL complex and distinct binding and functional properties of utomilumab and urelumab", Nature communications, vol. 9, No. 4679, Nov. 8, 2018, pp. 1-13.

Chiswell et al., "Phage antibodies: will new 'coliclonal' antibodies replace monoclonal antibodies?", Trends Biotechnol., vol. 10, Mar. 1992, pp. 80-84.

Clackson et al., "Making antibody fragments using phage display libraries", Nature, vol. 352, Aug. 15, 1991, pp. 624-628.

De Groot et al., "Elongated Multiple Electronic Cascade and Cyclization Spacer Systems in Activatible Anticancer Prodrugs for Enhanced Drug Release", J. Org. Chem., vol. 66, No. 26, Jul. 3, 2001, pp. 8815-8830.

Doronina et al., "Development of potent monoclonal antibody auristatin conjugates for cancer therapy", Nature Biotechnology, vol. 21, No. 7, Jul. 2003, pp. 778-784.

Doronina et al., "Enhanced Activity of Monomethylauristatin F through Monoclonal Antibody Delivery: Effects of Linker Technology on Efficacy and Toxicity", Bioconjugate Chem., vol. 17, No. 1, 2006, pp. 114-124.

Dubowchik et al., "Receptor-mediated and enzyme-dependent targeting of cytotoxic anticancer drugs", Pharmacology & Therapeutics, vol. 83, 1999, pp. 67-123.

Dubrot et al., "Treatment with anti-CD137 mAbs causes intense accumulations of liver T cells without selective antitumor immunotherapeutic effects in this organ" Cancer Immunol. Immunother., vol. 59, Mar. 25, 2010, pp. 1223-1233.

Eduardo A. Padlan, "A possible procedure for reducing the immunogenicity of antibody variable domains while preserving their ligand-binding properties", Molecular Immunology, vol. 28, No. 4/5, Sep. 17, 1990, pp. 489-498.

European Search Report received for European Patent Application No. 19842193.5, mailed on Jun. 3, 2022, 5 pages.

Felici et al., "Peptide and protein display on the surface of filamentous Bacteriophage", Biotechnology Annual Review, vol. 1, 1995, pp. 149-183.

Fisher et al., "Targeting of 4-1BB by monoclonal antibody PF-05082566 enhances T-cell function and promotes anti-tumor activity", Cancer Immunol. Immunother., vol. 61, Mar. 11, 2012, pp. 1721-1733.

Geyer et al., "Review: Current clinical applications of chimeric antigen receptor (CAR) modified T cells", *Cytotherapy*, vol. 18, Jul. 15, 2016, pp. 1393-1409.

Ghosh et al., "Donor CD19 CAR T cells exert potent graft-versus-lymphoma activity with diminished graft-versus-host activity", Nature Medicine, vol. 23, No. 2, Feb. 2017, pp. 242-249.

Gillies et al., "High-level expression of chimeric antibodies using adapted cDNA variable region cassettes", Journal of Immunological Methods, vol. 125, Aug. 30, 1989, pp. 191-202.

Greg T. Hermanson, "Bioconjugate Techniques" Second Edition, Academic Press: New York, Homobifunctional Crosslinkers, pp. 234-242.

Graham et al., "Characterisitcs of a Human Cell Line Transformed by DNA from Human Adenovirus Type 5", J. Gen Virol. vol. 36, Feb. 10, 1977, pp. 59-72.

Guedan et al., "Engineering and Design of Chimeric Antigen Receptors", *Molecular Therapy—Methods & Clinical Development*, vol. 12, Mar. 2019, pp. 145-156.

(56) References Cited

OTHER PUBLICATIONS

Hay et al., "A 2-Nitroimidazole Carbamate Prodrug of 5-Amino-1-(Chloromethyl)-3-[(5,6,7-Trimethoxyindol-2-yl)Carbonyl]-1,2-Dihydro-3H-Benz[E]Indole (Amino-Seco-CBI-TMI) For Use With Adept and Gdept", Bioorg. Med. Chem. Lett., vol. 9, Jun. 25, 1999, pp. 2237-2242.
Hinman et al., "Preparation and Characterization of Monoclonal Antibody Conjugates of the Calicheamicins: A Novel and Potent Family of Antitumor Antibiotics", Cancer Research, vol. 53, Jul. 15, 1993, pp. 3336-3342.
Hoogenboom et al., "Antibody phage display technology and its applications", Immunotechnology, vol. 4, Feb. 13, 1998, pp. 1-20.
Huston et al., "Protein engineering of antibody binding sites: Recovery of specific Activity in an anti-digoxin single-chain Fv analogue produced in *Escherichia coli*", Proc. Natl. Acad. Sci. USA, vol. 85, Aug. 1988, pp. 5879-5883.
International Search Report received for PCT Application No. PCT/US2019/043119, mailed on Oct. 16, 2019, 4 pages.
Jain et al., "Current ADC Linker Chemistry", Pharm. Res., vol. 32, Mar. 11, 2015, pp. 3526-3540.
Jennie P. Mather, "Establishment and Characterization of Two Distinct Mouse Testicular Epithelial Cell Lines", Biology of Reproduction, vol. 23, Apr. 29, 1980, pp. 243-252.
John A Hartley, "The development of pyrrolobenzodiazapines as antitumor agents", Expert Opinion on Investigational Drugs, vol. 20, No. 6, Apr. 4, 2011, pp. 733-744.
Kay et al., "High-throughput screening strategies to identify inhibitors of protein-protein interactions", Molecular Diversity, vol. 1, 1995, pp. 139-140.
Keith A. Charlton, "Expression and Isolation of Recombinant Antibody Fragments in *E. coli*", Antibody Engineering Methods and Protocols, Methods in Molecular Biology™, (Benny K. C. Lo, ed., Humana Press, Totowa, N.J.), vol. 248, 2004, pp. 245-254.
Laguzza et al., "New Antitumor Monoclonal Antibody-Vinca Conjugates LY203725 and Related Compounds: Design, Preparation, and Representative in Vivo Activity", J. Med. Chem., vol. 32, No. 3, 1989, pp. 548-555.
Lee et al., "Depletion of Alloreactive T-Cells by Anti-CD137-Saporin Immunotoxin", Cell Transplantation, vol. 24, No. 6, Jun. 1, 2015, pp. 1167-1181.
Lee et al., "Molecular cloning of agonistic and antagonistic monoclonal antibodies against human 4-1 BB", European Journal of Immunogenetics, vol. 29, Jul. 11, 2002, pp. 449-452.
Leriche et al., "Cleavable linkers in checmical biology", Bioorganic & Medicinal Chemistry, vol. 20, 2012, pp. 571-582.
Liu et al., "New Procedures for Preparation and Isolation of Conjugates Proteins and a Synthetic Copolymer of D-Amino Acids and Immunochemical Characterization of Such Conjugates", Biochemistry, vol. 18, No. 4, 1979, pp. 690-697.
Lode et al., "Targeted Therapy with a Novel Enediyene Antibiotic Calicheamicin $\theta^1_1$, Effectively Suppresses Growth and Dissemination of Liver Metastases in a Syngeneic Model of Murine Neuroblastoma", Cancer Research, vol. 58, Jul. 15, 1998, pp. 2925-2928.
Makkouk et al., "Characterizing CD137 upregulation on NK cells in patients receiving monoclonal antibody therapy", Annals of Oncology, vol. 28, Issue 2, 2017, pp. 415-420.
Mantaj et al., "From Anthramycin to Pyrrolobenzodiazepine (PBD)—Containing Antibody—Drug Conjugates (ADCs)", Angewandte Chemie International Edition, vol. 56, 2017, pp. 462-488.
Martinez-Forero et al., "T Cell Constimulation with Anti-CD137 Monoclonal Antibodies Is Mediated by K63-Polyubiquitin-Dependent Signals from Endosomes", J. Immunol., vol. 190, No. 12, Jun. 15, 2013, pp. 6694-6706.
Mather et al., "Culture of Testicular Cells in Hormone-Supplemented Serum-Free Medium", Annals N.Y. Acad. Sci., vol. 383, 1982, pp. 44-68.
Matinkhoo et al., "Synthesis of the Death-Cap Mushroom Toxin α-Amanitin" J. Am. Chem. Soc., vol. 140, Mar. 21, 2018, pp. 6513-6517.

McCafferty et al., "Phage antibodies: filamentous phage displaying antibody variable domains", Nature, vol. 348, Dec. 6, 1990. pp. 552-554.
Neville, Jr. et al., "Enhancement of Immunotoxin Efficacy by Acid-cleavable Cross-linking Agents Utilizing Diphtheria Toxin and Toxin Mutants", The Journal of Biological Chemistry, vol. 264, No. 25, Mar. 30, 1989, pp. 14653-14661.
Nicholson et al., "Construction and Characterisation of a Functional Cd19 Specific Single Chain Fv Fragment for Immunotherapy of B Lineage Leukaemia and Lymphoma" Molecular Immunology, vol. 34, No. 16-17, Nov. 7, 1997, pp. 1157-1165.
N. R. Bachur, "Free Radical Damage", Anthracycline Antibiotics in Cancer Therapy, 1982, pp. 97-102.
Peterson et al., "Transport and Storage of Anthracycline in Experimental Systems and Human Leukemia" in *Anthracycline Antibiotics in Cancer Therapy*, Sep. 16-18, 1981, pp. 132-146.
Pettit et al., The Absolute Configuration and Synthesis of Natural (−)-Dolastatin $10^1$, J. Am. Chem. Soc., vol. 111, No. 14, 1989, pp. 5463-5465.
Pettit et al., "Dolastatins 24. Synthesis of (−)-dolastatin $10.^1$ X-Ray molecular structure of N,N-dimethylvalyl-dolaisoleuine tert-butyl ester", J. Chem. Soc. Perkin Trans., vol. 1, 1996, pp. 859-863.
Pettit et al., "Antineoplastic agents 365. Dolastatin 10 SAR probes", Anti-Cancer Drug Design, vol. 13, Sep. 3, 1997, pp. 243-277.
Pettit et al., "Specific Activities of Dolastatin 10 and Peptide Derivatives against *Cryptococcus neoformans*", Antimicrobial Agents and Chemotherapy, vol. 42, No. 11, Nov. 1998, pp. 2961-2965.
Pettit et al., "The Dolastatins; 18: Stereospecific Synthesis of Dolaproine", Synthesis, Jun. 1996, pp. 719-725.
Quintieri et al., "Formation and Antitumor Activity of PNU-159682, A Major Metabolite of Nemorubicin in Human Liver Microsomes", Clinical Cancer Research, vol. 11, Feb. 15, 2005, pp. 1608-1617.
Riechmann et al., "Reshaping human antibodies for therapy", Nature, vol. 332, Mar. 24, 1988, pp. 323-327.
Roguska et al., "Humanization of murine monolclonal antibodies through variable Domain resurfacing", Proc. Natl. Acad. Sci. USA, vol. 91, Feb. 1994, pp. 696-973.
Sadelain et al., "The Basic Principles of Chimeric Antigen Receptor Design", Cancer discovery, vol. 3, No. 4, Apr. 2013, pp. 388-398.
Segal et al., "Results from an Integrated Safety Analysis of Urelumab, an Agonist Anti-CD137 Monoclonal Antibody", Clinical Cancer Research, vol. 23, No. 8, Apr. 15, 2017, pp. 1929-1936.
Segal et al., "Phase I Study of Single-Agent Utomilumab (PF-05082566), a 4-1BB/CD137 Agonist, in Patients with Advanced Cancer", Clinical Cancer Research, vol. 24, No. 8, Apr. 15, 2018, pp. 1816-1823.
Sessa et al., "Ongoing phase I and II studies of novel anthracyclines", Cardiovasc Toxicol, vol. 7, May 22, 2007, pp. 75-79.
Sherrie L. Morrison, "Transfectomas Provide Novel Chimeric Antibodies", Science, vol. 229, Sep. 20, 1985, pp. 1202-1207.
Söderström et al., "Increased Carotid Artery Lesion Inflammation Upon Treatment With the CD137 Agonistic Antibody 2A", Circ. J., vol. 81, Dec. 2017, pp. 1945-1952.
Studnicka et al., "Human-engineered monoclonal antibodies retain full specific binding activity by preserving non-CDR complementarity-modulating residues", 1994, Protein Engineering, vol. 7, No. 6, Mar. 23, 1994, pp. 805-814.
Sutherland et al., "SGN-CD33A: a novel CD33-targeting antibody—drug conjugate using a pyrrolobenzodiazepine dimer is active in models of drug-resistant AML", Blood, vol. 122, No. 8, Aug. 22, 2013, pp. 1455-1463.
Theodor Wieland, "The toxic peptides from Amanita mushrooms", Int. J. Peptide Protein Res. vol. 22, Jan. 15, 1983, pp. 257-276.
Thorpe et al., "New Coupling Agents for the Synthesis of Immunotoxins Containing a Hindered Disulfide Bond with Improved Stability in Vivo", Cancer Research, vol. 47, Nov. 15, 1987, pp. 5924-5931.
Tiberghien et al., "Design and Synthesis of Tesirine, a Clinical Antibody—Drug Conjugate Pyrrolobenzodiazepine Dimer Payload", ACS Med. Chem. Lett., vol. 7, May 24, 2016, pp. 983-987.
Urlaub et al., "Isolation of Chinese hamster cell mutants deficient in dihydrofolate Reductase activity", Proc. Natl. Acad. Sci. USA, vol. 77, No. 7, Jul. 1980, pp. 4216-4220.

(56) References Cited

OTHER PUBLICATIONS

Ward et al., "Binding activities of a repertoire of single immunoglobulin variable domains secreted from *Escherichia coli*", Nature, vol. 341, Oct. 12, 1989, pp. 544-546.

Williams et al., "Cell-based selection of internalizing fully human antagonistic antibodies directed against FLT3 for suppression of leukemia cell growth", Leukemia, vol. 19, Jun. 2, 2005, pp. 1432-1438.

Woyke et al., "In Vitro Activities and Postantifungal Effects of the Potent Dolastatin 10 Derivative Auristatin PHE", Antimicrobial Agents And Chemotherapy, vol. 45, No. 12, Dec. 2001, pp. 3580-3584.

Yazaki et al., "Expressions of Recombinant Antibodies in Mammalian Cell lines", Antibody Engineering Methods and Protocols, Methods in Molecular Biology, vol. 248, 2004, pp. 255-268.

Zanotti et al., "Synthesis of analogues of amaninamide, an amatoxin from the white Amanita virosa mushroom", Int. J. Peptide Protein Res., vol. 30, Jan. 30, 1987, pp. 450-459.

H. Raedler, et al., "Primed CD8+ T-Cell Responses to Allogeneic Endothelial Cells Are Controlled by Local Complement Activation, American Journal of Transplantation and the American Society of Transplant Surgeons", 2009, pp. 1784-1795.

\* cited by examiner

SEQUENCE LISTING

```
<160> NUMBER OF SEQ ID NOS: 28

<210> SEQ ID NO 1
<211> LENGTH: 255
<212> TYPE: PRT
<213> ORGANISM: Homo sapiens

<400> SEQUENCE: 1

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu
                245                 250                 255

<210> SEQ ID NO 2
<211> LENGTH: 46
<212> TYPE: PRT
<213> ORGANISM: Homo sapiens

<400> SEQUENCE: 2

Ala Lys Pro Thr Thr Thr Pro Ala Pro Arg Pro Pro Thr Pro Ala Pro
```

```
                1               5                  10                  15
Thr Ile Ala Ser Gln Pro Leu Ser Leu Arg Pro Glu Ala Cys Arg Pro
                20                  25                  30

Ala Ala Gly Gly Ala Val His Thr Arg Gly Leu Asp Phe Ala
                35                  40                  45

<210> SEQ ID NO 3
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
                20                  25                  30

Ala Ala Gly Gly Ala Val His Thr Arg Gly Leu Asp Phe Ala Pro Arg
                35                  40                  45

Lys Ile Glu Val Met Tyr Pro Pro Tyr Leu Asp Asn Glu Lys Ser
50                  55                  60

Asn Gly Thr Ile Ile His Val Lys Gly Lys His Leu Cys Pro Ser Pro
65                  70                  75                  80

Leu Phe Pro Gly Pro Ser Lys Pro
                85

<210> SEQ ID NO 4
<211> LENGTH: 28
<212> TYPE: PRT
<213> ORGANISM: Homo sapiens

<400> SEQUENCE: 4

Leu Asp Pro Lys Leu Cys Tyr Leu Leu Asp Gly Ile Leu Phe Ile Tyr
1               5                   10                  15

Gly Val Ile Leu Thr Ala Leu Phe Leu Arg Val Lys
                20                  25

<210> SEQ ID NO 5
<211> LENGTH: 21
<212> TYPE: PRT
<213> ORGANISM: Homo sapiens

<400> SEQUENCE: 5

Leu Cys Tyr Leu Leu Asp Gly Ile Leu Phe Ile Tyr Gly Val Ile Leu
1               5                   10                  15

Thr Ala Leu Phe Leu
                20

<210> SEQ ID NO 6
<211> LENGTH: 27
<212> TYPE: PRT
<213> ORGANISM: Homo sapiens

<400> SEQUENCE: 6

Phe Trp Val Leu Val Val Val Gly Gly Val Leu Ala Cys Tyr Ser Leu
1               5                   10                  15

Leu Val Thr Val Ala Phe Ile Ile Phe Trp Val
                20                  25
```

<210> SEQ ID NO 7
<211> LENGTH: 66
<212> TYPE: PRT
<213> ORGANISM: Homo sapiens

<400> SEQUENCE: 7

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65

<210> SEQ ID NO 8
<211> LENGTH: 112
<212> TYPE: PRT
<213> ORGANISM: Homo sapiens

<400> SEQUENCE: 8

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 9
<211> LENGTH: 42
<212> TYPE: PRT
<213> ORGANISM: Homo sapiens

<400> SEQUENCE: 9

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 10
<211> LENGTH: 41
<212> TYPE: PRT
<213> ORGANISM: Homo sapiens

<400> SEQUENCE: 10

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40

<210> SEQ ID NO 11
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
                20                  25                  30

Trp Ile Asn Trp Val Lys Gln Arg Pro Gly Gln Gly Leu Glu Trp Ile
            35                  40                  45

Gly Asn Ile Tyr Pro Ser Asp Ser Tyr Thr Asn Tyr Asn Gln Lys Phe
        50                  55                  60

Lys Asp Lys Ala Thr Leu Thr Val Asp Lys Ser Ser Asn Thr Val Tyr
65                  70                  75                  80

Met Gln Leu Asn Ser Pro Thr Ser Glu Asp Ser Ala Val Tyr Tyr Cys
                85                  90                  95

Thr Arg Asn Gly Val Glu Gly Tyr Pro His Tyr Tyr Ala Met Glu Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala

```
                        325                 330                 335
Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
        450

<210> SEQ ID NO 12
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Met Thr Gln Thr Thr Ser Ala Leu Ser Ala Ser Leu Gly
1               5                   10                  15

Asp Arg Val Thr Ile Gly Cys Arg Ala Ser Gln Asp Leu Ser Asn His
            20                  25                  30

Leu Tyr Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Arg Asn Leu Glu Gln
65                  70                  75                  80

Glu Asp Val Ala Thr Tyr Phe Cys Gln Gln Gly Tyr Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Gly Tyr Thr Phe Thr Ser Tyr Trp
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asn Ile Tyr Pro Ser Asp Ser Tyr Thr
1               5

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Arg Asn Gly Val Glu Gly Tyr Pro His Tyr Tyr Ala Met Glu
1               5                   10                  15

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Gln Asp Leu Ser Asn His
1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Tyr Thr Ser
1

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 18

Cys Gln Gln Gly Tyr Thr Leu Pro Tyr
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Tyr Trp Ile Asn
1               5

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asn Ile Tyr Pro Ser Asp Ser Tyr Thr Asn Tyr Asn Gln Lys Phe Lys
1               5                   10                  15

Asp

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asn Gly Val Glu Gly Tyr Pro His Tyr Tyr Ala Met Glu Tyr
1               5                   10

<210> SEQ ID NO 22
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
                20                  25                  30

Trp Ile Asn Trp Val Lys Gln Arg Pro Gly Gln Gly Leu Glu Trp Ile
            35                  40                  45

Gly Asn Ile Tyr Pro Ser Asp Ser Tyr Thr Asn Tyr Asn Gln Lys Phe
        50                  55                  60

Lys Asp Lys Ala Thr Leu Thr Val Asp Lys Ser Ser Asn Thr Val Tyr
65                  70                  75                  80

Met Gln Leu Asn Ser Pro Thr Ser Glu Asp Ser Ala Val Tyr Tyr Cys
                85                  90                  95

Thr Arg Asn Gly Val Glu Gly Tyr Pro His Tyr Tyr Ala Met Glu Tyr
```

```
                  100                 105                 110
Trp Gly Gln Gly Thr Ser Val Thr Val Ser Ser
        115                 120

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Ala Ser Gln Asp Leu Ser Asn His Leu Tyr
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Tyr Thr Ser Arg Leu His Ser
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Gln Gly Tyr Thr Leu Pro Tyr Thr
1               5

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Met Thr Gln Thr Thr Ser Ala Leu Ser Ala Ser Leu Gly
1               5                   10                  15

Asp Arg Val Thr Ile Gly Cys Arg Ala Ser Gln Asp Leu Ser Asn His
            20                  25                  30

Leu Tyr Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Arg Asn Leu Glu Gln
65                  70                  75                  80

Glu Asp Val Ala Thr Tyr Phe Cys Gln Gln Gly Tyr Thr Leu Pro Tyr
                85                  90                  95

Thr Phe Gly Gly Gly Thr Lys Leu Glu Ile Lys
            100                 105
```

```
<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Gly Gly Gly Ser
1               5

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Gly Gly Ser Gly Gly Gly Gly Ser Gly Gly Gly Gly Ser
1               5                   10                  15
```

USE OF ANTI-CD137 ANTIBODY DRUG CONJUGATE (ADC) IN ALLOGENEIC CELL THERAPY

RELATED APPLICATIONS

This application is a continuation of International Application No. PCT/US2019/043119, filed on Jul. 23, 2019, which claims the benefit of priority under 35 U.S.C. § 119(e) to U.S. Provisional Patent Application No. 62/702,292, filed on Jul. 23, 2018. The entire contents of the foregoing applications are hereby incorporated by reference.

SEQUENCE LISTING

The instant application contains a Sequence Listing which has been submitted electronically in ASCII format and is hereby incorporated by reference in its entirety. Said ASCII copy, created on Jan. 22, 2021, is named M103034_2030US_C1_Sequence_Listing.txt and is 18,856 bytes in size.

FIELD OF THE INVENTION

The present invention provides methods for the treatment or prevention of rejection of an allogeneic cell therapy in a human subject, e.g., a chimeric antigen receptor (CAR) cell therapy, by administration of an antibody-drug conjugate (ADC) that binds an antigen expressed by cells of the host immune system responsible for mediating the rejection of the cell therapy.

BACKGROUND OF THE INVENTION

Allogeneic cell therapy includes the transplantation of cells to a patient, where the transplanted cells are derived from a donor other than the patient. Common types of allogeneic donors used for allogeneic cell therapy include HLA-matched siblings, matched unrelated donors, partially matched family member donors, related umbilical cord blood donors, and unrelated umbilical cord blood donors. An ultimate goal in cell therapy is to identify allogeneic cell therapies that can form the basis of "off the shelf" products (Brandenberger, et al. (2011). BioProcess International. 9 (suppl. I): 30-37), which will expand the use of allogeneic cell therapy.

One therapeutic area that holds enormous potential for allogeneic cell therapy is chimeric antigen receptor (CAR) therapy. CAR therapy is an immunological treatment that uses the body's own immune system to destroy cells expressing a specific antigen associated with a certain disease, such as cancer. In cancer, for example, CAR therapy enlists and strengthens the power of a patient's immune system to attack tumors. CAR therapy is based on an immune cell, such as a T cell, expressing a CAR which is generally a transmembrane fusion protein that combines an extracellular antigen binding domain, such as a scFv, with cytoplasmic activity signaling and "co-stimulatory" domains that signal the cell from the surface receptor. Thus, when immune cells, such as T-cells, express CARs, the immune cells are able to recognize and kill cells that express the antigen targeted by the antigen binding domain of the CAR (e.g., a tumor associated antigen) (Geyer and Brentjens (2016) *Cytotherapy* 18(11): 1393-1409).

To date, approved CAR therapy has relied on obtaining autologous cells from the patient and transforming the patient's own cells into CAR expressing cells, which are then used for therapy. A challenge for CAR therapy, however, is the time and cost associated with obtaining autologous cell, as autologous cells often require individualized protocols. The use of allogeneic cells would reduce time and costs associated with CAR therapy.

Despite its promise, the therapeutic use of allogeneic cells presently can have complications making this therapy challenging. In immune-competent hosts, transplanted allogeneic cells are rapidly rejected, a process termed host versus graft rejection (HvG). HvG can substantially reduce the efficacy of the transferred cells, as well as create adverse events in recipients, making the use of allogeneic cells limiting. There remains a need for methods that can overcome HvG rejection in order to further the potential of allogeneic cell therapy.

SUMMARY OF THE INVENTION

The present invention provides methods for preventing or treating rejection of transplanted allogeneic cells in a human subject. In particular, the methods disclosed herein can be used to treat or prevent host versus graft (HvG) in a patient receiving allogeneic cell therapy. The invention features methods of administering an anti-CD137 antibody-drug conjugate (ADC) so as to deplete a population of immune cells, such as activated T cells, expressing CD137 in the patient, in order to facilitate the administration of an allogeneic cell therapy. This selective depletion of CD137+ cells of the patient's immune system, e.g., activated T cells, prevents or significantly reduces the risk of rejection of the cell therapy.

In a first aspect, the invention features a method for treating or preventing rejection of allogeneic cells transplanted into a human subject, by (a) administering to the human subject a first amount of an allogeneic cell, wherein the first amount is sufficient to elicit a priming response to the allogeneic cell in the human subject; (b) administering an anti-CD137 antibody drug conjugate (ADC) to the human subject such that endogenous CD137+ activated T cells are depleted, wherein the anti-CD137 ADC comprises an anti-CD137 antibody, or antigen-binding fragment thereof, conjugated to a cytotoxin via a linker; and (c) administering a therapeutically effective amount of an allogeneic cell expressing a CAR to the human subject, wherein the allogeneic cell is the same type of allogeneic cell administered above, and wherein the CAR comprises an extracellular domain that binds to a tumor antigen, a transmembrane domain, and a cytoplasmic signaling domain; such that allogeneic cell rejection is treated or prevented in the human subject. In one embodiment, the method involves administering the first amount of the allogeneic cell to the human subject between about 48 hours to about 7 days before step (b). In another embodiment, the method involves administering the therapeutically effective amount of the allogeneic cell expressing the CAR to the human subject between about 24 hours to about 14 days after step (b).

In another aspect, the invention features a method of treating or preventing rejection of allogeneic cells transplanted into a human subject, by (a) administering an anti-CD137 ADC to the human subject, wherein the anti-CD137 ADC comprises an anti-CD137 antibody, or antigen-binding fragment thereof, conjugated to a cytotoxin via a linker, and wherein the human subject is characterized as having activated T cells directed to an allogeneic cell that was previously administered to the human subject; and (b) administering a therapeutically effective amount of an allogeneic cell expressing a CAR to the human subject, wherein the allogeneic cell is the same type of allogeneic cell described in (a), and wherein the CAR comprises an extracellular domain that binds to a tumor antigen, a transmembrane domain, and a cytoplasmic signaling domain, such that rejection of the transplanted allogeneic cells is treated or prevented in the human subject. In one embodiment, the method involves administering the effective amount of the allogeneic cell expressing the CAR to the human subject between about 24 hours to about 14 days after step (a).

In certain embodiments, the allogeneic cell is an allogeneic T cell or an allogeneic NK cell. In other embodiments, the effective amount of the allogeneic cell expressing the CAR is about $2\times10^6$ to about $3.0\times10^8$ cells/kg. In yet another embodiment, the allogeneic cell rejection is characterized by cytokine release syndrome (CRS). In other embodiments, the human subject has cancer or an autoimmune disease. In another embodiment, the anti-CD137 antibody, or antigen-binding fragment thereof, comprises a heavy chain variable region comprising a CDR1, a CDR2, and a CDR3 having an amino acid sequence as set forth in SEQ ID NOs: 19, 20, and 21, respectively, and comprises a light chain variable region comprising a CDR1, a CDR2, and a CDR3 having an amino acid sequence as set forth in SEQ ID NOs: 23, 24, and 25, respectively. In other embodiments, the anti-CD137 antibody, or antigen-binding fragment thereof, is chimeric or humanized.

In yet other embodiments, the anti-CD137 antibody, or antigen-binding fragment thereof, is an IgG1 isotype or an IgG4 isotype. In other embodiments, the cytotoxin is an antimitotic agent or an RNA polymerase inhibitor.

In other embodiments, the cytotoxin is a maytansine, a calicheamicin, a pyrrolobenzodiazepine, an indolinobenzodiazepine, or an auristatin. In one embodiment, the auristatin is monomethyl auristatin F (MMAF) or monomethyl auristatin E (MMAE). In one embodiment, the cytotoxin is a maytansine. In one embodiment, the cytotoxin is a pyrrolobenzodiazepine (PBD). For example, in some embodiments, the PBD may be selected from tesirine or talirine. In some embodiments, the cytotoxin may be a calicheamicin. For example, in some embodiments, the calicheamicin may be ozogamicin.

In another embodiment, the RNA polymerase inhibitor is an amatoxin. In yet another embodiment, the RNA polymerase inhibitor is an amanitin. In further embodiments, the amanitin is selected from the group consisting of α-amanitin, β-amanitin, γ-amanitin, ε-amanitin, amanin, amaninamide, amanullin, amanullinic acid, and proamanullin. In yet another embodiment, the anti-CD137 ADC is represented by the formula Ab-Z-L-Am, wherein Ab is an antibody or antigen-binding fragment thereof that binds CD137, L is a linker, Z is a chemical moiety, and Am is an amatoxin. In a certain embodiment, the linker-amatoxin conjugate Am-L-Z is represented by formula (III)

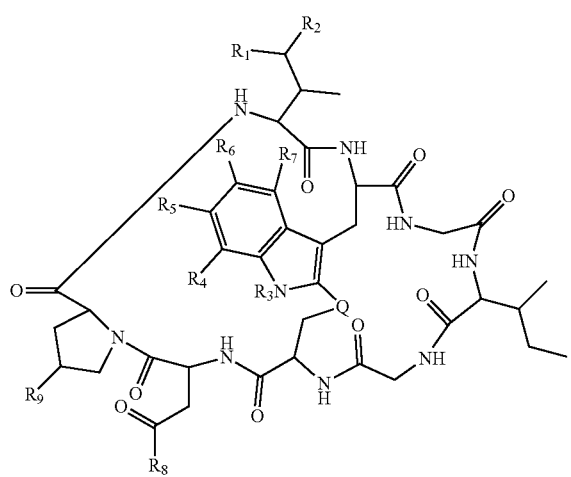

(III)

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocycloalkyl group;
$R_3$ is H, $R_C$, or $R_D$;
$R_4$, $R_5$, $R_6$, and $R_7$ are each independently H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
Q is —S—, —S(O)—, or —SO$_2$—;
$R_C$ is -L-Z;
$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;
L is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, optionally substituted heteroaryl; or comprises a dipeptide; or comprises —(($CH_2$)$_m$O)$_n$($CH_2$)$_m$—, where m and n are each independently selected from 1, 2, 3, 4, 5, 6, 7, 8, 9, and 10; or a combination thereof; and
Z is a chemical moiety formed from a coupling reaction between a reactive substituent present on L and a reactive substituent present within the anti-CD137 antibody or antigen-binding fragment thereof.

In a certain embodiment, the linker-amatoxin conjugate Am-L-Z is represented by formula (III)

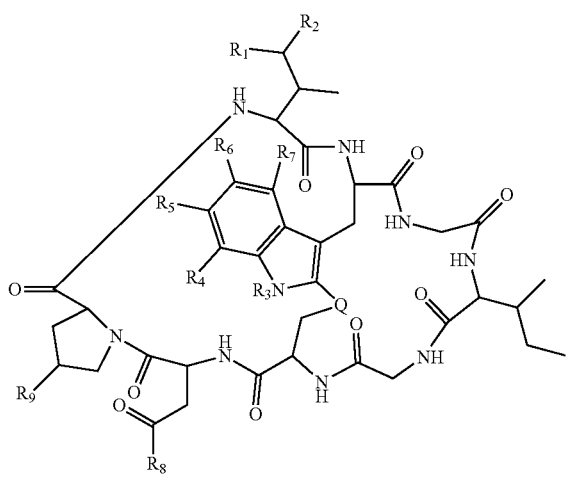

(III)

wherein $R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form an optionally substituted 5-membered heterocycloalkyl group;

$R_3$ is H, $R_C$, or $R_D$;

$R_4$, $R_5$, $R_6$, and $R_7$ are each independently H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

Q is —S—, —S(O)—, or —$SO_2$—;

$R_C$ is -L-Z;

$R_D$ is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, or optionally substituted heteroaryl;

L is a linker; and

Z is a chemical moiety formed from a coupling reaction between a reactive substituent present on L and a reactive substituent present within the anti-CD137 antibody or antigen-binding fragment thereof.

In one embodiment of Formula (III), L is a peptide containing linker.

In some embodiments, the linker comprises one or more of a dipeptide, a p-aminobenzyl (PAB) group, an optionally substituted $C_1$-$C_6$ alkyl, an optionally substituted $C_1$-$C_6$ heteroalkyl, an optionally substituted $C_2$-$C_6$ alkenyl, an optionally substituted $C_2$-$C_6$ heteroalkenyl, an optionally substituted $C_2$-$C_6$ alkynyl, an optionally substituted $C_2$-$C_6$ heteroalkynyl, an optionally substituted $C_3$-$C_6$ cycloalkyl, an optionally substituted heterocycloalkyl, an optionally substituted aryl, an optionally substituted heteroaryl, a solubility enhancing group, —(C=O)—, a —($CH_2CH_2O$)$_p$— group, wherein p is an integer from 1-6, (($CH_2$)$_m$O)$_n$($CH_2$)$_m$—, where n and each m are each independently selected from 1, 2, 3, 4, 5, 6, 7, 8, 9, and 10; or a combination thereof.

In some embodiments, the linker comprises a (($CH_2$)$_m$O)$_n$($CH_2$)$_m$ group and a heteroaryl group, wherein the heteroaryl group is a triazole. In some embodiments, the (($CH_2$)$_m$O)$_n$($CH_2$)$_m$ group and triazole together comprise

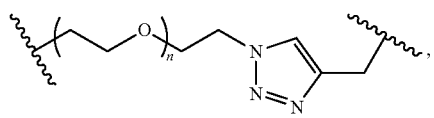

where n is from 1 to 10, and the wavy lines indicate attachment points to additional linker components, the chemical moiety Z, or the amatoxin.

In some embodiments, Am contains exactly one $R_C$ substituent.

In other embodiments, the antimitotic agent is a maytansine, a calicheamicin, a pyrrolobenzodiazepine, an indolinobenzodiazepine, or an auristatin. In another embodiment, the auristatin is monomethyl auristatin F (MMAF) or monomethyl auristatin E (MMAE).

In certain embodiments, the linker of the ADC is N-beta-maleimidopropionyl-Val-Ala-para-aminobenzyl (BMP-Val-Ala-PAB). In one embodiment, the linker of the ADC is N-beta-maleimidopropionyl-Val-Ala-para-aminobenzyl (BMP-Val-Ala-PAB). In some embodiments, the linker L and the chemical moiety Z, taken together as L-Z, is

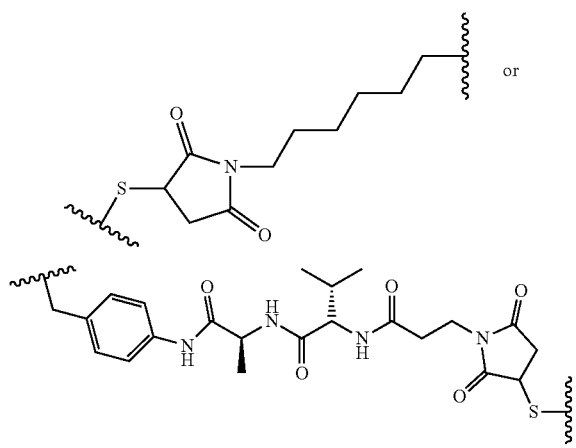

where S is a sulfur atom which represents the reactive substituent present within an antibody, or antigen-binding fragment thereof, that binds CD5 (e.g., from the —SH group of a cysteine residue).

In some embodiments, L-Z is

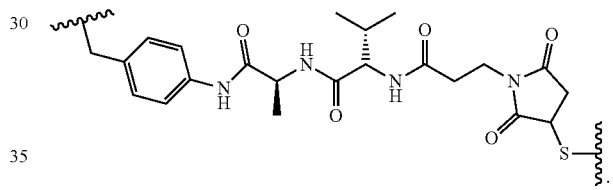

In one embodiment, the ADC is represented by any one of the following structures:

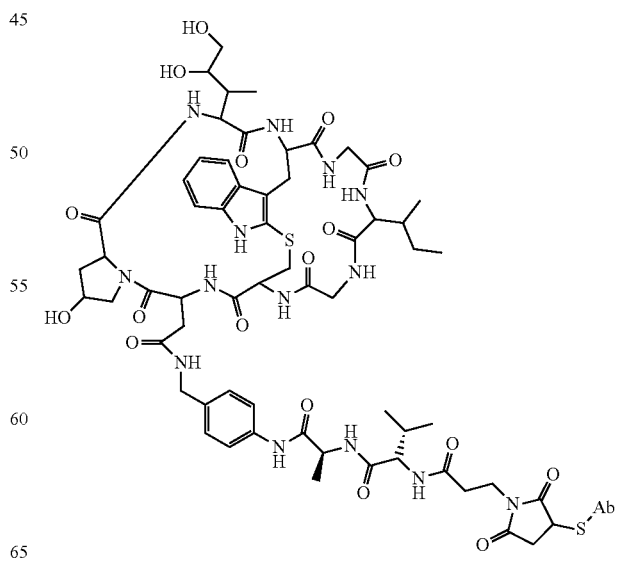

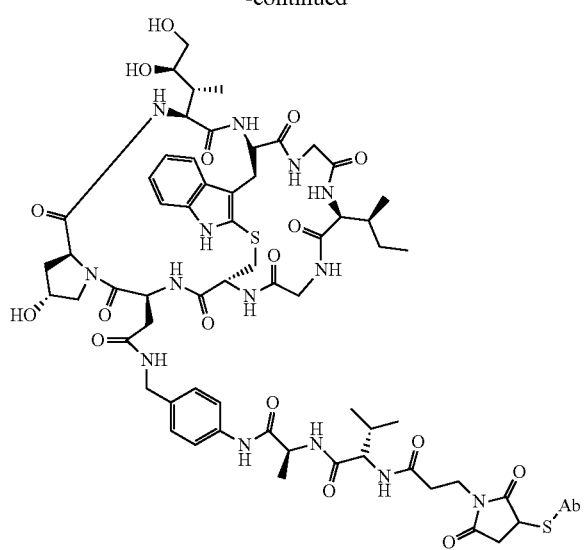

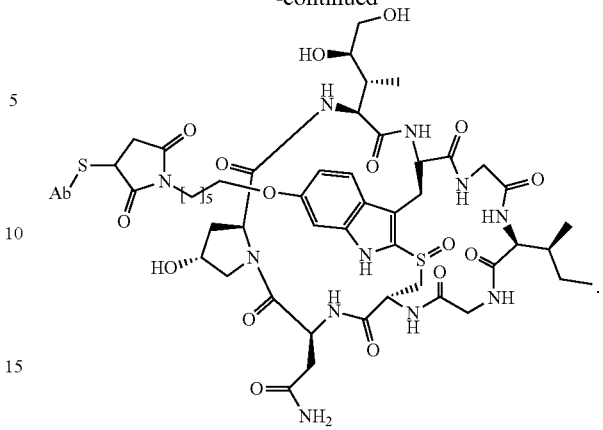

In one embodiment, the ADC is represented by one of the following structures:

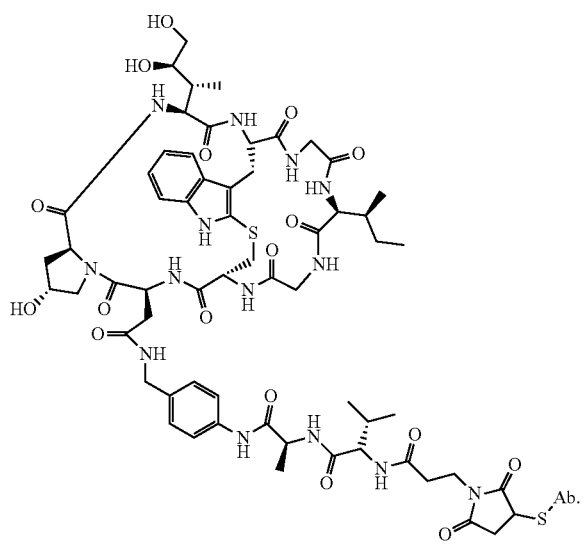

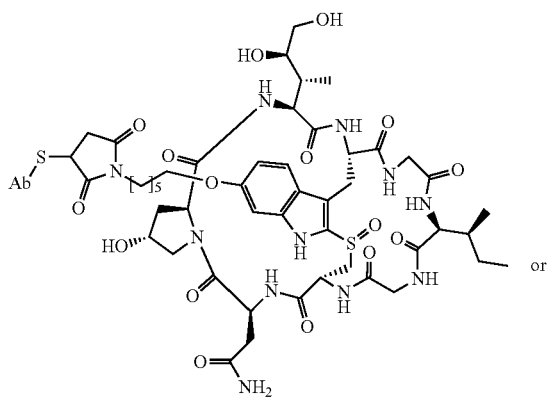

or

In other embodiments, the ADC has a serum half-life of 3 days or less. In other embodiments, the extracellular domain comprises an scFv antibody or a single chain T cell receptor (scTCR). In yet another embodiment, the extracellular domain comprises a non-immunoglobulin scaffold protein. In other embodiments, the extracellular domain of the CAR binds to tumor antigen selected from the group consisting of CD19, CD22, CD30, CD7, BCMA, CD137, CD22, CD20, AFP, GPC3, MUC1, mesothelin, CD38, PD1, EGFR (e.g., EGFRvIII), MG7, BCMA, TACI, CEA, PSCA, CEA, HER2, MUC1, CD33, ROR2, NKR-2, PSCA, CD28, TAA, NKG2D, or CD123. In other embodiments, the cytoplasmic signaling domain of the CAR comprises a CD28 cytoplasmic signaling domain, a CD3 zeta cytoplasmic signaling domain, an OX40 cytoplasmic signaling domain, and/or a CD137 cytoplasmic signaling domain. In yet another embodiment, the cytoplasmic signaling domain of the CAR comprises a CD3 zeta cytoplasmic signaling domain. In certain embodiments, the cancer is leukemia, adult advanced cancer, pancreatic cancer, non-resectable pancreatic cancer, colorectal cancer, metastatic colorectal cancer, ovarian cancer, triple-negative breast cancer, hematopoietic/lymphoid cancer, colon cancer liver metastasis, small cell lung cancer, non-small cell lung cancer, B-cell lymphoma, relapsed or refractory B-cell lymphoma, follicular lymphoma, mantle cell lymphoma, diffuse large cell lymphoma, relapsed or refractory diffuse large cell lymphoma, anaplastic large cell lymphoma, primary mediastinal B-cell lymphoma, recurrent mediastinal, refractory mediastinal large B-cell lymphoma, large B-cell lymphoma, Hodgkin lymphoma, non-Hodgkin lymphoma, relapsed or refractory non-Hodgkin lymphoma, refractory aggressive non-Hodgkin lymphoma, B-cell non-Hodgkin lymphoma, refractory non-Hodgkin lymphoma, colorectal carcinoma, gastric carcinoma, pancreatic carcinoma, triple-negative invasive breast carcinoma, renal cell carcinoma, lung squamous cell carcinoma, hepatocellular carcinoma, urothelial carcinoma, leukemia, B-cell leukemia, B-cell acute lymphocytic leukemia, B-cell acute lymphoblastic leukemia, adult acute lymphoblastic leukemia, B-cell prolymphocytic leukemia, childhood acute lymphoblastic leukemia, refractory childhood acute lymphoblastic leukemia, acute leukemia, acute lymphoblastic leukemia, acute lymphocytic leukemia, prolymphocytic leukemia, chronic lymphocytic leukemia, acute myeloid leukemia, recurrent plasma cell myeloma, refractory plasma cell myeloma, multiple myeloma, relapsed or refractory multiple myeloma, multiple myeloma of bone, malignant glioma of brain, myelodysplastic syndrome, EGFR-positive colorectal cancer, glioblastoma multiforme, neoplasms, blastic plasmacytoid dendritic cell neoplasms, liver metastases, solid tumors, advanced solid tumors, mesothelin positive tumors, hematological malignancies, or other advanced malignancies.

DETAILED DESCRIPTION

Figure 1A:
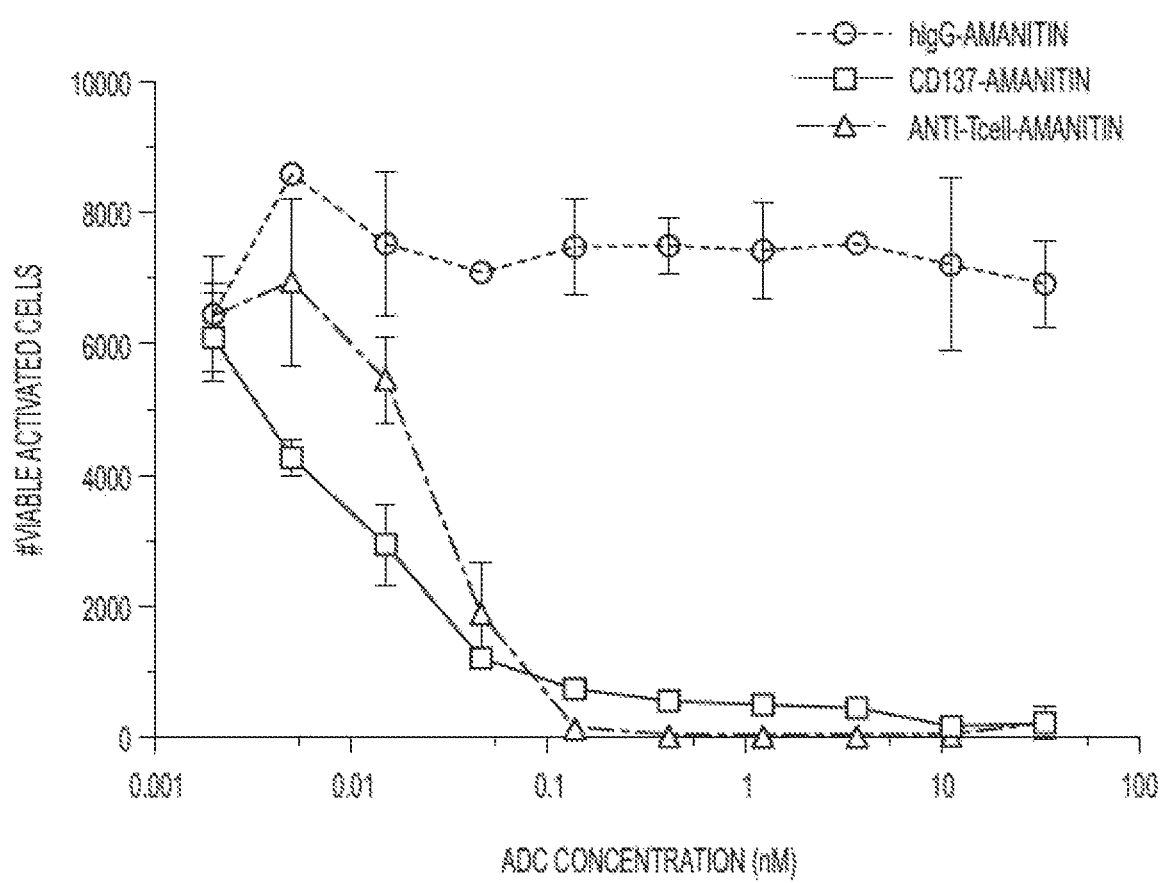
FIGS. 1A and 1B graphically depict results of an in vitro T cell killing assay including an anti-CD137-amanitin ADC (i.e., "CD137-Amanitin") and an anti-T cell specific-amanitin ADC (i.e., "anti-Tcell-Amanitin") in comparison to a negative control (i.e., "hIgG-Amanitin"). The results show the number of viable activated cells (FIG. 1A) or viable non-activated cells (FIG. 1B) of each ADC (y-axis) as a function of ADC concentration (x-axis).

Disclosed herein are methods of treating or preventing rejection of transplanted allogeneic cells in a human subject, i.e., treatment or prevention of host versus graft (HvG) disease. The methods disclosed herein include administration of both an anti-CD137 antibody drug conjugate (ADC) (that binds to endogenous CD137+ immune cells, e.g., activated T cells) and allogeneic cell therapy. By administering an anti-CD137 ADC to a human patient receiving an allogeneic cell transplant, endogenous CD137+ T cells are depleted, thus reducing the risk of a reaction by the endogenous cells against the allogeneic cell therapy. The methods disclosed herein can be used in combination with allogeneic chimeric antigen receptor (CAR) therapy, as the combined use of an anti-CD137 ADC and allogeneic cells expressing a CAR provides for acceptance of the allogeneic cells in the recipient patient and reduces the risk of host versus graft (HvG) reactions that can render the CAR expressing cells ineffective.

I. Definitions

As used herein, the term "about" refers to a value that is within 5% above or below the value being described.

As used herein, the term "allogeneic", when used in the context of transplantation, is used to define cells (or tissue or an organ) that are transplanted from a donor to a recipient, where the donor and the recipient are different individuals of the same species.

As used herein, the term "autologous" refers to cells or a graft where the donor and recipient are the same subject.

As used herein, the term "xenogeneic" refers to cells where the donor and recipient species are different.

As used herein, the term "immune cell" is intended to include, but is not limited to, a cell that is of hematopoietic origin and that plays a role in the immune response. Immune cells include, but are not limited to, T cells and natural killer (NK) cells. Natural killer cells are well known in the art. In one embodiment, natural killer cells include cell lines, such as NK-92 cells. Further examples of NK cell lines include NKG, YT, NK-YS, HANK-1, YTS cells, and NKL cells. An immune cell can be allogeneic or autologous.

An "engineered cell" means any cell of any organism that is modified, transformed, or manipulated by addition or modification of a gene, a DNA or RNA sequence, or protein or polypeptide. Isolated cells, host cells, and genetically engineered cells of the present disclosure include isolated immune cells, such as NK cells and T cells that contain the DNA or RNA sequences encoding a CAR and express the CAR on the cell surface. Isolated host cells and engineered cells may be used, for example, for enhancing an NK cell activity or a T lymphocyte activity, treatment of cancer, and treatment of autoimmune diseases. In an embodiment, the engineered cell includes immune cells, e.g., T-cells or Natural Killer (NK cells).

As used herein, the term "antibody" refers to an immunoglobulin molecule that specifically binds to, or is immunologically reactive with, a particular antigen. An antibody includes, but is not limited to, monoclonal antibodies, polyclonal antibodies, multispecific antibodies (e.g., bispecific antibodies), and antibody fragments so long as they exhibit the desired antigen-binding activity.

Generally, antibodies comprise heavy and light chains containing antigen binding regions. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The term "antigen-binding fragment," as used herein, refers to one or more portions of an antibody that retain the ability to specifically bind to a target antigen. The antigen-binding function of an antibody can be performed by fragments of a full-length antibody. The antibody fragments can be, for example, a Fab, F(ab')2, scFv, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the VL, VH, CL, and CH1 domains; (ii) a F(ab')2 fragment, a bivalent fragment containing two Fab fragments linked by a disulfide bridge at the hinge region; (iii) a Fd fragment consisting of the VH and $CH_1$ domains; (iv) a Fv fragment consisting of the VL and VH domains of a single arm of an antibody, (v) a dAb including VH and VL domains; (vi) a dAb fragment that consists of a VH domain (see, e.g., Ward et al., Nature 341:544-546, 1989); (vii) a dAb which consists of a VH or a VL domain; (viii) an isolated complementarity determining region (CDR); and (ix) a combination of two or more (e.g., two, three, four, five, or six) isolated CDRs which may optionally be joined by a synthetic linker. Furthermore, although the two domains of the Fv fragment, VL and VH, are coded for by separate genes, they can be joined, using recombinant methods, by a linker that enables them to be made as a single protein chain in which the VL and VH regions pair to form monovalent molecules (known as single chain Fv (scFv); see, for example, Bird et al., Science 242:423-426, 1988 and Huston et al., Proc. Natl. Acad. Sci. USA 85:5879-5883, 1988). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in certain cases, by chemical peptide synthesis procedures known in the art.

An "intact" or "full length" antibody, as used herein, refers to an antibody having two heavy (H) chain polypeptides and two light (L) chain polypeptides interconnected by disulfide bonds.

As used herein, the term "anti-CD137 antibody" or "an antibody that binds to CD137" or an "anti-CD137 ADC" or "an ADC that binds to CD137" refers to an antibody or ADC that specifically binds to human CD137 as CD137 is found on the cell surface of cells, such as T cells. The amino acid sequence of human CD137 extracellular domain is described below in SEQ ID NO:1.

```
                                              (SEQ ID NO: 1)
MGNSCYNIVATLLLVLNFERTRSLQDPCSNCPAGTFCDNNRNQICSPCP

PNSESSAGGQRTCDICRQCKGVFRTRKECSSTSNAECDCTPGFHCLGAG

CSMCEQDCKQGQELTKKGCKDCCFGTFNDQKRGICRPWTNCSLDGKSVL

VNGTKERDVVCGPSPADLSPGASSVTPPAPAREPGHSPQISFFLALTST

ALLFLLFFLTLRFSVVKRGRKKLLYIFKQPFMRPVQTTQEEDGCSCRFP

EEEEGGCEL
```

The term "specifically binds", as used herein, refers to the ability of an antibody (or ADC) to recognize and bind to a specific protein structure (epitope) rather than to proteins generally. If an antibody is specific for epitope "A", the presence of a molecule containing epitope A (or free, unlabeled A), in a reaction containing labeled "A" and the antibody, will reduce the amount of labeled A bound to the antibody. By way of example, an antibody "binds specifically" to a target if the antibody, when labeled, can be competed away from its target by the corresponding non-labeled antibody. In one embodiment, an antibody specifically binds to a target, e.g., CD137, if the antibody has a $K_D$ for the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, or less (less meaning a number that is less than $10^{-12}$, e.g. $10^{-13}$). In one embodiment, the term "specific binding to CD137" or "specifically binds to CD137," as used herein, refers to an antibody or that binds to CD137 and has a dissociation constant ($K_D$) of $1.0 \times 10^{-7}$ M or less, as determined by surface plasmon resonance. In one embodiment, $K_D$ is determined according to standard bio-layer interferometry (BLI). It shall be understood, however, that the antibody may be capable of specifically binding to two or more antigens which are related in sequence. For example, in one embodiment, an antibody can specifically bind to both human and a non-human (e.g., mouse or non-human primate) orthologs of CD137.

The term "monoclonal antibody" as used herein is not limited to antibodies produced through hybridoma technology. A monoclonal antibody is derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

The term "chimeric" antibody as used herein refers to an antibody having variable sequences derived from a non-human immunoglobulin, such as a rat or a mouse antibody, and human immunoglobulin constant regions, typically chosen from a human immunoglobulin template. Methods for producing chimeric antibodies are known in the art. See, e.g., Morrison, 1985, Science 229(4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816,397.

As used herein, the term "half-life" refers to the time it takes for the plasma concentration of the antibody drug in the body to be reduced by one half or 50%. This 50% reduction in serum concentration reflects the amount of drug circulating.

As used herein, the term "host-versus-graft disease" or "HvG" refers to transplant rejection whereby allogeneic cells, tissue, or an organ are rejected by a recipient's immune system "Humanized" forms of non-human (e.g., murine) antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332.

As used herein, the terms "chimeric antigen receptor" or "CAR" refer to a recombinant polypeptide comprising at least an extracellular domain capable of specifically binding an antigen, a transmembrane domain, and at least one intracellular signaling domain. Generally a CAR is a genetically engineered receptor that redirects cytotoxicity of immune effector cells toward cells presenting the given antigen. CARs are molecules that combine antibody-based specificity for a desired antigen (e.g., a tumor antigen) with a T cell receptor-activating intracellular domain to generate a chimeric protein that exhibits a specific cellular immune activity. In particular embodiments, CARs comprise an extracellular domain (also referred to as a binding domain or antigen-specific binding domain), a transmembrane domain, and an intracellular (cytoplasmic) signaling domain. Engagement of the antigen binding domain of the CAR with the target antigen on the surface of a target cell results in clustering of the CAR and delivers an activation stimulus to the CAR-containing cell. A main characteristic of a CAR is its ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific co-receptors. In some embodiments, a CAR comprises an extracellular binding domain that specifically binds to a tumor antigen; a transmembrane domain; and one or more intracellular signaling domains. In various embodiments, a CAR comprises an extracellular binding domain that specifically binds human CD137; a transmembrane domain; and one or more intracellular signaling domains.

As used herein, the term "CAR therapy" refers to administration of an immune cell that has been engineered to express a CAR, to a human subject for the treatment of a given disease, e.g., cancer or an autoimmune disease. CAR therapy refers to the specific treatment of the patient with the engineered immune cells and is not intended to include therapies that commonly are used in conjunction with CAR cell treatment, e.g., lymphodepleting chemotherapy. Notably, where the term "cell" is used throughout, populations of cells are also included by the term unless otherwise specified. For example, as CAR therapy requires administration of a population of engineered cells.

As used herein, the term "combination" or "combination therapy" refers to the use of two (or more) therapies in a single human patient. The terms are not intended to refer to a combination composition. For example, described herein is a combination therapy that comprises administering an anti-CD137 ADC and allogeneic CAR therapy.

The term "priming response", as used herein, refers to the immune response elicited in a human subject when the subject's immune system is first presented with an antigen. The first contact of a T or B cell with a specific antigen is called priming and causes activated allo-antigen T cells. A priming dose can be a single dose, or multiple doses needed to elicit a response. A "priming amount" is an amount of an antigen, e.g., an allogeneic cell, used to elicit the priming response. A priming amount is not generally a therapeutically effective amount, but rather an amount used to activate a subject's T cells. In some embodiments, the priming amount of an allogeneic cell is less than a therapeutically effective amount of an allogeneic cell. In one embodiment, a priming response is elicited upon administration of an allogeneic cell to a human subject, such that CD137+ T cells are activated.

The term "deplete," in the context of the effect of an anti-CD137 antibody or ADC on CD137-expressing cells, refers to a reduction in the number of or elimination of CD137-expressing cells.

As used herein, the term "effective amount" or "therapeutically effective amount" refers to an amount that is sufficient to achieve the desired result or to have an effect on an autoimmune disease or cancer.

As used herein, the terms "subject" and "patient" refer to an organism, such as a human, that receives treatment for a particular disease or condition as described herein.

As used herein "to treat" or "treatment", refer to any improvement of any consequence of disease, such as prolonged survival, less morbidity, and/or a lessening of side effects which are the byproducts of an alternative therapeutic modality; as is readily appreciated in the art, full eradication of disease is a preferred but albeit not a requirement for a treatment act. Beneficial or desired clinical results include, but are not limited to, promoting acceptance of allogeneic CAR expressing immune cells. Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present invention may occur prior to onset of a disease. The term does not imply that the disease state is completely avoided.

As used herein, the term "vector" includes a nucleic acid vector, such as a plasmid, a DNA vector, a plasmid, a RNA vector, virus, or other suitable replicon. Expression vectors described herein may contain a polynucleotide sequence as well as, for example, additional sequence elements used for the expression of proteins and/or the integration of these polynucleotide sequences into the genome of a mammalian cell. Certain vectors that can be used for the expression of CARs or include plasmids that contain regulatory sequences, such as promoter and enhancer regions, which direct gene transcription. Other useful vectors for antibody or CAR expression contain polynucleotide sequences that enhance the rate of translation of these genes or improve the stability or nuclear export of the mRNA that results from gene transcription. These sequence elements may include, for example, 5' and 3' untranslated regions and a polyadenylation signal site in order to direct efficient transcription of the gene carried on the expression vector. The expression vectors described herein may also contain a polynucleotide encoding a marker for selection of cells that contain such a vector. Examples of a suitable marker include genes that encode resistance to antibiotics, such as ampicillin, chloramphenicol, kanamycin, and nourseothricin.

As used herein, the term "antibody drug conjugate" or "ADC" refers to an antibody which is linked to a cytotoxin. An ADC is formed by the chemical bonding of a reactive functional group of one molecule, such as an antibody or antigen-binding fragment thereof, with an appropriately reactive functional group of another molecule, such as a cytotoxin described herein. Conjugates may include a linker between the two molecules bound to one another, e.g., between an antibody and a cytotoxin. Notably, the term "conjugate" (when referring to a compound) is also referred to interchangeably herein as a "drug conjugate", "antibody drug conjugate" or "ADC". Examples of linkers that can be used for the formation of a conjugate include peptide-containing linkers, such as those that contain naturally occurring or non-naturally occurring amino acids, such as D-amino acids. Linkers can be prepared using a variety of strategies described herein and known in the art. Depending on the reactive components therein, a linker may be cleaved, for example, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012).

As used herein, the term "coupling reaction" refers to a chemical reaction in which two or more substituents suitable for reaction with one another react so as to form a chemical moiety that joins (e.g., covalently) the molecular fragments bound to each substituent. Coupling reactions include those in which a reactive substituent bound to a fragment that is a cytotoxin, such as a cytotoxin known in the art or described herein, reacts with a suitably reactive substituent bound to a fragment that is an antibody, or antigen-binding fragment thereof, such as an antibody, antigen-binding fragment thereof, or specific anti-CD137 antibody that binds CD137 known in the art or described herein. Examples of suitably reactive substituents include a nucleophile/electrophile pair (e.g., a thiol/haloalkyl pair, an amine/carbonyl pair, or a thiol/α,β-unsaturated carbonyl pair, among others), a diene/dienophile pair (e.g., an azide/alkyne pair, among others), and the like. Coupling reactions include, without limitation, thiol alkylation, hydroxyl alkylation, amine alkylation, amine condensation, amidation, esterification, disulfide formation, cycloaddition (e.g., [4+2] Diels-Alder cycloaddition, [3+2] Huisgen cycloaddition, among others), nucleophilic aromatic substitution, electrophilic aromatic substitution, and other reactive modalities known in the art or described herein. As used herein, the term "microtubule-binding agent" refers to a compound which acts by disrupting the microtubular network that is essential for mitotic and interphase cellular function in a cell. Examples of microtubule-binding agents include, but are not limited to, maytasine, maytansinoids, and derivatives thereof, such as those described herein or known in the art, vinca alkaloids, such as vinblastine, vinblastine sulfate, vincristine, vincristine sulfate, vindesine, and vinorelbine, taxanes, such as docetaxel and paclitaxel, macrolides, such as discodermolides, cochicine, and epothilones, and derivatives thereof, such as epothilone B or a derivative thereof.

As used herein, the term "amatoxin" refers to a member of the amatoxin family of peptides produced by *Amanita phalloides* mushrooms, or derivative thereof, such as a variant or derivative thereof capable of inhibiting RNA polymerase II activity. Amatoxins may be isolated from a variety of mushroom species (e.g., *Amanita phalloides, Galerina marginata, Lepiota brunneo-incarnata*) or may be prepared semi-synthetically or synthetically. A member of this family, α-amanitin, is described in Wieland, *Int. J. Pept. Protein Res.* 1983, 22(3):257-276. A derivative of an amatoxin may be obtained by chemical modification of a naturally occurring compound ("semi-synthetic"), or may be obtained from an entirely synthetic source. Synthetic routes to various amatoxin derivatives are disclosed in, for example, U.S. Pat. No. 9,676,702 and in Perrin et al., J. Am. Chem. Soc. 2018, 140, p. 6513-6517, each of which is incorporated by reference herein in their entirety with respect to synthetic methods for preparing and derivatizing amatoxins.

Amatoxins useful in conjunction with the compositions and methods described herein include compounds such, as, but not limited to, compounds of Formula (II), e.g., α-amanitin, β-amanitin, γ-amanitin, ε-amanitin, amanin, amaninamide, amanullin, amanullinic acid, or proamanullin. As described herein, amatoxins may be conjugated to an antibody, or antigen-binding fragment thereof, for instance, by way of a linker moiety (L) (thus forming an ADC). Exemplary methods of amatoxin conjugation and linkers useful for such processes are described below. Structures of exemplary amatoxin-linker conjugates are represented by Formulas (III), (IIIA), and (IIIB). Exemplary linker-containing amatoxins useful for conjugation to an antibody, or antigen-binding fragment, in accordance with the compositions and methods are also described herein.

The term "acyl" as used herein refers to —C(=O)R, wherein R is hydrogen ("aldehyde"), $C_1$-$C_{12}$ alkyl, $C_2$-$C_{12}$ alkenyl, $C_2$-$C_{12}$ alkynyl, $C_3$-$C_7$ carbocyclyl, $C_6$-$C_{20}$ aryl, 5-10 membered heteroaryl, or 5-10 membered heterocyclyl, as defined herein. Non-limiting examples include formyl, acetyl, propanoyl, benzoyl, and acryloyl.

The term "$C_1$-$C_{12}$ alkyl" as used herein refers to a straight chain or branched, saturated hydrocarbon having from 1 to 12 carbon atoms. Representative $C_1$-$C_{12}$ alkyl groups include, but are not limited to, -methyl, -ethyl, -n-propyl, -n-butyl, -n-pentyl, and -n-hexyl; while branched $C_1$-$C_{12}$ alkyls include, but are not limited to, -isopropyl, -sec-butyl, -isobutyl, -tert-butyl, -isopentyl, and 2-methylbutyl. A $C_1$-$C_{12}$ alkyl group can be unsubstituted or substituted.

The term "alkenyl" as used herein refers to $C_2$-$C_{12}$ hydrocarbon containing normal, secondary, or tertiary carbon atoms with at least one site of unsaturation, i.e., a carbon-carbon, $sp^2$ double bond. Examples include, but are not limited to: ethylene or vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, and the like. An alkenyl group can be unsubstituted or substituted.

"Alkynyl" as used herein refers to a $C_2$-$C_{12}$ hydrocarbon containing normal, secondary, or tertiary carbon atoms with at least one site of unsaturation, i.e., a carbon-carbon, sp triple bond. Examples include, but are not limited to acetylenic and propargyl. An alkynyl group can be unsubstituted or substituted.

"Aryl" as used herein refers to a $C_6$-$C_{20}$ carbocyclic aromatic group. Examples of aryl groups include, but are not limited to, phenyl, naphthyl and anthracenyl. An aryl group can be unsubstituted or substituted.

"Arylalkyl" as used herein refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms. An alkaryl group can be unsubstituted or substituted.

"Cycloalkyl" as used herein refers to a saturated carbocyclic radical, which may be mono- or bicyclic. Cycloalkyl groups include a ring having 3 to 7 carbon atoms as a monocycle or 7 to 12 carbon atoms as a bicycle. Examples of monocyclic cycloalkyl groups include cyclopropyl, cyclobutyl, cyclopentyl, cyclohexyl, cycloheptyl, and cyclooctyl. A cycloalkyl group can be unsubstituted or substituted.

"Cycloalkenyl" as used herein refers to an unsaturated carbocyclic radical, which may be mono- or bicyclic. Cycloalkenyl groups include a ring having 3 to 6 carbon atoms as a monocycle or 7 to 12 carbon atoms as a bicycle. Examples of monocyclic cycloalkenyl groups include 1-cyclopent-1-enyl, 1-cyclopent-2-enyl, 1-cyclopent-3-enyl, 1-cyclohex-1-enyl, 1-cyclohex-2-enyl, and 1-cyclohex-3-enyl. A cycloalkenyl group can be unsubstituted or substituted.

"Heteroaralkyl" as used herein refers to an acyclic alkyl radical in which one of the hydrogen atoms bonded to a carbon atom, typically a terminal or sp3 carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo[4,5], [5,5], [5,6], or [6,6] system.

"Heteroaryl" and "heterocycloalkyl" as used herein refer to an aromatic or non-aromatic ring system, respectively, in which one or more ring atoms is a heteroatom, e.g. nitrogen, oxygen, and sulfur. The heteroaryl or heterocycloalkyl radical comprises 2 to 20 carbon atoms and 1 to 3 heteroatoms selected from N, O, P, and S. A heteroaryl or heterocycloalkyl may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo[4,5], [5,5], [5,6], or [6,6] system. Heteroaryl and heterocycloalkyl can be unsubstituted or substituted.

Heteroaryl and heterocycloalkyl groups are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heteroaryl groups include by way of example and not limitation pyridyl, thiazolyl, tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, benzotriazolyl, benzisoxazolyl, and isatinoyl.

Examples of heterocycloalkyls include by way of example and not limitation dihydroypyridyl, tetrahydropyridyl (piperidyl), tetrahydrothiophenyl, piperidinyl, 4-piperidonyl, pyrrolidinyl, 2-pyrrolidonyl, tetrahydrofuranyl, tetrahydropyranyl, bis-tetrahydropyranyl, tetrahydroquinolinyl, tetrahydroisoquinolinyl, decahydroquinolinyl, octahydroisoquinolinyl, piperazinyl, quinuclidinyl, and morpholinyl.

By way of example and not limitation, carbon bonded heteroaryls and heterocycloalkyls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heteroaryls and heterocycloalkyls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or beta-carboline. Still more typically, nitrogen bonded heterocycles include 1-aziridyl, 1-azetedyl, 1-pyrrolyl, 1-imidazolyl, 1-pyrazolyl, and 1-piperidinyl.

"Substituted" as used herein and as applied to any of the above alkyl, alkenyl, alkynyl, aryl, arylalkyl, cycloalkyl, heteroaryl, heterocyclyl, and the like, means that one or more hydrogen atoms are each independently replaced with a substituent. Unless otherwise constrained by the definition of the individual substituent, the foregoing chemical moieties, such as "alkyl", "alkylene", "heteroalkyl", "heteroalkylene", "alkenyl", "alkenylene", "heteroalkenyl", "heteroalkenylene", "alkynyl", "alkynylene", "heteroalkynyl", "heteroalkynylene", "cycloalkyl", "cycloalkylene", "heterocyclolalkyl", heterocycloalkylene", "aryl," "arylene", "heteroaryl", and "heteroarylene" groups can optionally be substituted. Typical substituents include, but are not limited to, —X, —R, —OH, —OR, —SH, —SR, $NH_2$, —NHR, —N(R)$_2$, —N$^+$(R)$_3$, —CX$_3$, —CN, —OCN, —SCN, —NCO, —NCS, —NO, —NO$_2$, —N$_3$, —NC(=O)H, —NC(=O)R, —C(=O)H, —C(=O)R, —C(=O)NH$_2$, —C(=O)N(R)$_2$, —SO$_3$—, —SO$_3$H, —S(=O)$_2$R, —OS(=O)$_2$OR, —S(=O)$_2$NH$_2$, —S(=O)$_2$N(R)$_2$, —S(=O)R, —OP(=O)(OH)$_2$, —OP(=O)(OR)$_2$, —P(=O)(OR)$_2$, —PO$_3$, —PO$_3$H$_2$, —C(=O)X, —C(=S)R, —CO$_2$H, —CO$_2$R, —CO$_2$—, —C(=S)OR, —C(=O)SR, —C(=S)SR, —C(=O)NH$_2$, —C(=O)N(R)$_2$, —C(=S)NH$_2$, —C(=S)N(R)$_2$, —C(=NH)NH$_2$, and —C(=NR)N(R)$_2$; wherein each X is independently selected for each occasion from F, Cl, Br, and I; and each R is independently selected for each occasion from $C_1$-$C_{12}$ alkyl, $C_6$-$C_{20}$ aryl, $C_3$-$C_{14}$ heterocycloalkyl or heteroaryl, protecting group and prodrug moiety. Wherever a group is described as "optionally substituted," that group can be substituted with one or more of the above substituents, independently for each occasion.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene," "alkenylene," "arylene," "heterocycloalkylene," and the like.

Wherever a substituent is depicted as a di-radical (i.e., has two points of attachment to the rest of the molecule), it is to be understood that the substituent can be attached in any directional configuration unless otherwise indicated.

"Isomerism" means compounds that have identical molecular formulae but differ in the sequence of bonding of their atoms or in the arrangement of their atoms in space.

Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers," or sometimes "optical isomers."

A carbon atom bonded to four non-identical substituents is termed a "chiral center." "Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116). A mixture containing equal amounts of individual enantiomeric forms of opposite chirality is termed a "racemic mixture."

The compounds disclosed in this description and in the claims may comprise one or more asymmetric centers, and different diastereomers and/or enantiomers of each of the compounds may exist. The description of any compound in this description and in the claims is meant to include all enantiomers, diastereomers, and mixtures thereof, unless stated otherwise. In addition, the description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the invention of the present application is not limited to that specific enantiomer. Accordingly, enantiomers, optical isomers, and diastereomers of each of the structural formulae of the present disclosure are contemplated herein. In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. The compounds may occur in different tautomeric forms. The compounds according to the disclosure are meant to include all tautomeric forms, unless stated otherwise. When the structure of a compound is depicted as a specific tautomer, it is to be understood that the invention of the present application is not limited to that specific tautomer.

The compounds of any formula described herein include the compounds themselves, as well as their salts, and their solvates, if applicable. A salt, for example, can be formed between an anion and a positively charged group (e.g., amino) on a compound of the disclosure. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on a compound of the disclosure. Suitable cations include sodium ion, potassium ion, magnesium ion, calcium ion, and an ammonium cation such as tetramethylammonium ion. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. The compounds of the disclosure also include those salts containing quaternary nitrogen atoms.

Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Additionally, the compounds of the present disclosure, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc. "Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hydrate refers to, for example, a mono-hydrate, a di-hydrate, a tri-hydrate, etc.

In addition, a crystal polymorphism may be present for the compounds or salts thereof represented by the formulae disclosed herein. It is noted that any crystal form, crystal form mixture, or anhydride or hydrate thereof, is included in the scope of the present disclosure.

The sections that follow provide a description of ADCs that can be administered to a human patient to treat or prevent rejection of an allogeneic cell therapy as well as methods of administering such therapeutics to the patient.

II. Allogeneic Cell Treatment Methods

In immune-competent hosts, transplanted allogeneic cells are often rapidly rejected. Such rejection is commonly referred to as host versus graft (HvG) rejection. One challenge of allogeneic cell therapy is identifying a means by which the allogeneic cells can be accepted by a human recipient. Such acceptance of the allogeneic cells can impact the efficacy of the treatment and also results in adverse side effects to the patient.

Described herein are methods for treating or preventing rejection of allogeneic cells in a human subject by administering an anti-CD137 antibody drug conjugate (ADC) that targets endogenous CD137+ cells, e.g., activated T cells.

In certain embodiments, a priming response is first elicited in the human subject prior to administration of the anti-CD137 ADC. "Priming" of the patient helps to develop activated anti-alloantigen T cells that are produced following administration of allogeneic cells. It is desired that the infusion of allogeneic cells stimulates the patient's immune system to react against the allogeneic cells. A priming amount of an allogeneic cell is administered to the human subject in order to induce a "priming" immune response.

In the priming step, allogeneic cells are administered to the patient, e.g., intravenously, in order to elicit an immune response resulting in endogenous activated CD137+ T cells. Accordingly, a priming dose of allogeneic cells is preferably an amount effective to elicit an immune response comprising activation of endogenous CD137+ T cells. In exemplary embodiments, an effective priming dosage is an aliquot of allogeneic cells for intravenous infusion that is at least about $1\times10^5$ cells/kg, $0.5\times10^6$ cells/kg, about $1\times10^6$ cells/kg, about $1\times10^7$ cells/kg, about $1\times10^8$ allogeneic cells/kg, about $1\times10^9$ allogeneic cells/kg, about $1\times10^{10}$ allogeneic cells/kg, between about $0.5\times10^6$ to about $1\times10^{10}$ cells/kg, between about $0.5\times10^6$ to about $1\times10^8$ cells/kg, between about $1\times10^7$ to about $1\times10^{10}$ cells/kg, between about $1\times10^8$ to about $1\times10^{10}$ cells/kg, or between about $1\times10^9$ to about $1\times10^{10}$ cells/kg. In other exemplary embodiments, the priming dose comprises about $1\times10^5$ to $1\times10^{12}$ allogeneic cells/kg, e.g., $1\times10^5$ to $1\times10^6$ cells/kg, $1\times10^5$ to $1\times10^7$ cells/kg, $1\times10^5$ to $1\times10^8$ cells/kg, $1\times10^5$ to $1\times10^9$ cells/kg, $1\times10^5$ to $1\times10^{10}$ cells/kg, $1\times10^5$ to $1\times10^{11}$ cells/kg, or $1\times10^5$ to $1\times10^{12}$ cells/kg. In other exemplary embodiments, the priming dose of allogeneic cells comprises about $1\times10^6$ to $1\times10^{12}$ cells/kg, $1\times10^7$ to $1\times10^{12}$ cells/kg, $1\times10^8$ to $1\times10^{12}$ cells/kg, $1\times10^9$ to $1\times10^{12}$ cells/kg, $1\times10^{10}$ to $1\times10^{12}$ cells/kg, or $1\times10^{11}$ to $1\times10^{12}$ cells/kg. Doses intermediate to the foregoing ranges are also contemplated for use in the methods of the invention. Dosages of allogeneic cells outside these ranges that can elicit an immune response are also within the scope of this invention.

In one embodiment, the allogeneic cell includes, but is not limited to, an allogeneic T cell or an allogeneic NK cell. In exemplary embodiments, the allogeneic cell expresses a chimeric antigen receptor, as described herein.

Following administration of a priming amount of an allogeneic cell, an anti-CD137 antibody-drug conjugate (ADC) is administered to the human subject. CD137 is expressed on activated T cells. Thus, the anti-CD137 ADC can be used to deplete the number of activated T cells in the human subject prior to administration of an allogeneic cell therapy. Exemplary anti-CD137 antibodies, cytotoxins, and linkers suitable for use in the methods described herein are set forth in detail below.

Following administration of the CD137 ADC, a therapeutically effective amount of an allogeneic cell is administered to the human subject. Selective depletion of the activated T cell population prior to the administration of the allogeneic cell, e.g., an allogeneic cell expressing a CAR, improves the overall efficacy of the allogeneic cell therapy by treating or preventing rejection of the allogeneic cells. A therapeutically effective amount of an allogeneic cell can be an amount effective to achieve a therapeutic benefit in a patient. For example, if an allogeneic cell is used in a treatment for a subject having cancer, a therapeutically effective amount can be an amount effective to treat the cancer, reduce the size or volume of the cancer, reduce one or more symptoms associated with the cancer, induce remission of the cancer, and/or prolong the duration of survival or disease-free survival of the subject having the cancer. In one embodiment a therapeutically effective amount of allogeneic cells is greater than the number of cells administered to the subject during the priming step. In another embodiment, a therapeutically effective amount of allogeneic cells is about equal to the number of cells administered to the subject during the priming step. In another embodiment, a therapeutically effective amount of allogeneic cells is less than the number of cells administered to the subject during the priming step.

In an exemplary embodiment, the therapeutically effective amount of allogeneic cells comprises at least $1\times10^5$ cells/kg, e.g., at least $1\times10^6$ cells/kg, at least $1\times10^7$ cells/kg, at least $1\times10^8$ cells/kg, at least $1\times10^9$ cells/kg, at least $1\times10^{10}$ cells/kg, at least $1\times10^{11}$ cells/kg, at least $1\times10^{12}$ cells/kg, at least $1\times10^{13}$ cells/kg, at least $1\times10^{14}$ cells/kg, at least $1\times10^{15}$ cells/kg, at least $1\times10^{16}$ cells/kg, at least $1\times10^{17}$ cells/kg, or more. In other exemplary embodiments, the therapeutically effective amount of allogeneic cells comprises up to $1\times10^5$ cells/kg, e.g., up to $1\times10^6$ cells/kg, up to $1\times10^7$ cells/kg, up to $1\times10^8$ cells/kg, up to $1\times10^9$ cells/kg, up to $1\times10^{10}$ cells/kg, up to $1\times10^{11}$ cells/kg, up to $1\times10^{12}$ cells/kg, up to $1\times10^{13}$ cells/kg, up to $1\times10^{14}$ cells/kg, up to $1\times10^{15}$ cells/kg, up to $1\times10^{16}$ cells/kg, or up to $1\times10^{17}$ cells/kg. In other exemplary embodiments, the therapeutically effective amount of allogeneic cells comprises $1\times10^5$ to $1\times10^{17}$ cells/kg, e.g., $1\times10^6$ to $1\times10^{17}$ cells/kg, $1\times10^7$ to $1\times10^{17}$ cells/kg, $1\times10^8$ to $1\times10^{17}$ cells/kg, $1\times10^9$ to $1\times10^{17}$ cells/kg, $1\times10^{10}$ to $1\times10^{17}$ cells/kg, $1\times10^{11}$ to $1\times10^{17}$ cells/kg, $1\times10^{12}$ to $1\times10^{17}$ cells/kg, $1\times10^{13}$ to $1\times10^{17}$ cells/kg, $1\times10^{14}$ to $1\times10^{17}$ cells/kg, $1\times10^{15}$ to $1\times10^{17}$ cells/kg, or $1\times10^{16}$ to $1\times10^{17}$ cells/kg. In other exemplary embodiments, the therapeutically effective amount of allogeneic cells comprises $1\times10^5$ to $1\times10^{17}$ cells/kg, e.g., $1\times10^5$ to $1\times10^{16}$ cells/kg, $1\times10^5$ to $1\times10^{15}$ cells/kg, $1\times10^5$ to $1\times10^{14}$ cells/kg, $1\times10^5$ to $1\times10^{13}$ cells/kg, $1\times10^5$ to $1\times10^{12}$ cells/kg, $1\times10^5$ to $1\times10^{11}$ cells/kg, $1\times10^5$ to $1\times10^{10}$ cells/kg, $1\times10^5$ to $1\times10^9$ cells/kg, $1\times10^5$ to $1\times10^8$ cells/kg, $1\times10^5$ to $1\times10^7$ cells/kg, or $1\times10^5$ to $1\times10^6$ cells/kg. In other exemplary embodiments, the therapeutically effective amount of allogeneic cells comprises $1\times10^8$ to $1\times10^{10}$ cells/kg. In other exemplary embodiments, the therapeutically effective amount of allogeneic cells comprises $1\times10^{10}$ to $1\times10^{12}$ cells/kg. In other exemplary embodiments, the therapeutically effective amount of allogeneic cells comprises $1\times10^{12}$ to $1\times10^{14}$ cells/kg.

The allogeneic cell used in the initial priming step of the therapy can be the same type (or similar) to the allogeneic cell that will be administered to the human subject as part of the allogeneic cell therapy. For example, the allogeneic cells used in the priming step can be derived from the same donor as the cells used in the allogeneic cell therapy. In another embodiment, the allogeneic cell used in the priming step can express the same or a similar complement of MHC molecules as the cells used in the allogeneic cell therapy. The complement of MHC molecules on expressed by the priming and/or the therapeutic cells can be naturally occurring, or can be modified, e.g., using genetic engineering. In one embodiment, in allogeneic CAR cell therapy, a non-CAR expressing allogeneic cell that is the same type of allogeneic cell being used in the CAR cell therapy is administered to the human subject to elicit a priming response. In an alternative, the priming response can be elicited with a CAR-expressing allogeneic cell that is the same type of CAR-expressing cell that will be used to treat the patient.

The risk of rejection of an allogeneic cell expressing a CAR can be high following the administration of CAR cell therapies. Anti-CD137 ADCs may be used to selectively target activated T cells in a patient who will be receiving allogeneic CAR cell therapy. In certain embodiments, the methods disclosed herein can be used to inhibit or prevent the rejection of an allogeneic cell expressing a CAR in a human patient.

The anti-CD137 ADC can be administered to the human patient in need thereof prior to, concomitantly with, or following administration of one or more priming dose(s) of the allogeneic cell therapy. In one embodiment, an anti-CD137 ADC is administered to the human patient in need thereof prior to the administration of the priming dose(s) of the allogeneic cell. For example, in some embodiments, the anti-CD137 ADC can be administered up to about 10 days prior to the administration of the priming does(s) of the allogeneic cell, e.g., about 10 days, about 9 days, about 8 days, about 7 days, about 6 days, about 5 days, about 4 days, about 3 days, about 2 days, about 1 day, about 24 hours, about 12 hours, about 6 hours, about 3 hours, about 2 hours, or about 1 hour prior to the administration of the priming does(s) of the allogeneic cell. In some embodiments, an anti-CD137 ADC is administered to the human patient in need thereof about 1 to about 48 hours; about 1 to about 24 hours; about 1 to about 18 hours; about 1 to about 12 hours; about 1 to about 10 hours; about 1 to about 6 hours; about 1 to about 3 hours; about 1 to about 2 hours; about 1 to 2 days; about 1 to 3 days; about 1 to 4 days; about 1 to 7 days; about 1 to 10 days; about 3 to 5 days; about 3 to 7 days; about 3 to 10 days; about 12 hours to about 48 hours; about 12 hours to about 36 hours; etc. prior to the administration of the priming dose(s) of the allogeneic cell.

In another embodiment, an anti-CD137 ADC is administered to the human patient in need thereof concomitantly with the administration of priming dose of the allogeneic cell.

In other embodiments, an anti-CD137 ADC is administered to the human patient in need thereof after the administration of the priming dose(s) of the allogeneic cell. For example, in some embodiments, the anti-CD137 ADC can be administered to the human patient in need thereof after about 1 hour, 4 hours, 6 hours, 10 hors 12 hours, 24 hours (1 day), 36 hours, 48 hours (2 days), 3 days, 4 days, 5 days, 6 days, 7 days, 8 days, 9 days, 10 days, 11 days, 12 days, 13 days, 14 days, 21 days or more following administration of the priming dose(s) of the allogeneic cell. In other embodiments, the anti-CD137 ADC can be administered to the human patient in need thereof after about 1 hour to about 10 days after the administration of the priming dose(s) of the allogeneic cell, e.g., about 1-6 hours; about 1-12 hours; about 12 hours to about 7 days; about 12 hours to about 6 days; about 12 hours to about 5 days; about 12 hours to about 4 days; about 12 hours to about 3 days; about 12 hours to about 2 days; about 12 hours to about 24 hours; about 1 to about 10 days; about 1 to about 9 days; about 1 to about 8 days; about 1 to about 7 days; about 1 to about 6 days; about 1 to about 5 days; about 1 to about 4 days; about 1 to about 3 days; about 1 to about 2 days, about 3 days to about 10 days; about 5 days to about 7 days; etc., after the administration of priming dose(s) of the allogeneic cell.

In one embodiment, a single dose of an anti-CD137 ADC is administered to the human patient either prior to, after, or concomitantly with, administration of the priming dose of the allogeneic cell, where such single dose is sufficient to selectively deplete the population of T cells that are activated in response to the administration of the allogeneic cell.

The anti-CD137 ADC can be administered to the human patient in need thereof prior to, concomitantly with, or following administration of the therapeutically effective amount of the allogeneic cells, e.g., allogeneic cells expressing CARs. In one embodiment, the anti-CD137 ADC is administered before administration of the allogeneic cell expressing a CAR is administered to the human patient in need thereof. In one embodiment, the allogeneic cell therapy is administered to the patient after the anti-CD137 ADC has cleared or substantially cleared from the blood of the patient. In one embodiment, an anti-CD137 ADC is administered to the human patient in need thereof prior to (e.g., about 14 days before, about 13 days before, about 12 days before, about 11 days before, about 10 days before, about 9 days before, about 8 days before, about 7 days before, about 6 days before, about 5 days before, about 4 days before, about 2 days before, or about 1 day before) administration of an allogeneic cell therapy, e.g., a CAR cell therapy. In one embodiment, the anti-CD137 ADC is administered to the human patient in need thereof, about 1 to about 14 days; about 2 to about 13 days; about 3 to about 12 days; about 3 to about 11 days; about 4 to about 10 days; about 5 to about 9 days; about 6 to about 8 days; about 1 to about 13 days; about 1 to about 12 days; about 1 to about 11 days; about 1 to about 10 days; about 1 to about 9 days; about 1 to about 8 days; about 1 to about 7 days; about 1 to about 6 days; about 1 to about 5 days; about 1 to about 4 days; about 1 to about 3 days; or about 1 to about 2 days prior to administration of an allogeneic cell therapy.

In one embodiment, the anti-CD137 ADC is administered to the human patient before the allogeneic cell expressing a CAR, where the anti-CD137 ADC is administered to the human subject about 12 hours to about 14 days before administration of the allogeneic cell expressing a CAR. In one embodiment, the anti-CD137 ADC is administered to the human patient before the allogeneic cell expressing a CAR, where the anti-CD137 ADC is administered to the human subject about 24 hours to about 12 days before administration of the allogeneic cell expressing a CAR. In one embodiment, the anti-CD137 ADC is administered to the human patient before the allogeneic cell expressing a CAR, where the anti-CD137 ADC is administered to the human subject about 1 day to about 10 days before administration of the allogeneic cell expressing a CAR. In one embodiment, the anti-CD137 ADC is administered to the human patient before the allogeneic cell expressing a CAR, where the anti-CD137 ADC is administered to the human subject about 2 days to about 8 days before administration of the allogeneic cell expressing a CAR.

In one embodiment, the anti-CD137 ADC is administered concomitantly with the administration of an allogeneic cell expressing a CAR to the human patient in need thereof.

Following administration of the anti-CD137 ADC, the human patient may be tested to confirm that CD137+ activated T cells have been substantially depleted from the patient prior to initiation of the allogeneic CAR therapy. The level of CD137+ activated T cells may be assayed in a biological sample (e.g., blood) from the human patient following administration of the CD137 ADC and compared to the level of CD137+ activated T cells from a biological sample (of the same source, e.g., blood) prior to administration of the anti-CD137 ADC (but following allogeneic cell priming). A decrease in the number of endogenous CD137+ activated T cells indicates that the anti-CD137 ADC has been effective at decreasing the risk of rejection of an allogeneic (using the same or substantially similar allogeneic cells) CAR therapy. In one embodiment, the level of endogenous CD137+ activated T cells in a biological sample from the human patient is reduced by at least about 50%, at least about 60%, at least about 70%, at least about 80%, at least about 90%, at least about 91%, at least about 92%, at least about 93%, at least about 94%, at least about 95%, at least about 96%, at least about 97%, at least about 98%, or at least about 99% relative to the level of CD137+ activated T cells in a biological sample (same type, e.g., blood) from the human patient just prior to administration of the anti-CD137 ADC. In one embodiment, the level of endogenous CD137+ activated T cells is determined one day or less prior to administration of the anti-CD137 ADC.

Alternatively, overall levels of T cells in a biological sample from a human patient can be tested following administration of an anti-CD137 ADC (following allogeneic cell priming), wherein a decrease in the overall number of T cells in a human patient following administration of the anti-CD137 ADC relative to the level prior to administration indicates efficacy of the anti-CD137 ADC for preventing rejection of the allogeneic cell therapy. In one embodiment, the level of endogenous T cells in a biological sample from the human patient is reduced by at least about 5%, at least about 10%, at least about 15%, at least about 20%, relative to the level of T cells in a biological sample (of the same type, e.g., blood) from the human patient just prior to administration of the anti-CD137 ADC. In one embodiment, the level of endogenous T cells in a biological sample from the human patient is reduced by about 5% to 25%, by about 5% to 20%, by about 5% to 15%, or by about 5% to 10%, relative to the level of T cells in a biological sample (of the same type, e.g., blood) from the human patient just prior to administration of the anti-CD137 ADC. In one embodiment, the level of endogenous T cells is determined one day or less prior to administration of the anti-CD137 ADC.

Levels of T cells, including CD137+ activated T cells, can be determined according to standard methods known in the art, including, but not limited, to an in vitro antigen stimulation assay, wherein the number of activated allo-antigen T cells following exposure to an allogeneic cell is compared to the number of activated allo-antigen T cells following exposure to an allogeneic cell in the presence of the anti-CD137 ADC.

The methods disclosed herein can be used to deliver allogeneic cells expressing CARs to a subject. Importantly, the anti-CD137 ADC conditioning methods described herein are useful for expanding the type of immune cell that can be used in CAR therapy by providing a means by which tolerance of an allogeneic cell can be provided. In one embodiment, the CAR expressing allogeneic cell includes, but is not limited to, an allogeneic T cell or an allogeneic NK cell.

In one embodiment, the anti-CD137 antibody-drug conjugate is used to deplete CD137 expressing T cells, e.g., activated T cells expressing CD137, by administering the anti-CD137 antibody-drug conjugate prior to, concomitant with, or after the administration of the priming dose of an allogeneic cell. In particular, an anti-CD137 ADC can be used to deplete host-reactive T cells (activated T cells following priming) The methods disclosed herein are particularly useful for the treatment of cancer or an autoimmune disease in a human subject having one of these disorders.

In one embodiment, the methods disclosed herein are used to treat cancer. Examples of the types of cancer that can be treated using the methods disclosed herein include, but are not limited to, adult advanced cancer, pancreatic cancer, non-resectable pancreatic cancer, colorectal cancer, metastatic colorectal cancer, ovarian cancer, triple-negative breast cancer, hematopoietic/lymphoid cancer, colon cancer liver metastasis, small cell lung cancer, non-small cell lung cancer, B-cell lymphoma, relapsed or refractory B-cell lymphoma, follicular lymphoma, mantle cell lymphoma, diffuse large cell lymphoma, relapsed or refractory diffuse large cell lymphoma, anaplastic large cell lymphoma, primary mediastinal B-cell lymphoma, recurrent mediastinal, refractory mediastinal large B-cell lymphoma, large B-cell lymphoma, Hodgkin lymphoma, non-Hodgkin lymphoma, relapsed or refractory non-Hodgkin lymphoma, refractory aggressive non-Hodgkin lymphoma, B-cell non-Hodgkin lymphoma, refractory non-Hodgkin lymphoma, colorectal carcinoma, gastric carcinoma, pancreatic carcinoma, triple-negative invasive breast carcinoma, renal cell carcinoma, lung squamous cell carcinoma, hepatocellular carcinoma, urothelial carcinoma, leukemia, B-cell leukemia, B-cell acute lymphocytic leukemia, B-cell acute lymphoblastic leukemia, adult acute lymphoblastic leukemia, B-cell prolymphocytic leukemia, childhood acute lymphoblastic leukemia, refractory childhood acute lymphoblastic leukemia, acute leukemia, acute lymphoblastic leukemia, acute lymphocytic leukemia, prolymphocytic leukemia, chronic lymphocytic leukemia, acute myeloid leukemia, recurrent plasma cell myeloma, refractory plasma cell myeloma, multiple myeloma, relapsed or refractory multiple myeloma, multiple myeloma of bone, malignant glioma of brain, myelodysplastic syndrome, EGFR-positive colorectal cancer, glioblastoma multiforme, neoplasms, blastic plasmacytoid dendritic cell neoplasms, liver metastases, solid tumors, advanced solid tumors, mesothelin positive tumors, hematological malignancies, and other advanced malignancies.

In one embodiment, the methods disclosed herein are used to treat an autoimmune disease. More specifically, an anti-CD137 ADC is administered to a human subject having an autoimmune disease in combination with allogeneic cell therapy, e.g., an allogeneic cell expressing a CAR. Examples of autoimmune diseases that can be treated using the combination methods disclosed herein include, but are not limited to, multiple sclerosis, Crohn's disease, ulcerative colitis, rheumatoid arthritis, type 1 diabetes, lupus, and psoriasis.

In certain embodiments, an anti-CD137 ADC is administered to a human patient in combination with a CAR-T cell therapy. In one embodiment, the anti-CD137 ADC is administered to the human patient prior to administration of the CAR-T therapy.

Examples of CAR-T constructs that could be expressed in allogeneic cells and used with the methods disclosed herein, include, but are not limited to, CD19 CAR-T (e.g., CART-19-01,02,03 (Fujian Medical University); daopeicart (Hebei Senlang Biotechnology Inc.); IM19CART/001, YMCART201702 (Beijing Immunochina Medical Science & Technology Co.); CART-CD19-02,03 (Wuhan Sian Medical Technology Co.); Universal CD19-CART/SHBYCL001, 002 (Shanghai Bioray Laboratory Inc.); Unicar-Therapy201701 (Shanghai Unicar-Therapy Biomedicine Technology Co.); Genechem/NCT02672501 (Shanghai GeneChem Co.); SenL_19 (Hebei Senlang Biotechnology Inc.); PCAR-019 (PersonGen BioTherapeutics (Suzhou); ICAR19 (Immune Cell, Inc.); WM-CART-02 (Sinobioway Cell Therapy Co.); HenanCH080,109,152 (Henan Cancer Hospital/The Pregene (ShenZhen) Biotechnology Co.); IM19-CD28 and IM19-41BB CAR-T cells (Beijing Immunochina Medical Science & Technology Company); CTL019/IT1601-CART19 (Beijing Sanwater Biological Technology Co.); CTL019/CCTL019C2201 (Novartis Pharmaceuticals); CD19:4-1BB:CD28:CD3/FirstShenzhen01 (Shenzhen Second People's Hospital/The Beijing Pregene Science and Technology Company); MB-CART19.1 (Shanghai Children's Medical Center/Miltenyi Biotec GmbH); PZ01 CAR-T cells (Pinze Lifetechnology Co.); YMCART201701 (Beijing Immunochina Medical Science & Technology Co.); 2016YJZ12 (Peking University/Marino Biotechnology Co.); EGFRt/19-28z/4-1BBL CAR T cells (Memorial Sloan Kettering Cancer Center/Juno Therapeutics, Inc.); Doing-002 (Beijing Doing Biomedical Co.); PCAR-019 (PersonGen BioTherapeutics (Suzhou) Co.); C-CAR011 (Peking Union Medical College Hospital/Cellular Biomedicine Group Ltd.); iPD1 CD19 eCAR T cells (Peking University/Marino Biotechnology Co.); 2013-1018/ NCT02529813 (M. D. Anderson Cancer Center/Ziopharm/ Intrexon Corp.); HenanCH CAR 2-1 (Henan Cancer Hospital/The Pregene (ShenZhen) Biotechnology Co.); JCAR015 (Juno Therapeutics, Inc.); JCAR017/017001,004, 006 (Juno Therapeutics, Inc.); JCAR017 (Celgene); TBI-1501 (Takara Bio Inc.); JMU-CD19CAR (Jichi Medical University); KTE-C19 (Kite, A Gilead Company); TriCAR-T-CD19 (Timmune Biotech Inc.); Pε-05175157 (Fred Hutchinson Cancer Research Center)); CD22/CD30/CD7/ BCMA/CD123 (e.g., 2016040/NCT03121625 (Hebei Senlang Biotechnology Inc.)); CD22 (e.g., Ruijin-CAR-01 (Ruijin Hospital/Shanghai Unicar-Therapy Bio-medicine Technology Co.); AUTO-PA1, DB1 (Autolus Limited)), CD20 (e.g., Doing-006 (Beijing Doing Biomedical Co.)); or CD20/CD22/CD30 (e.g., SZ5601 (The First Affiliated Hospital of Soochow University Shanghai/Unicar-Therapy Biomedicine Technology Co.)).

Chimeric Antigen Receptors (CARs)

The present invention includes the use of allogeneic cell therapy, e.g., allogeneic CAR cell therapy, in combination with an anti-CD137 immune suppressing ADC to treat or prevent rejection of the allogeneic cells needed for therapy. The invention is not generally limited to a specific CAR construct, e.g., a specific antigen binding region or intracellular signaling domain, as the invention is based, at least in part, on the discovery that anti-CD137 ADCs can serve as a conditioning agent for CAR therapy by promoting acceptance of CAR expressing cells by ablating endogenous CD137+ immune cells, such as endogenous T cells. Specific CARs, e.g., CD19 specific CARs, are contemplated herein and are included in the methods disclosed herein, but are not meant to be limiting.

CAR constructs are known in the art and generally contain (a) an extracellular region comprising an antigen binding domain, (b) a transmembrane domain and (c) a cytoplasmic signaling domain. Exemplary CAR configurations are known in the art, and any suitable configuration can be used in the methods described herein. For example, the CAR may be a first generation, a second generation, or a third generation CAR, e.g., as described in Guedan et al. *Molecular Therapy-Methods & Clinical Development*. 12: 145-156 (2019) or Sadelain et al. *Cancer discovery* 3.4: 388-398 (2013), the entire contents of which are hereby incorporated by reference. Briefly, a "first generation" CAR can comprise an (a) extracellular antigen binding domain, (b) a transmembrane domain, (c) one or more intracellular signaling domains, and optionally (d) a hinge region connecting the antigen binding domain to the transmembrane domain. A "second generation" CAR can comprise elements (a), (b), (c), and optionally (d), and further includes a co-stimulatory domain, for example, a co-stimulatory domain of CD28 or 4-1BB. A "third generation" CAR can comprise elements (a), (b), (c), and optionally (d), and further includes multiple co-stimulatory domains, for example, the co-stimulatory domains of CD28 and 4-1BB, or the co-stimulatory domains of CD28 and OX40. Each of the foregoing elements is described in detail below. It should be appreciated that in some embodiments, CAR molecules described by the following exemplary, non-limiting arrangements are from left to right, N-terminus to C-terminus of the CAR. A CAR as described by the disclosure may comprise or further comprise any other combination of elements as described herein. Other exemplary chimeric antigen receptor constructs are disclosed in U.S. Pat. Nos. 9,328,156; 9,783, 591; 9,714,278; 9,765,156; 10,117,896; 9,573,988; 10,308, 717; 10,221,245; 10,040,865; U.S. Patent Publication No. 2018/0256712A1; U.S. Patent Publication No. 2018/ 0271907A1; U.S. Patent Publication No. 2016/0046724A1; U.S. Patent Publication No. 2018/0044424A1; U.S. Patent Publication No. 2018/0258149A1; U.S. Patent Publication No. 2019/0151363A1; and U.S. Patent Publication No. 2018/0273601A1; the contents of each of the foregoing patents and patent publications are incorporated by reference herein in their entirety.

The CAR used in the methods disclosed herein can include an extracellular antigen binding domain. The extracellular antigen binding domain can be any molecule that binds to an antigen, including, but not limited to, a human antibody, a humanized antibody, or any a functional fragment thereof. In certain embodiments, the antigen binding domain is a scFv. In other embodiments, the extracellular antigen binding domain is a non-immunoglobulin scaffold protein. In other embodiments, the extracellular binding domain of the CAR comprises a single chain T cell receptor (scTCR). As described in U.S. Pat. Nos. 5,359,046, 5,686, 281 and 6,103,521, the extracellular domain may also be obtained from any of the wide variety of extracellular domains or secreted proteins associated with ligand binding and/or signal transduction.

The choice of the molecular target (antigen) of the extracellular binding domain depends upon the type and number of ligands that define the surface of a target cell. For example, the antigen binding domain may be chosen to recognize a ligand that acts as a cell surface marker on target cells associated with a particular disease state. Thus, in one aspect, the CAR-mediated immune cell (e.g., T-cell) response can be directed to an antigen of interest by way of engineering an extracellular antigen binding domain that specifically binds a desired antigen into a CAR. For example, the antigen binding domain may be chosen to recognize a ligand that acts as a cell surface marker on target cells associated with a particular disease state, such as cancer or an autoimmune disease. Thus examples of cell surface markers that may act as ligands for the antigen binding domain in a CAR include those associated with cancer cells and other forms of diseased cells, for example, autoimmune disease cells and pathogen infected cells. In some embodiments, a CAR is engineered to target a tumor antigen of interest by way of engineering a desired antigen binding domain that specifically binds to an antigen on a tumor cell. In the context of the present invention, "tumor antigen" refers to antigens that are common to specific hyperproliferative disorders such as cancer. In one embodiment, the antigen is a tumor antigen, examples of which include, but are not limited to, CD19, CD22, CD30, CD7, BCMA, CD137, CD22, CD20, AFP, GPC3, MUC1, mesothelin, CD38, PD1, EGFR (e.g., EGFRvIII), MG7, BCMA, TACI, CEA, PSCA, CEA, HER2, MUC1, CD33, ROR2, NKR-2, PSCA, CD28, TAA, NKG2D, or CD123. In one embodiment, CAR comprises an scFv that binds to CD19, CD22, CD30, CD7, BCMA, CD137, CD22, CD20, AFP, GPC3, MUC1, mesothelin, CD38, PD1, EGFR (e.g., EGFRvIII), MG7, BCMA, TACI, CEA, PSCA, CEA, HER2, MUC1, CD33, ROR2, NKR-2, PSCA, CD28, TAA, NKG2D, or CD123.

In another aspect, the extracellular binding domain of the CAR binds to AFP (e.g., ETCH17AFPCAR01 (Aeon Therapeutics (Shanghai) Co./Eureka Therapeutics Inc.)), GPC3 (e.g., GeneChem GPC-3 CART (Shanghai GeneChem Co.); 302 GPC3-CART (Shanghai GeneChem Co.); CAR-T for liver cancer (Shanghai GeneChem Co.); CAR-GPC3 T cells (Carsgen Therapeutics)), MUC1 (e.g., PG-021-001,002 (PersonGen BioTherapeutics (Suzhou) Co.)), mesothelin (e.g., H2017-01-PO1 (Ningbo Cancer Hospital); TAI-meso-CART (Shanghai GeneChem Co.); K16-4/NCT02930993 (China Meitan General Hospital/Marino Biotechnology Co.)), CD38 (e.g., Anti-CD38 A2 CAR-T/SOR-CART-MM-001 (Sorrento Therapeutics, Inc.)), herinCAR-PD1 (e.g., herinCAR-PD1/NBWYKY2016-06-001,002,003 (Ningbo Cancer Hospital); SIMC-20160101,02,03 (Shanghai International Medical Center)), BCMA (e.g., P-BCMA-101 autologous T stem cell memory (Tscm) CAR-T cells/P-BCMA-101-001 (Poseida Therapeutics, Inc.); HenanCH284 (Henan Cancer Hospital/The Pregene (ShenZhen) Biotechnology Company); LCAR-B38M CAR-T cells (Nanjing Legend Biotech Co.); 9762/NCT03338972 (Fred Hutchinson Cancer Research Center/Juno Therapeutics, Inc.); Descartes-08 (Cartesian Therapeutics); KITE-585 (Kite, A Gilead Company); bb21217 (bluebird bio); bb21217 (Celgene); JCARH125 (Juno Therapeutics, Inc.)), CD30 (e.g., ICAR30 T cells (Immune Cell, Inc.)), EGFR (e.g., EGFR: 4-1BB:CD28:CD3 modified T cells/First Shenzhen02 (Shenzhen Sceond People's Hospital/The Beijing Pregene Science and Technology Company); EGFR-IL12-CART (Shenzhen Second People's Hospital/The Pregene (ShenZhen) Biotechnology Co.); SBNK-2016-015-01 (Beijing Sanbo Brain Hospital/Marino Biotechnology Co.)), MG7 (e.g., MG7-CART (Xijing Hospital/Shanghai GeneChem Co.)), BCMA/TACI (e.g., AUTO2-MM1 (Autolus Limited)), CEA (e.g., 383-74/NCT02416466 (Roger Williams Medical Center/Sirtex Medical)), mesothelin/PSCA/CEA/HER2/MUC1/EGFRvIII (e.g., NCT03267173 (First Affiliated Hospital of Harbin Medical University/Shanghai Unicar-Therapy Bio-medicine Technology Co.)), CD20 (e.g., EY201605-19 (Beijing Biohealthcare Biotechnology Co.)), CD33 (e.g., 2016-0341/NCT03126864 (M. D. Anderson Cancer Center/Intrexon Corp./Ziopharm)), EGFR/BCMA (e.g., EGFRt/BCMA-41BBz CAR T cell (Memorial Sloan Kettering Cancer Center/Juno Therapeutics, Inc.)), ROR2 (e.g., autologous CCT301-38 or CCT301-59 T cells (Shanghai Sinobioway Sunterra Biotech)), NKR-2 (e.g., CYAD-N2T-002,003,004 (Celyad)), PSCA (e.g., BP-012 (Bellicum Pharmaceuticals)), CD28 (e.g., autologous CSR T cells (Beijing Sanbo Brain Hospital/Marino Biotechnology Co.)), TAA (e.g., AMG 119 (Amgen)), NKG2D (e.g., CM-CS1 (Celyad)), or CD123 (e.g., UCART123 (Cellectis S. A.)). The foregoing further provides examples of CARs that bind said antigens (e.g., AMG 119 (Amgen)). These CAR constructs may be used in the methods disclosed herein with an anti-CD137 ADC.

A CAR construct can further contain a transmembrane domain that connects (either literally or by general proximity, e.g., with spacers) the extracellular antigen binding domain to a cytoplasmic signaling domain. In some embodiments, the extracellular antigen binding domain (e.g., a scFv, Fab or other antigen binding moiety) of a CAR can be linked to a transmembrane domain using a hinge or other linker. A spacer, linker, or hinge can be introduced between the extracellular antigen binding domain and the transmembrane domain to provide the flexibility to allow the antigen-binding domain to orient in different directions, thereby facilitating antigen recognition and binding. The cytoplasmic side of the transmembrane domain can be attached to an intracellular signaling domain, such as the intracellular signaling domain of CD28 or CD3 zeta (CD3-ξ), and can additionally include one or more co-stimulatory domains as discussed below.

Thus, in certain embodiments, the CAR can further comprise a hinge region positioned between the extracellular antigen binding domain and the transmembrane domain. For example, the hinge region can be derived from the hinge region of IgG1, IgG2, IgG3, IgG4, IgA, IgD, IgE, IgM, CD28, or CD8 alpha. In one particular embodiment, the hinge region is derived from the hinge region of IgG4. In another embodiment, the hinge region is a CD8 hinge domain (see SwissProt/GenBank Acc. No. P01732).

In one embodiment, a CAR comprises an extracellular antigen binding domain and a transmembrane domain connected via a CD8 hinge:

```
                                          (SEQ ID NO: 2)
AKPTTTPAPR PPTPAPTIAS QPLSLRPEAC RPAAGGAVHT
RGLDFA.
```

In one embodiment, a CAR comprises an extracellular antigen binding domain and a transmembrane domain connected via a hybrid CD8-CD28 hinge:

```
                                          (SEQ ID NO: 3)
AKPTTTPAPR PPTPAPTIAS QPLSLRPEAC RPAAGGAVHT
RGLDFAPRKI EVMYPPPYLD NEKSNGTIIH VKGKHLCPSP
LFPGPSKP.
```

The transmembrane domain may be derived from the sequence of a protein contributing the extracellular antigen binding domain, a protein contributing the effector function signaling domain, a protein contributing the proliferation signaling portion, or by a totally different protein. In some embodiments, the transmembrane domain is naturally associated with one of the other domains of the CAR. For example, the transmembrane domain and the cytoplasmic domain can be derived from the transmembrane region and the cytoplasmic region of the same protein. In one embodiment, the transmembrane and cytoplasmic domains of the CAR comprise contiguous portions of the CD28 sequence. Any transmembrane domain may be used in the CAR constructs described herein, provided that the domain is capable of anchoring a CAR comprising the antigen binding domain to a cell membrane.

The transmembrane domain may be derived either from a natural or from a synthetic source. Where the source is natural, the domain may be derived from any membrane-bound or transmembrane protein. Exemplary transmembrane domains that can be used in the methods provided herein may be derived from (e.g., comprise at least the transmembrane domain(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, LFA-1 T-cell co-receptor, CD2 T-cell co-receptor/adhesion molecule, CD8 alpha, and fragments thereof. The transmembrane domain of a protein can be identified using any method known in the art, e.g., hydrophobicity analysis, structural analysis, etc., or by using public databases, e.g., the UniProt Database.

In some embodiments, the transmembrane domain may be synthetic. In exemplary embodiments, the transmembrane domain can comprise predominantly hydrophobic residues such as leucine and valine. In one embodiment, a triplet of phenylalanine, tryptophan and valine can be positioned at each end of a synthetic transmembrane domain. Optionally, a short oligo- or polypeptide linker, preferably between 2 and 10 amino acids in length, may form the linkage between the transmembrane domain and the cytoplasmic signaling domain of a CAR. A glycine-serine doublet provides a particularly suitable linker.

In some embodiments, the transmembrane domain in the CAR used herein is the CD8 transmembrane domain, or a portion thereof. Sequences of CD8 for this purpose are taught in PCT Publication No. WO2014/055771A1.

In some embodiments, the transmembrane domain in the CAR is the CD8 transmembrane domain, or a functional portion thereof. For example, a CAR can comprise a CD3 transmembrane domain having an amino acid sequence of LDPKLCYLLD GILFIYGVIL TALFLRVK (SEQ ID NO: 4), or a functional portion thereof, such as LCYLLDGILF IYGVILTALF L (SEQ ID NO: 5).

In some embodiments, the transmembrane domain in the CAR of the invention is a CD28 transmembrane domain. An exemplary sequence of CD28 is provided below, as well as an exemplary transmembrane domain sequence. In some embodiments, the CD28 transmembrane domain comprises the exemplary transmembrane domain sequence below, or a fragment or variant thereof that is capable of anchoring a CAR comprising the sequence to a cell membrane. Thus, in some embodiments, the transmembrane domain of the CAR is a CD28 transmembrane domain containing the following amino acid sequence: FWVLVVVGGVLACYSLL-VTVAFIIFWV (SEQ ID NO: 6). In one embodiment, the transmembrane domain of the CAR is a CD28 transmembrane domain containing the following amino acid sequence:

(SEQ ID NO: 7)
IEVMYPPPYL DNEKSNGTII HVKGKHLCPS PLFPGPSKPF
WVLVVVGGVL ACYSLLVTVA FIIFWV, or a functional fragment thereof, e.g., SEQ ID NO: 6.

In addition to an extracellular antigen binding domain and a transmembrane domain, a CAR further comprises an intracellular (or cytoplasmic) signaling domain.

It is known that signals generated through the endogenous TCR alone are insufficient for full activation of the T cell and that a secondary or co-stimulatory signal may also be required. Thus, T cell activation can be mediated by two distinct classes of cytoplasmic signaling sequences: those that initiate antigen-dependent primary activation through the TCR (primary cytoplasmic signaling sequences) and those that act in an antigen-independent manner to provide a secondary or co-stimulatory signal (secondary cytoplasmic signaling sequences).

An "intracellular signaling domain" or "cytoplasmic signaling domain" as the terms are used herein, refers to an intracellular portion of the CAR. The intracellular signaling domain can generate a signal that promotes an immune effector function of the CAR containing immune allogeneic cell, e.g., a CAR-T cell or CAR-expressing NK cell. Examples of immune effector function, e.g., in a CART cell or CAR-expressing NK cell, include cytolytic activity and helper activity, including the secretion of cytokines. In certain embodiments, the intracellular signal domain transduces the effector function signal and directs the cell to perform a specialized function. While the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

In one embodiment, the intracellular signaling domain of the CAR contains a CD3 zeta signaling region as described in SEQ ID NO: 8, or a signaling portion thereof.

(SEQ ID NO: 8)
RVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATK

DTYDALHMQALPPR.

Cytoplasmic signaling domains further can include, but are not limited to, those derived from CD3 zeta, FcR gamma, FcR beta, CD3 gamma, CD3 delta, CD3 epsilon, CDS, CD22, CD79a, CD79b, CD278 ("ICOS"), Fc.epsilon.RI, CD66d, DAP10, and DAP12.

A CAR may further contain an "intracellular costimulatory domain" which is a polypeptide chain derived from an intracellular signaling domain of a costimulatory protein or proteins, such as CD28 and 4-1BB, that enhance cytokine production. Exemplary co-stimulatory signaling regions include 4-1BB, CD21, CD28, CD27, CD127, ICOS, IL-15Rα, and OX40.

In certain embodiments, the cytoplasmic costimulatory domain of a CAR comprises the 4-1BB signaling domain by itself or combined with any other desired cytoplasmic domain(s) useful in the context of a CAR. 4-1BB is a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank acc no. AAA62478.2, or the equivalent residues from a non-human species, e.g., mouse, rodent, monkey, ape and the like.

In one embodiment, the intracellular costimulatory domain of the CAR is a 4-1BB (CD137) co-stimulatory signaling region, or a signaling portion thereof:

(SEQ ID NO: 9)
KRGRKKLLYIFKQPFMRPVQTTQEEDGCSCRFPEEEEGGCEL.

In one embodiment, the costimulatory signaling domain of the CAR is a CD28 co-stimulatory signaling region sequence. For example, the costimulatory signaling domain can comprise the following CD28 co-stimulatory signaling region, or a signaling portion thereof:

(SEQ ID NO: 10)
RSKRSRLLHSDYMNMTPRRPGPTRKHYQPYAPPRDFAAYRS.

In exemplary embodiments, the cytoplasmic domain of the CAR can contain a CD3-zeta signaling domain, in combination with any other desired cytoplasmic domain(s) useful in the context of the CAR of the invention. In certain embodiments, the cytoplasmic domain of the CAR can comprise a CD3 zeta domain and a costimulatory signaling region, including, but not limited to, a costimulatory signaling region of 4-1BB, CD28, and/or CD27.

The cytoplasmic signaling sequences within the cytoplasmic signaling portion of the CAR of the invention may be linked to each other in a random or specified order. Optionally, a short oligo- or polypeptide linker or spacer, preferably between 5 and 20 amino acids in length may be inserted between cytoplasmic domains. A GGGGS (SEQ ID NO:27) or (GGGGS)×3 (SEQ ID NO:28) provides a particularly suitable linker.

In one embodiment, a CAR used herein includes an extracellular domain containing a single chain variable domain of an anti-CD19 monoclonal antibody, a transmembrane domain containing a hinge and transmembrane domain of CD8α, and a cytoplasmic domain containing the signaling domain of CD3ξ and the signaling domain of 4-1BB. An exemplary CAR includes an anti-CD19 extracellular domain include the anti-CD19 monoclonal antibody which is described in Nicholson I C, et al., Mol Immunol 34:1157-1165 (1997) plus the 21 amino acid signal peptide of CD8α (translated from 63 nucleotides at positions 26-88 of GenBank Accession No. NM_001768). The CD8α hinge and transmembrane domain consists of 69 amino acids translated from the 207 nucleotides at positions 815-1021 of GenBank Accession No. NM_001768. The CD3ξ signaling domain of the preferred embodiment contains 112 amino acids translated from 339 nucleotides at positions 1022-1360 of GenBank Accession No. NM_000734.

Between the extracellular domain (comprising the antigen binding domain) and the transmembrane domain of the CAR (described above), or between the cytoplasmic domain and the transmembrane domain of the CAR, there may be incorporated a spacer or hinge domain. As used herein, the term "spacer domain" generally means any oligo- or polypeptide that functions to link the transmembrane domain to the extracellular domain and/or the cytoplasmic domain in the polypeptide chain. As used herein, a hinge domain generally means any oligo- or polypeptide that functions to provide flexibility to the CAR, or domains thereof, and/or prevent steric hindrance of the CAR, or domains thereof. In some embodiments, a spacer or hinge domain may comprise up to 300 amino acids, preferably 10 to 100 amino acids and most preferably 5 to 20 amino acids. Often, a spacer or hinge is introduced between the extracellular antigen binding domain and the transmembrane domain to provide flexibility which allows the antigen-binding domain to orient in different directions to facilitate antigen recognition and binding. It also should be appreciated that one or more spacer domains may be included in other regions of a CAR, as aspects of the disclosure are not limited in this respect.

It is to be understood that a CAR can include a region (e.g., an antigen binding domain, a transmembrane domain, a cytoplasmic domain, a signaling domain, a safety domain, and/or a linker, or any combination thereof) having a sequence provided herein or a variant thereof or a fragment of either one thereof (e.g., a variant and/or fragment that retains the function required for the CAR activity) can be included in a CAR protein as described herein. In some embodiments, a variant has 1, 2, 3, 4, 5, 6, 7, 8, 9, or 10 amino acid changes relative to the illustrated sequence. In some embodiments, a variant has a sequence that is at least 80%, at least 85%, at least 90%, 90%-95%, at least 95% or at least 99% identical to the illustrated sequence. In some embodiments, a fragment is 1-5, 5-10, 10-20, 20-30, 30-40, or 40-50 amino acids shorter than a sequence provided herein. In some embodiments, a fragment is shorter at the N-terminal, C-terminal, or both terminal regions of the sequence provided. In some embodiments, a fragment contains 80%-85%, 85%-90%, 90%-95%, or 95%-99% of the number of amino acids in a sequence provided herein.

In other embodiments, the invention comprises nucleic acid sequences that encode for the amino acid sequences disclosed herein.

In some embodiments, the above exemplary, non-limiting arrangements are from left to right, N-terminus to C-terminus of the CAR. The CAR may comprise or further comprise any other combination of elements as described herein.

Once the CAR construct is identified with its various parts, a CAR expressing immune cell is produced whereby the immune cell expresses the CAR. The method includes introducing into, e.g., transducing, the immune cell with a nucleic acid molecule described herein (e.g., an RNA molecule, e.g., an mRNA), or a vector comprising a nucleic acid molecule encoding a CAR, e.g., a CAR described herein. The present invention also provides a method of generating a population of cells (e.g., RNA-engineered cells transiently expressing an exogenous RNA). The method includes introducing into the cell an RNA as described herein (e.g., an in vitro transcribed RNA or synthetic RNA; an mRNA sequence encoding a CAR polypeptide as described herein). In embodiments, the RNA expresses the CAR polypeptide transiently. In one embodiment, the cell is a cell as described herein, e.g., an immune effector cell (e.g., T cells or NK cells, or cell population).

Anti-CD137 Antibody Drug Conjugates (ADCs)

As described herein, anti-CD137 ADCs can be used in combination with allogeneic cell therapy to treat cancer or an autoimmune disease in a human patient. More specifically, anti-CD137 ADCs can be used to deplete CD137+ cells (e.g., CD137+ T cells) in a human subject who is also receiving allogeneic cell therapy. Anti-CD137 ADCs target endogenous T cells and kill these cells such that the patient's immune system will not attack the allogeneic cell therapy (e.g., an allogeneic cell expressing a CAR) administered to the subject. Thus, anti-CD137 ADCs are used in combination with CAR therapy to prevent or reduce the risk of rejection of the cell therapy in the recipient patient. One advantage of using anti-CD137 ADCs as a conditioning regimen is that activated T cells expressing CD137 can be specifically targeted for depletion.

Anti-CD137 Antibodies

The present invention is based in part on the discovery that antibodies, and antigen-binding fragments thereof, capable of binding CD137 (also referred to as CDw 137, TNFRSF9, 4-1BB, and ILA) can be used as therapeutic agents to prevent or reduce the risk of rejection of a cell therapy in a patient in need of a cell therapy.

T cells have been shown to express CD137, as this antigen is a transmembrane TNF receptor superfamily of costimulatory molecules and is expressed on a variety of hematopoietic cells and promotes T cell activation and regulates proliferation and survival of T cells (see, e.g., Cannons et al., J. Immunol. 167:1313-1324, 2001, the disclosure of which is incorporated herein by reference as it pertains to the expression of CD137 by T cells). The amino acid sequence of human CD137 is provided below:

```
                   (GenBank No. AAX42660.1; SEQ ID NO: 1)
MGNSCYNIVA TLLLVLNFER TRSLQDPCSN CPAGTFCDNN

RNQICSPCPP NSFSSAGGQR TCDICRQCKG VFRTRKECSS

TSNAECDCTP GFHCLGAGCS MCEQDCKQGQ ELTKKGCKDC
```

```
CFGTENDQKR GICRPWTNCS LDGKSVLVNG TKERDVVCGP

SPADLSPGAS SVTPPAPARE PGHSPQIISF FLALTSTALL

FLLFFLTLRF SVVKRGRKKL LYIFKQPFMR PVQTTQEEDG

CSCRFPEEEE GGCEL
```

Antibodies, and antigen-binding fragments thereof, specific for human CD137 can be identified using techniques known in the art and described herein, such as by immunization, computational modeling techniques, and in vitro selection methods, such as the phage display and cell-based display platforms described below.

In one embodiment, an anti-CD137 antibody that may be used in the methods and compositions (including ADCs) described herein is the murine anti-CD137 antibody BBK2 (Thermo Fisher; MS621PABX) or an anti-CD137 antibody comprising antigen binding regions corresponding to the BBK2 antibody. The BBK2 antibody (which may also be referred to as a BBK-2 antibody or an anti-4-1BB antibody), is a mouse monoclonal antibody (IgG1, kappa) that binds to the ectodomain of human 4-1BB recombinant protein (4-1BB is also known as CD137). In certain embodiments, the methods and compositions of the disclosure include an anti-CD137 antibody comprising the binding regions (e.g., the CDRs) of the BBK2 antibody. In another embodiment, the methods and compositions of the disclosure comprise an antibody that competitively inhibits the binding of the BBK2 antibody to its epitope on CD137. In certain embodiments, the anti-CD137 antibody is humanized BBK2 or chimeric BBK2.

In one embodiment, the methods and compositions described herein include a chimeric anti-CD137 (ch-BBK2) antibody comprising the variable heavy and light chain regions of BBK2. In certain embodiments, the chimeric BBK2 antibody is an IgG1 antibody comprising human constant regions. The heavy chain amino acid sequence of ch-BBK2 is described in SEQ ID NO: 11, and the light chain amino acid sequence of ch-BBK2 is described in SEQ ID NO:12. The CDR regions (CDR1, CDR2, and CDR3) of each of the heavy and light chain sequences are described in bold below. The variable regions are italicized.

```
                                    (SEQ ID NO: 11)
QVQLQQPGAELVRPGASVKLSCKASGYTFTSYWINWVKQRPGQGLEWIG

NIYPSDSYTNYNQKFKDKATLTVDKSSNTVYMQLNSPTSEDSAVYYCTR

NGVEGYPHYYAMEYWGQGTSVTVSSASTKGPSVFPLAPSSKSTSGGTAA

LGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQ

PENNYKTTPPVLDSGSFFLYSKLTVDKSRWQQGNVFSCSVMHEALHNH

YTQKSLSLSPGK (SEQ ID NO: 12)
DIQMTQTTSALSASLGDRVTIGCRASQDLSNHLYWYQQKPDGTVKLLIY

YTSRLHSGVPSRFSGSGSGTDYSLTIRNLEQEDVATYFCQQGYTLPYTF
```

```
GGGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

The foregoing CDR regions (and BBK2 antibody) are described in Lee et al. (2002) *European J of Immunogenetics* 29(5):449-452. Thus, in one embodiment, the VH CDR amino acid sequences of anti-CD137 antibody BBK2 (including ch-BBK2) are as follows: SGYTFTSYW (VH CDR1; SEQ ID NO: 13); NIYPSDSYT (VH CDR2; SEQ ID NO: 14) and TRNGVEGYPHYYAME (VH CDR3; SEQ ID NO: 15). The VL CDR amino acid sequences of anti-CD137 antibody BBK2 (including ch-BBK2) are as follows: SQDLSNH (VL CDR1; SEQ ID NO: 16); YYTS (VL CDR2; SEQ ID NO: 17) and CQQGYTLPY (VL CDR3; SEQ ID NO: 18).

Alternatively, the CDR regions of BBK2 can be defined according to Kabat numbering. CDRs as defined by Kabat numbering are described below for each of the heavy and light chain sequences (described in bold below). The variable regions of BBK2 are italicized.

```
                           (ch-BBK2 heavy chain; SEQ ID NO: 11)
QVQLQQPGAELVRPGASVKLSCKASGYTFTSYWINWVKQRPGQGLEWIG

NIYPSDSYTNYNQKFKDKATLTVDKSSNTVYMQLNSPTSEDSAVYYCTR

NGVEGYPHYYAMEYWGQGTSVTVSSASTKGPSVFPLAPSSKSTSGGTAA

LGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPS

VFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQ

PENNYKTTPPVLDSGSFFLYSKLTVDKSRWQQGNVFSCSVMHEALHNH

YTQKSLSLSPGK (ch-BBK2 light chain; SEQ ID NO: 12)
DIQMTQTTSALSASLGDRVTIGCRASQDLSNHLYWYQQKPDGTVKLLIY

YTSRLHSGVPSRFSGSGSGTDYSLTIRNLEQEDVATYFCQQGYTLPYTF

GGGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC
```

Thus, in one embodiment, the VH CDR amino acid sequences of anti-CD137 antibody BBK2 (including ch-BBK2) are as follows: SYWIN (VH CDR1; SEQ ID NO: 19); NIYPSDSYTNYNQKFKD (VH CDR2; SEQ ID NO: 20) and NGVEGYPHYYAMEY (VH CDR3; SEQ ID NO: 21), and the VL CDR amino acid sequences of anti-CD137 antibody BBK2 (including ch-BBK2) are as follows: RASQDLSNHLY (VL CDR1; SEQ ID NO: 23); YTSRLHS (VL CDR2; SEQ ID NO: 24) and QQGYTLPYT (VL CDR3; SEQ ID NO: 25).

The heavy chain variable region of BBK2 is set forth in SEQ ID NO: 22 as

```
QVQLQQPGAELVRPGASVKLSCKASGYTFTSYWINWVKQRPGQGLEWIG

NIYPSDSYTNYNQKFKDKATLTVDKSSNTVYMQLNSPTSEDSAVYYCTR

NGVEGYPHYYAMEYWGQGTSVTVSS.
```

The light chain variable region of BBK2 is set forth in SEQ ID NO: 26 as

```
DIQMTQTTSALSASLGDRVTIGCRASQDLSNHLYWYQQKPDGTVKLLIY

YTSRLHSGVPSRFSGSGSGTDYSLTIRNLEQEDVATYFCQQGYTLPYTF

GGGTKLEIK.
```

Anti-CD137 antibodies (including anti-CD137 ADCs) can comprise the heavy and light chain variable region amino acid sequences as set forth in SEQ ID Nos: 22 and 26, respectively.

In one embodiment, the anti-CD137 antibody, e.g., a chimeric (ch-BBK2) antibody or a humanized BBK2 antibody, comprises a heavy chain variable region comprising a CDR1 comprising the amino acid sequence of SEQ ID NO: 19, a CDR2 comprising the amino acid sequence of SEQ ID NO: 20, and a CDR3 comprising the amino acid sequence of SEQ ID NO: 21; and comprises a light chain variable region comprising a CDR1 comprising the amino acid sequence of SEQ ID NO: 23, a CDR2 comprising the amino acid sequence of SEQ ID NO: 24, and a CDR3 comprising the amino acid sequence of SEQ ID NO: 25.

In one embodiment, the anti-CD137 antibody, e.g., a chimeric (ch-BBK2) antibody or a humanized BBK2 antibody, comprises a heavy chain variable region comprising a CDR1 comprising the amino acid sequence of SEQ ID NO: 13, a CDR2 comprising the amino acid sequence of SEQ ID NO: 14, and a CDR3 comprising the amino acid sequence of SEQ ID NO: 15; and comprises a light chain variable region comprising a CDR1 comprising the amino acid sequence of SEQ ID NO: 16, a CDR2 comprising the amino acid sequence of SEQ ID NO: 17, and a CDR3 comprising the amino acid sequence of SEQ ID NO: 18.

Thus, BBK2, humanized BBK2, or chimeric BBK2 antibodies can be used in the anti-CD137 ADCs and methods described herein. Each of these antibodies can be conjugated to any of the cytotoxin described below using methods known in the art and those described herein.

A variety of other anti-CD137 antibodies are known in the art and are useful in the methods described herein. For example, in certain embodiments, the anti-CD137 antibody is selected from ADG106 (as described in, e.g., WO2019105468, US20190055314, WO2019037711, WO2019036855); AGEN2373 (as described in, e.g., WO2018191502, US20180344870); ATOR-1017 (as described in, e.g., WO2018091740, US20180118841) PE0166 (as described in, e.g., Song et al. AACR 2019, Abstract 2397/21), urelumab (also known as BMS-663513; as described in, e.g., WO2004010947, WO2005035584, US20090068192, U.S. Pat. Nos. 7,659,384, 8,475,790, 8,137,667, US20100183621, U.S. Pat. No. 8,716,452, US20120141494, U.S. Pat. No. 9,382,328, US20140193422, WO2016029073, US20160368998, WO2017181034, US20190062445, Chin et al. *Nature communications*. 9.1 (2018): 4679.; Segal et al. *Clinical Cancer Research*. 23.8 (2017): 1929-1936.); and utomilumab (also known as PF-05082566, MOR-7480.; as described in, e.g., WO2012032433, US20120237498, US20140178368, WO2012145183, WO2015119923, WO2015179236, US20160152722, US20190031765, WO2017130076, Chin et al. *Nature communications*. 9.1 (2018): 4679.; Segal et al. *Clinical Cancer Research*. 24.8 (2018): 1816-1823; Fisher et al. *Cancer Immunology, Immunotherapy*. 61.10 (2012): 1721-1733), each of which is incorporated by reference.

Other anti-CD137 antibodies have been described, for example, in WO2019020774, WO2017077085, US20180327504, US20190099488, US2019006045, US20190015508, WO2019014328, US20190071510, WO2018127787, US20180258177, U.S. Ser. No. 10/174, 122, WO2016110584, WO2018017761, WO2018098370, US20130149301, WO2019027754, WO2018156740, US20160244528, WO2016134358, U.S. Ser. No. 10/233, 251, US20170226215, US20160083474, WO2017049452, US20180282422, WO2015188047, WO2010132389, US20120076722, US20110177104, WO2011031063, US20080305113, US20080008716, U.S. Pat. No. 7,829, 088, US20090041763, WO2006126835, US20030096976, US20030223989, US20060182744, WO1996029348, Söderström et al. *Circulation J*. 81.12 (2017): 1945-1952; Makkouk, et al. *Annals of Oncology* 28.2 (2016): 415-420; Martinez-Forero et al. *J. of Immunology*. 190.12 (2013): 6694-6706; Dubrot et al. *Cancer immunology, immunotherapy*. 59.8 (2010): 1223-1233; each of which is incorporated by reference.

In one embodiment, the anti-CD137 antibody comprises a heavy chain of an anti-CD137 antibody described herein, and a light chain variable region of anti-CD137 antibody described herein. In one embodiment, the anti-CD137 antibody comprises a heavy chain comprising a CDR1, CDR2 and CDR3 of an anti-CD137 antibody described herein, and a light chain variable region comprising a CDR1, CDR2 and CDR3 of an anti-CD137 antibody described herein.

In another embodiment, the antibody, or antigen-binding fragment thereof, comprises a heavy chain variable region that comprises an amino acid sequence having at least 95% identity to an anti-CD137 antibody herein, e.g., at least 95%, 96%, 97%, 98%, 99%, or 100% identity to an anti-CD137 antibody herein. In certain embodiments, an antibody comprises a modified heavy chain (HC) variable region comprising an HC variable domain of an anti-CD137 antibody herein, or a variant thereof, which variant (i) differs from the anti-CD137 antibody in 1, 2, 3, 4 or amino acids substitutions, additions or deletions; (ii) differs from the anti-CD137 antibody in at most 5, 4, 3, 2, or 1 amino acids substitutions, additions or deletions; (iii) differs from the anti-CD137 antibody in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to the anti-CD137 antibody, wherein in any of (i)-(iv), an amino acid substitution may be a conservative amino acid substitution or a non-conservative amino acid substitution; and wherein the modified heavy chain variable region can have an enhanced biological activity relative to the heavy chain variable region of the anti-CD137 antibody, while retaining the CD137 binding specificity of the antibody.

Other anti-CD137 antibodies that can be used in conjunction with a cytotoxin described herein can be identified using techniques known in the art (e.g., hybridoma production). Hybridomas can be prepared using a murine system. Protocols for immunization and subsequent isolation of splenocytes for fusion are known in the art. Fusion partners and procedures for hybridoma generation are also known. Human anti-CD137 antibodies can also be generated in the HuMAb-Mouse® or XenoMouse™. In making anti-CD137 antibodies, the CD137 antigen is isolated and/or purified.

The CD137 antigen may be a fragment of CD137 from the extracellular domain of CD137. Immunization of animals can be performed by any method known in the art. See, e.g., Harlow and Lane, *Antibodies: A Laboratory Manual*, New York: Cold Spring Harbor Press, 1990. Methods for immunizing animals such as mice, rats, sheep, goats, pigs, cattle and horses are well known in the art. See, e.g., Harlow and Lane, supra, and U.S. Pat. No. 5,994,619. The CD137 antigen may be administered with an adjuvant to stimulate the immune response. Adjuvants known in the art include complete or incomplete Freund's adjuvant, RIBI (muramyl dipeptides) or ISCOM (immunostimulating complexes). After immunization of an animal with a CD137 antigen, antibody-producing immortalized cell lines are prepared from cells isolated from the immunized animal. After immunization, the animal is sacrificed and lymph node and/or splenic B cells are immortalized by methods known in the art (e.g., oncogene transfer, oncogenic virus transduction, exposure to carcinogenic or mutating compounds, fusion with an immortalized cell, e.g., a myeloma cell, and inactivating a tumor suppressor gene. See, e.g., Harlow and Lane, supra. Hybridomas can be selected, cloned and further screened for desirable characteristics, including robust growth, high antibody production and desirable antibody characteristics.

Anti-CD137 antibodies can be generated from an isolated nucleic acid molecule that comprises a nucleotide sequence encoding an amino acid sequence of a CD137 binding molecule provided by the present disclosure. The amino acid sequence encoded by the nucleotide sequence may be any portion of an antibody, such as a CDR, a sequence comprising one, two, or three CDRs, a variable region of a heavy chain, variable region of a light chain, or may be a full-length heavy chain or full length light chain. A nucleic acid of the disclosure can be, for example, DNA or RNA, and may or may not contain intronic sequences. Typically, the nucleic acid is a cDNA molecule.

In some embodiments, the anti-CD137 antibody (or fragment thereof) has a defined serum half-life. For example, an anti-CD137 antibody (or fragment thereof) may have a serum half-life of about 1-24 hours in the human patient. ADCs containing such anti-CD137 antibodies can also, for example, have a serum half-life of about 1-24 hours in a human patient. Pharmacokinetic analysis by measurement of serum levels can be performed by assays known in the art.

Antibodies for use in conjunction with the ADCs described herein include variants of those antibodies described above, such as antibody fragments that contain or lack an Fc domain, containing one or more, or all, of the CDRs or equivalent regions thereof of an antibody, antibody fragment, described herein.

Methods of Identifying Antibodies

Methods for high throughput screening of libraries of antibodies, antibody fragments, capable of binding CD137 can be used to identify and affinity mature agents that are, for example, useful for treating or preventing rejection of an allogeneic cell therapy. Such methods include in vitro display techniques known in the art, such as phage display, bacterial display, yeast display, mammalian cell display, ribosome display, mRNA display, and cDNA display, among others. The use of phage display to isolate antibodies, or antigen-binding fragments, that bind biologically relevant molecules has been reviewed, for example, in Felici et al., Biotechnol. Annual Rev. 1:149-183, 1995; Katz, Annual Rev. Biophys. Biomol. Struct. 26:27-45, 1997; and Hoogenboom et al., Immunotechnology 4:1-20, 1998, the disclosures of each of which are incorporated herein by reference as they pertain to in vitro display techniques. Randomized combinatorial peptide libraries have been constructed to select for polypeptides that bind cell surface antigens as described in Kay, Perspect. Drug Discovery Des. 2:251-268, 1995 and Kay et al., Mol. Divers. 1:139-140, 1996, the disclosures of each of which are incorporated herein by reference as they pertain to the discovery of antigen-binding molecules. Proteins, such as multimeric proteins, have been successfully phage-displayed as functional molecules (see, for example, EP 0349578; EP 4527839; and EP 0589877, as well as Chiswell and McCafferty, Trends Biotechnol. 10:80-84 1992, the disclosures of each of which are incorporated herein by reference as they pertain to the use of in vitro display techniques for the discovery of antigen-binding molecules. In addition, functional antibody fragments, such as Fab and scFv fragments, have been expressed in in vitro display formats (see, for example, McCafferty et al., Nature 348:552-554, 1990; Barbas et al., Proc. Natl. Acad. Sci. USA 88:7978-7982, 1991; and Clackson et al., Nature 352:624-628, 1991, the disclosures of each of which are incorporated herein by reference as they pertain to in vitro display platforms for the discovery of antigen-binding molecules). Human anti-CD137 antibodies can also be generated, for example, in the HuMAb-Mouse® or XenoMouse™. These techniques, among others, can be used to identify and improve the affinity of antibodies, or antibody fragments, that bind CD137 and that can in turn be used to deplete hematopoietic cells in a patient.

In addition to in vitro display techniques, computational modeling techniques can be used to design and identify anti-CD137 antibodies, or antibody fragments in silico, for instance, using the procedures described in US 2013/0288373, the disclosure of which is incorporated herein as it pertains to molecular modeling methods for identifying anti-CD137 antibodies. For example, using computational modeling techniques, one of skill in the art can screen libraries of antibodies, or antibody fragments, in silico for molecules capable of binding specific epitopes on CD137, such as extracellular epitopes of CD137.

Additional techniques can be used to identify antibodies, or antibody fragments, that bind CD137 on the surface of a cell (e.g., a T cell) and that are internalized by the cell, for instance, by receptor-mediated endocytosis. For example, the in vitro display techniques described above can be adapted to screen for antibodies, or antibody fragments, that bind CD137 on the surface of a hematopoietic stem cell and that are subsequently internalized. Phage display represents one such technique that can be used in conjunction with this screening paradigm. To identify anti-CD137 antibodies, or antibody fragments, that bind CD137 and are subsequently internalized by hematopoietic stem cells, one of skill in the art can use the phage display techniques described in Williams et al., Leukemia 19:1432-1438, 2005, the disclosure of which is incorporated herein by reference in its entirety. For example, using mutagenesis methods known in the art, recombinant phage libraries can be produced that encode antibodies, antibody fragments, such as scFv fragments, Fab fragments, diabodies, triabodies, and $^{10}$Fn3 domains, among others, or ligands that contain randomized amino acid cassettes (e.g., in one or more, or all, of the CDRs or equivalent regions thereof or an antibody or antibody fragment). The framework regions, hinge, Fc domain, and other regions of the antibodies or antibody fragments may be designed such that they are non-immunogenic in humans, for instance, by virtue of having human germline antibody sequences or sequences that exhibit only minor variations relative to human germline antibodies.

Using phage display techniques described herein or known in the art, phage libraries containing randomized antibodies, or antibody fragments, covalently bound to the phage particles can be incubated with CD137 antigen, for instance, by first incubating the phage library with blocking agents (such as, for instance, milk protein, bovine serum albumin, and/or IgG so as to remove phage encoding antibodies, or antibody fragments, that exhibit non-specific protein binding and phage that encode antibodies or fragments thereof that bind Fc domains, and then incubating the phage library with a population of hematopoietic stem cells, which are CD137+. The phage library can be incubated with the hematopoietic stem cells for a time sufficient to allow CD137 specific antibodies, or antibody fragments, to bind cell-surface CD137 and to subsequently be internalized by the hematopoietic stem cells (e.g., from 30 minutes to 6 hours at 4° C., such as 1 hour at 4° C.). Phage containing antibodies, or antibody fragments, that do not exhibit sufficient affinity for CD137 so as to permit binding to, and internalization by, hematopoietic stem cells can subsequently be removed by washing the cells, for instance, with cold (4° C.) 0.1 M glycine buffer at pH 2.8. Phage bound to antibodies, or antibody fragments, that have been internalized by the hematopoietic stem cells can be identified, for instance, by lysing the cells and recovering internalized phage from the cell culture medium. The phage can then be amplified in bacterial cells, for example, by incubating bacterial cells with recovered phage in 2xYT medium using methods known in the art. Phage recovered from this medium can then be characterized, for instance, by determining the nucleic acid sequence of the gene(s) encoding the antibodies, or antibody fragments, inserted within the phage genome. The encoded antibodies, or antibody fragments, can subsequently be prepared de novo by chemical synthesis (for instance, of antibody fragments, such as scFv fragments) or by recombinant expression (for instance, of full-length antibodies).

The internalizing capacity of the prepared antibodies, or antibody fragments, can be assessed, for instance, using radionuclide internalization assays known in the art. For example, anti-CD137 antibodies, or antibody fragments, identified using in vitro display techniques described herein or known in the art can be functionalized by incorporation of a radioactive isotope, such as $^{18}F$, $^{75}Br$, $^{77}Br$, $^{122}I$, $^{123}I$, $^{124}I$, $^{125}I$, $^{129}I$, $^{131}I$, $^{211}At$, $^{67}Ga$, $^{111}In$, $^{99}Tc$, $^{169}Yb$, $^{186}Re$, $^{64}Cu$, $^{67}Cu$, $^{177}Lu$, $^{77}As$, $^{72}As$, $^{86}Y$, $^{90}Y$, $^{89}Zr$, $^{212}Bi$, $^{213}Bi$, or $^{225}Ac$. For instance, radioactive halogens, such as $^{18}F$, $^{75}Br$, $^{77}Br$, $^{122}I$, $^{123}I$, $^{124}I$, $^{125}I$, $^{129}I$, $^{131}I$, $^{211}At$, can be incorporated into antibodies, or antibody fragments, using beads, such as polystyrene beads, containing electrophilic halogen reagents (e.g., Iodination Beads, Thermo Fisher Scientific, Inc., Cambridge, MA). Radiolabeled antibodies, fragments thereof, or ADCs, can be incubated with hematopoietic stem cells for a time sufficient to permit internalization (e.g., from 30 minutes to 6 hours at 4° C., such as 1 hour at 4° C.). The cells can then be washed to remove non-internalized antibodies or fragments thereof, (e.g., using cold (4° C.) 0.1 M glycine buffer at pH 2.8). Internalized antibodies, or antibody fragments, can be identified by detecting the emitted radiation (e.g., γ-radiation) of the resulting hematopoietic stem cells in comparison with the emitted radiation (e.g., γ-radiation) of the recovered wash buffer. The foregoing internalization assays can also be used to characterize ADCs.

Antibodies may be produced using recombinant methods and compositions, e.g., as described in U.S. Pat. No. 4,816,567. In one embodiment, isolated nucleic acid encoding an anti-CD137 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-CLL-1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CD137 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in E. coli.) After expression, the antibody may be isolated from the bacterial cell paste in a soluble fraction and can be further purified.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp.

255-268 (2003). In one embodiment, the host cell is eukaryotic, e.g. a Chinese Hamster Ovary (CHO) cell or lymphoid cell (e.g., Y0, NS0, Sp20 cell).

Cytotoxins

Various cytotoxins can be conjugated to an anti-CD137 antibody via a linker for use in the combination therapies described herein. In particular, the anti-CD137 ADCs include an antibody (or an antigen-binding fragment thereof) conjugated (i.e., covalently attached by a linker) to a cytotoxic moiety (or cytotoxin). As used herein, the terms "cytotoxin", "cytotoxic moiety", and "drug" are used interchangeably. In various embodiments, the cytotoxic moiety exhibits reduced or no cytotoxicity when bound in a conjugate, but resumes cytotoxicity after cleavage from the linker. In various embodiments, the cytotoxic moiety maintains cytotoxicity without cleavage from the linker. In some embodiments, the cytotoxic molecule is conjugated to a cell internalizing antibody, or antigen-binding fragment thereof as disclosed herein, such that following the cellular uptake of the antibody, or fragment thereof, the cytotoxin may access its intracellular target and, e.g., mediate T cell death.

ADCs of the present invention therefore may be of the general Formula I, wherein an antibody or antigen-binding fragment thereof (Ab) is conjugated (covalently linked) to linker (L), through a chemical moiety (Z), to a cytotoxic moiety ("drug," D), $$Ab\text{-}(Z\text{-}L\text{-}D)_n \qquad (I).$$

Accordingly, the antibody or antigen-binding fragment thereof may be conjugated to a number of drug moieties as indicated by integer n, which represents the average number of cytotoxins per antibody, which may range, e.g., from about 1 to about 20. Any number of cytotoxins can be conjugated to the antibody, e.g., about 1, about 2, about 3, about 4, about 5, about 6, about 7, or about 8. In some embodiments, n is from 1 to 4. In some embodiments, n is from 1 to 3. In some embodiments, n is about 2. In some embodiments, n is about 1. The average number of drug moieties per antibody in preparations of ADC from conjugation reactions may be characterized by conventional means such as mass spectroscopy, ELISA assay, and HPLC. The quantitative distribution of ADC in terms of n may also be determined. In some instances, separation, purification, and characterization of homogeneous ADC where n is a certain value from ADC with other drug loadings may be achieved by means such as reverse phase HPLC or electrophoresis.

For some anti-CD137 ADCs, n may be limited by the number of attachment sites on the antibody. For example, where the attachment is a cysteine thiol, an antibody may have only one or several cysteine thiol groups, or may have only one or several sufficiently reactive thiol groups through which a linker may be attached. Generally, antibodies do not contain many free and reactive cysteine thiol groups which may be linked to a drug moiety; primarily, cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, higher drug loading, e.g. n>5, may cause aggregation, insolubility, toxicity, or loss of cellular permeability of certain antibody-drug conjugates.

In certain embodiments, fewer than the theoretical maximum number of drug moieties are conjugated to an antibody during a conjugation reaction. An antibody may contain, for example, lysine residues that do not react with the drug-linker intermediate or linker reagent, as discussed below. Only the most reactive lysine groups may react with an amine-reactive linker reagent. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments.

Cytotoxins suitable for use with the compositions and methods described herein include DNA-intercalating agents, (e.g., anthracyclines), agents capable of disrupting the mitotic spindle apparatus (e.g., vinca alkaloids, maytansine, maytansinoids, and derivatives thereof), RNA polymerase inhibitors (e.g., an amatoxin, such as α-amanitin, and derivatives thereof), and agents capable of disrupting protein biosynthesis (e.g., agents that exhibit rRNA N-glycosidase activity, such as saporin and ricin A-chain), among others known in the art.

In some embodiments, the cytotoxin is a microtubule-binding agent (for instance, maytansine or a maytansinoid), an amatoxin, pseudomonas exotoxin A, deBouganin, diphtheria toxin, saporin, an auristatin, an anthracycline, a calicheamicin, irinotecan, SN-38, a duocarmycin, a pyrrolobenzodiazepine, a pyrrolobenzodiazepine dimer, an indolinobenzodiazepine, an indolinobenzodiazepine dimer, or a variant thereof, or another cytotoxic compound described herein or known in the art.

In some embodiments, the cytotoxin of the antibody-drug conjugate is an RNA polymerase inhibitor. In some embodiments, the RNA polymerase inhibitor is an amatoxin or derivative thereof. In some embodiments, the cytotoxin of the antibody-drug conjugate as disclosed herein is an amatoxin or derivative thereof, such as an α-amanitin, β-amanitin, γ-amanitin, ε-amanitin, amanin, amaninamide, amanullin, amanullinic acid, proamanullin or a derivative thereof.

Additional details regarding cytotoxins that can be used in the anti-CD137 ADCs useful in the methods of the invention are described below.

Amatoxins

In some embodiments, the RNA polymerase inhibitor is an amatoxin or derivative thereof. In some embodiments, the cytotoxin of the antibody-drug conjugate as disclosed herein is an amatoxin or derivative thereof, such as an α-amanitin, β-amanitin, γ-amanitin, ε-amanitin, amanin, amaninamide, amanullin, amanullinic acid, proamanullin or a derivative thereof. Structures of the various naturally occurring amatoxins are represented by Formula II and accompanying Table 1, and are disclosed in, e.g., Zanotti et al., Int. J. Peptide Protein Res. 30, 1987, 450-459.

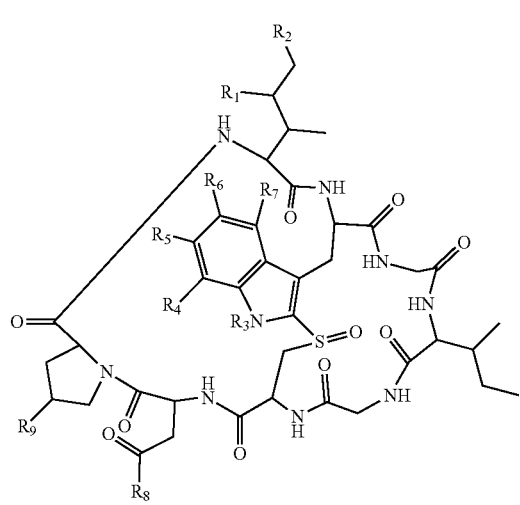

(II)

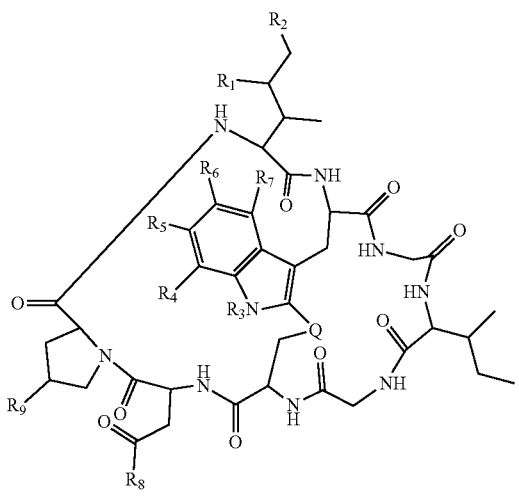

TABLE 1

| Amatoxin structure table. | | | | | | | |
|---|---|---|---|---|---|---|---|
| Name | $R_1$ | $R_2$ | $R_3$, $R_4$ | $R_5$ | $R_6$, $R_7$ | $R_8$ | $R_9$ |
| α-amanitin | OH | OH | H | OH | H | $NH_3$ | OH |
| β-amanitin | OH | OH | H | OH | H | OH | OH |
| γ-amanitin | OH | H | H | OH | H | $NH_3$ | OH |
| ε-amanitin | OH | H | H | OH | H | OH | OH |
| Amanin | OH | OH | H | H | H | OH | OH |
| Amaninamide | OH | OH | H | H | H | $NH_3$ | OH |
| Amanullin | H | H | H | OH | H | $NH_3$ | OH |
| Amanullinic acid | H | H | H | OH | H | OH | OH |
| Proamanullin | H | H | H | OH | H | $NH_3$ | H |

In one embodiment, the cytotoxin is an amanitin or derivative thereof. In one embodiment, the cytotoxin is an α-amanitin or derivative thereof.

Many positions on amatoxins or derivatives thereof can serve as the position to covalently bond the linking moiety L, and, hence the antibodies or antigen-binding fragments thereof. In some embodiments, the cytotoxin in the ADC of Formula I is an amatoxin or derivative thereof according to formula (II), In one embodiment, the ADC is represented by the formula Ab-Z-L-Am, wherein Ab is an antibody or antigen-binding fragment thereof that binds CD 137, L is a linker, Z is a chemical moiety, and Am is an amatoxin. In certain embodiments, the linker-amatoxin conjugate Am-L-Z is represented by formula (III)

(III)

wherein:

$R_1$ is H, OH, $OR_A$, or $OR_C$;

$R_2$ is H, OH, $OR_B$, or $OR_C$;

$R_A$ and $R_B$, when present, together with the oxygen atoms to which they are bound, combine to form a 5-membered heterocycloalkyl group;

$R_3$ is H, $R_C$, or $R_D$;

each of $R_4$, $R_5$, $R_6$, and $R_7$ is independently H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

Q is —S—, —S(O)—, or —$SO_2$—;

$R_C$ is -L-Z' or -L-Z-Ab, wherein L is optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl; or comprises a dipeptide; or comprises —$((CH_2)_mO)_n(CH_2)_m$, where m and n are each independently selected from 1, 2, 3, 4, 5, 6, 7, 8, 9, and 10; or a combination thereof; Z' is a reactive moiety, and Z is a chemical moiety resulting from a coupling reaction of Z' with a functional group on Ab; and $R_D$ is $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$heteroalkynyl, cycloalkyl, heterocycloalkyl, aryl, heteroaryl, or a combination thereof, wherein each $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, cycloalkyl, heterocycloalkyl, aryl, or heteroaryl is optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

Formula (III) includes an amatoxin and a linker and, in some embodiments, a linker, a chemical moiety, and an antibody.

In some embodiments, the cytotoxin is an amatoxin, and the linker-amatoxin conjugate or the antibody-linker-amatoxin conjugate is represented by formula (IIIA):

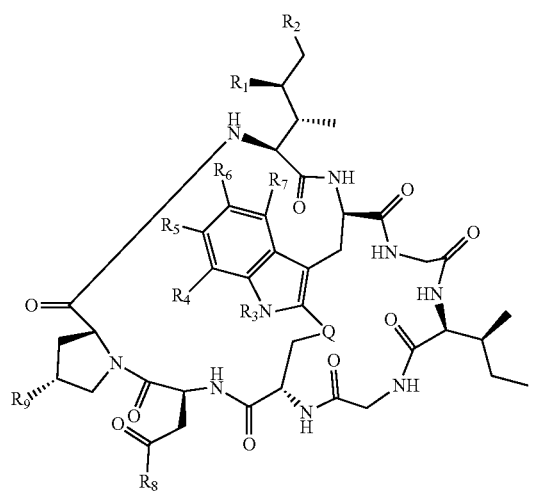

(IIIA)

wherein:
$R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form a 5-membered heterocycloalkyl group;
$R_3$ is H, $R_C$, or $R_D$;
each of $R_4$, $R_5$, $R_6$, and $R_7$ is independently H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
Q is —S—, —S(O)—, or —$SO_2$—;
$R_C$ is -L-Z' or -L-Z-Ab, wherein L is a linker, optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl; or comprises a dipeptide; or comprises —(C=O)—, —((CH$_2$)$_m$O)$_n$(CH$_2$)$_m$—, where m and n are each independently selected from 1, 2, 3, 4, 5, 6, 7, 8, 9, and 10; or a combination thereof; Z' is a reactive moiety, and Z is a chemical moiety resulting from a coupling reaction of Z' with a functional group on Ab; and
$R_D$ is $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, cycloalkyl, heterocycloalkyl, aryl, heteroaryl, or a combination thereof, wherein each $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, cycloalkyl, heterocycloalkyl, aryl, or heteroaryl is optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

In some embodiments, the conjugate contains one $R_C$ substituent.

In some embodiments, $R_A$ and $R_B$, together with the oxygen atoms to which they are bound, combine to form a 5-membered heterocycloalkyl group of formula:

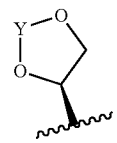

wherein Y is —(C=O)—, —(C=S)—, —(C=$NR_E$)—, or —($CR_ER_{E'}$)—; and
wherein $R_E$ and $R_{E'}$ are each independently H, $C_1$-$C_6$ alkylene-$R_C$, $C_1$-$C_6$ heteroalkylene-$R_C$, $C_2$-$C_6$ alkenylene-$R_C$, $C_2$-$C_6$ heteroalkenylene-$R_C$, $C_2$-$C_6$ alkynylene-$R_C$, $C_2$-$C_6$ heteroalkynylene-$R_C$, cycloalkylene-$R_C$, heterocycloalkylene-$R_C$, arylene-$R_C$, or heteroarylene-$R_C$, or a combination thereof; wherein each $C_1$-$C_6$ alkylene-$R_C$, $C_1$-$C_6$ heteroalkylene-$R_C$, $C_2$-$C_6$ alkenylene-$R_C$, $C_2$-$C_6$ heteroalkenylene-$R_C$, $C_2$-$C_6$ alkynylene-$R_C$, $C_2$-$C_6$ heteroalkynylene-$R_C$, cycloalkylene-$R_C$, heterocycloalkylene-$R_C$, arylene-$R_C$, or heteroarylene-$R_C$ is optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

Formula (IIIA) includes an amatoxin and a linker and, in some embodiments, a linker, a chemical moiety, and an antibody.

In some embodiments, the cytotoxin is an amatoxin or derivative thereof, and the amatoxin-linker conjugate is represented by formula IIIA, wherein:
$R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form:

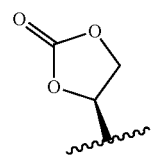

wherein $R_3$ is H or $R_C$.

In some embodiments, the cytotoxin is an amatoxin or derivative thereof and the conjugate is represented by formula IIIA, wherein
$R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form:

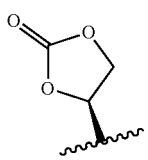

wherein
$R_3$ is H or $R_C$;
$R_4$ and $R_5$ are each independently H, OH, $OR_C$, $R_C$, or $OR_D$;
$R_6$ and $R_7$ are each H;
$R_8$ is OH, $NH_2$, $OR_C$, or $NHR_C$;
$R_9$ is H or OH; and
wherein $R_C$ and $R_D$ are as defined above.

In some embodiments, the cytotoxin is an amatoxin or derivative thereof and the amatoxin-linker conjugate is represented by formula IIIA, wherein:
$R_1$ is H, OH, or $OR_A$;
$R_2$ is H, OH, or $OR_B$;
$R_A$ and $R_B$, when present, together with the oxygen atoms to which they are bound, combine to form:

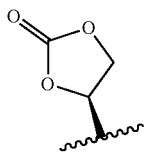

wherein
$R_3$, $R_4$, $R_6$, and $R_7$ are each H;
$R_5$ is $OR_C$;
$R_8$ is OH or $NH_2$;
$R_9$ is H or OH;
Q is —S—, —S(O)—, or —SO$_2$—; and
wherein $R_C$ and $R_D$ are as defined above. Such amatoxin conjugates are described, for example, in U.S. Patent Application Publication No. 2016/0002298, the disclosure of which is incorporated herein by reference in its entirety.

In some embodiments, the cytotoxin is an amatoxin or derivative thereof and the amatoxin-linker conjugate is represented by formula IIIA, wherein:
$R_1$ and $R_2$ are each independently H or OH;
$R_3$ is $R_C$;
$R_4$, $R_6$, and $R_7$ are each H;
$R_5$ is H, OH, or $OC_1$-$C_6$ alkyl;
$R_8$ is OH or $NH_2$;
$R_9$ is H or OH;
Q is —S—, —S(O)—, or —SO$_2$—; and
wherein $R_C$ and $R_D$ are as defined above. Such amatoxin-linker conjugates are described, for example, in U.S. Patent Application Publication No. 2014/0294865, the disclosure of which is incorporated herein by reference in its entirety.

In some embodiments, the cytotoxin is an amatoxin or derivative thereof and the amatoxin-linker conjugate is represented by formula IIIA, wherein:
$R_1$ and $R_2$ are each independently H or OH;
$R_3$, $R_6$, and $R_7$ are each H;
$R_4$ and $R_5$ are each independently H, OH, $OR_C$, or $R_C$;
$R_8$ is OH or $NH_2$;
$R_9$ is H or OH;
Q is —S—, —S(O)—, or —SO$_2$—; and
wherein $R_C$ and $R_D$ are as defined above. Such amatoxin-linker conjugates are described, for example, in U.S. Patent Application Publication No. 2015/0218220, the disclosure of which is incorporated herein by reference in its entirety.

In some embodiments, the cytotoxin is an amatoxin or derivative thereof and the amatoxin-linker conjugate is represented by formula IIIA, wherein:
$R_1$ and $R_2$ are each independently H or OH;
$R_3$, $R_6$, and $R_7$ are each H;
$R_4$ and $R_5$ are each independently H or OH;
$R_8$ is OH, $NH_2$, $OR_C$, or $NHR_C$;
$R_9$ is H or OH;
Q is —S—, —S(O)—, or —SO$_2$—; and
wherein $R_C$ and $R_D$ are as defined above. Such amatoxin conjugates are described, for example, in U.S. Pat. Nos. 9,233,173 and 9,399,681, the disclosures of each of which are incorporated herein by reference in their entirety.

In some embodiments, the cytotoxin is an amatoxin or derivative thereof and the amatoxin-linker conjugate is represented by formula IIIB:

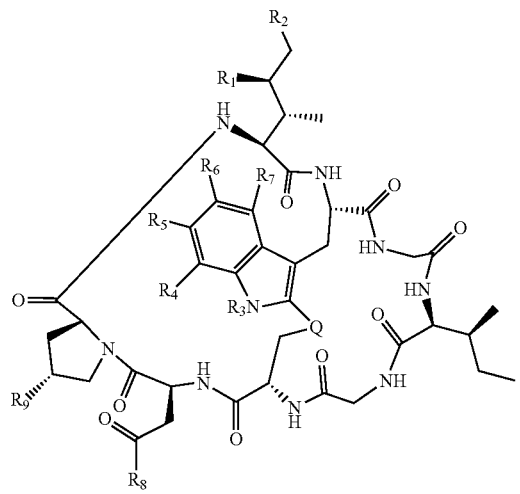

(IIIB)

wherein:
$R_1$ is H, OH, $OR_A$, or $OR_C$;
$R_2$ is H, OH, $OR_B$, or $OR_C$;
$R_A$ and $R_B$, when present, together with the oxygen atoms to which they are bound, combine to form a 5-membered heterocycloalkyl group;
$R_3$ is H, $R_C$, or $R_D$;
each of $R_4$, $R_5$, $R_6$, and $R_7$ is independently H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
Q is —S—, —S(O)—, or —SO$_2$—;
$R_C$ is -L-Z' or -L-Z-Ab, wherein L is a linker, optionally substituted $C_1$-$C_6$ alkyl, optionally substituted $C_1$-$C_6$ heteroalkyl, optionally substituted $C_2$-$C_6$ alkenyl, optionally substituted $C_2$-$C_6$ heteroalkenyl, optionally substituted $C_2$-$C_6$ alkynyl, optionally substituted $C_2$-$C_6$ heteroalkynyl, optionally substituted cycloalkyl, optionally substituted heterocycloalkyl, optionally substituted aryl, a peptide, a dipeptide, —(C═O)—, —((CH$_2$)$_m$O)$_n$(CH$_2$)$_m$, where m and n are each independently selected from 1, 2, 3, 4, 5, 6, 7, 8, 9, and 10; or a combination thereof; Z' is a reactive moiety, and Z is a chemical moiety resulting from a coupling reaction of Z' with a functional group on Ab; and R$_D$ is C$_1$-C$_6$ alkyl, C$_1$-C$_6$ heteroalkyl, C$_2$-C$_6$ alkenyl, C$_2$-C$_6$ heteroalkenyl, C$_2$-C$_6$ alkynyl, C$_2$-C$_6$heteroalkynyl, cycloalkyl, heterocycloalkyl, aryl, heteroaryl, or a combination thereof, wherein each C$_1$-C$_6$ alkyl, C$_1$-C$_6$ heteroalkyl, C$_2$-C$_6$ alkenyl, C$_2$-C$_6$ heteroalkenyl, C$_2$-C$_6$ alkynyl, C$_2$-C$_6$ heteroalkynyl, cycloalkyl, heterocycloalkyl, aryl, or heteroaryl is optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

Formula (IIIB) includes an amatoxin and a linker and, in some embodiments, a linker, a chemical moiety, and an antibody.

In some embodiments, R$_A$ and R$_B$, together with the oxygen atoms to which they are bound, combine to form a 5-membered heterocycloalkyl of formula:

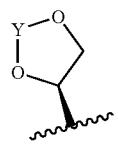

wherein Y is —(C=O)—, —(C=S)—, —(C=NR$_E$)—, or —(CR$_E$R$_{E'}$)—; and wherein R$_E$ and R$_{E'}$ are each independently H, C$_1$-C$_6$ alkylene-R$_C$, C$_1$-C$_6$ heteroalkylene-R$_C$, C$_2$-C$_6$ alkenylene-R$_C$, C$_2$-C$_6$ heteroalkenylene-R$_C$, C$_2$-C$_6$ alkynylene-R$_C$, C$_2$-C$_6$ heteroalkynylene-R$_C$, cycloalkylene-R$_C$, heterocycloalkylene-R$_C$, arylene-R$_C$, or heteroarylene-R$_C$, or a combination thereof, wherein each C$_1$-C$_6$ alkylene-R$_C$, C$_1$-C$_6$ heteroalkylene-R$_C$, C$_2$-C$_6$ alkenylene-R$_C$, C$_2$-C$_6$ heteroalkenylene-R$_C$, C$_2$-C$_6$ alkynylene-R$_C$, C$_2$-C$_6$ heteroalkynylene-R$_C$, cycloalkylene-R$_C$, heterocycloalkylene-R$_C$, arylene-R$_C$, or heteroarylene-R$_C$ is optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

In some embodiments, the antibodies or antigen-binding fragments thereof as described herein are conjugated to an amatoxin-linker conjugate, or derivative thereof, represented by formula IIIB, wherein R$_1$ is H, OH, OR$_A$, or OR$_C$;
R$_2$ is H, OH, OR$_B$, or OR$_C$;
R$_A$ and R$_B$, when present, together with the oxygen atoms to which they are bound, combine to form a 5-membered heterocycloalkyl of formula:

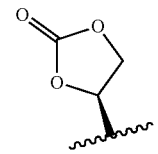

wherein R$_3$ is H or R$_C$.

In some embodiments, the cytotoxin is an amatoxin or derivative thereof and the amatoxin-linker conjugate is represented by formula IIIB, wherein R$_1$ is H, OH, OR$_A$, or OR$_C$;
R$_2$ is H, OH, OR$_B$, or OR$_C$;
R$_A$ and R$_B$, when present, together with the oxygen atoms to which they are bound, combine to form a 5-membered heterocycloalkyl group of formula:

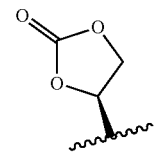

wherein
R$_3$ is H or R$_C$;
R$_4$ and R$_5$ are each independently H, OH, OR$_C$, R$_C$, or OR$_D$;
R$_6$ and R$_7$ are each H;
R$_8$ is OH, NH$_2$, OR$_C$, or NHR$_C$;
R$_9$ is H or OH; and
wherein R$_C$ and R$_D$ are as defined above.

In some embodiments, the cytotoxin is an amatoxin or derivative thereof, and the amatoxin-linker conjugate is represented by formula IIIB, wherein:

R$_1$ is H, OH, or OR$_A$;
R$_2$ is H, OH, or OR$_B$;
R$_A$ and R$_B$, when present, together with the oxygen atoms to which they are bound, combine to form a 5-membered heterocycloalkyl group of formula:

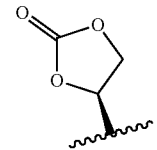

wherein
R$_3$, R$_4$, R$_6$, and R$_7$ are each H;
R$_5$ is OR$_C$;
R$_8$ is OH or NH$_2$;
R$_9$ is H or OH;
Q is —S—, —S(O)—, or —SO$_2$—; and
wherein R$_C$ and R$_D$ are as defined above. Such amatoxin-linker conjugates are described, for example, in U.S. Patent Application Publication No. 2016/0002298, the disclosure of which is incorporated herein by reference in its entirety.

In some embodiments, the cytotoxin is an amatoxin or derivative thereof, and the amatoxin-linker conjugate is represented by formula IIIB, wherein:

$R_1$ and $R_2$ are each independently H or OH;

$R_3$ is $R_C$;

$R_4$, $R_6$, and $R_7$ are each H;

$R_5$ is H, OH, or $OC_1$-$C_6$ alkyl;

$R_8$ is OH or $NH_2$;

$R_9$ is H or OH;

Q is —S—, —S(O)—, or —$SO_2$—; and wherein $R_C$ and $R_D$ are as defined above. Such amatoxin conjugates are described, for example, in U.S. Patent Application Publication No. 2014/0294865, the disclosure of which is incorporated herein by reference in its entirety.

In some embodiments, the cytotoxin is an amatoxin or derivative thereof, and the amatoxin-linker conjugate is represented by formula IIIB, wherein:

$R_1$ and $R_2$ are each independently H or OH;

$R_3$, $R_6$, and $R_7$ are each H;

$R_4$ and $R_5$ are each independently H, OH, $OR_C$, or $R_C$;

$R_8$ is OH or $NH_2$;

$R_9$ is H or OH;

Q is —S—, —S(O)—, or —$SO_2$—; and wherein $R_C$ and $R_D$ are as defined above. Such amatoxin-linker conjugates are described, for example, in U.S. Patent Application Publication No. 2015/0218220, the disclosure of which is incorporated herein by reference in its entirety.

In some embodiments, the cytotoxin is an amatoxin or derivative thereof, and the amatoxin-linker conjugate is represented by formula IIIB, wherein:

$R_1$ and $R_2$ are each independently H or OH;

$R_3$, $R_6$, and $R_7$ are each H;

$R_4$ and $R_5$ are each independently H or OH;

$R_8$ is OH, $NH_2$, $OR_C$, or $NHR_C$;

$R_9$ is H or OH;

Q is —S—, —S(O)—, or —$SO_2$—; and wherein $R_C$ and $R_D$ are as defined above. Such amatoxin-linker conjugates are described, for example, in U.S. Pat. Nos. 9,233,173 and 9,399,681, the disclosures of each of which are incorporated herein by reference in their entirety.

Auristatins

Anti-CD137 antibodies and antigen-binding fragments thereof described herein can be conjugated to a cytotoxin that is an auristatin (U.S. Pat. Nos. 5,635,483; 5,780,588). Auristatins are anti-mitotic agents that interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). (U.S. Pat. Nos. 5,635,483; 5,780,588). The auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF (MMAE and MMAF, respectively), disclosed in Senter et al, Proceedings of the American Association for Cancer Research, Volume 45, Abstract Number 623, presented Mar. 28, 2004, the disclosure of which is expressly incorporated by reference in its entirety.

An exemplary auristatin embodiment is MMAE:

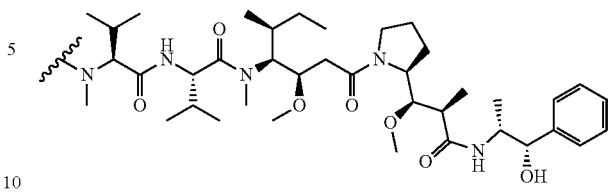

wherein the wavy line indicates the point of covalent attachment to the linker of an antibody-drug or drug-linker conjugate (-L-Z-Ab or -L-Z', as described herein).

Another exemplary auristatin embodiment is MMAF,

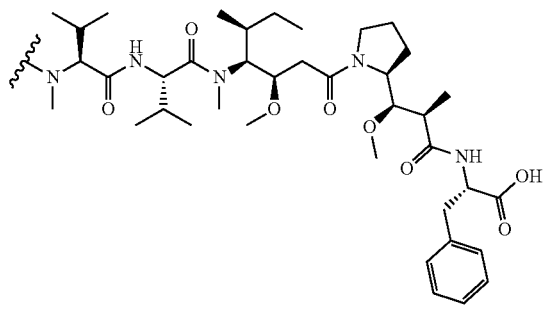 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

wherein the wavy line indicates the point of covalent attachment to the linker of an antibody-linker conjugate (-L-Z-Ab or -L-Z', as described herein), as disclosed in US 2005/0238649:

Auristatins may be prepared according to the methods of: U.S. Pat. Nos. 5,635,483; 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 15:859-863; and Doronina (2003) Nat. Biotechnol. 21(7):778-784.

Maytansinoids

Antibodies and antigen-binding fragments thereof described herein can be conjugated to a cytotoxin that is a microtubule binding agent. In some embodiments, the microtubule binding agent is a maytansine, a maytansinoid or a maytansinoid analog. Maytansinoids are mitototic inhibitors which bind microtubules and act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533. Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Examples of suitable maytansinoids include esters of maytansinol, synthetic maytansinol, and maytansinol analogs and derivatives. Included herein are any cytotoxins that inhibit microtubule formation and that are highly toxic to mammalian cells, as are maytansinoids, maytansinol, and maytansinol analogs, and derivatives.

Examples of suitable maytansinol esters include those having a modified aromatic ring and those having modifications at other positions. Such suitable maytansinoids are disclosed in U.S. Pat. Nos. 4,137,230; 4,151,042; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,362,663; 4,364,866; 4,424,219; 4,450,254; 4,322,348; 4,362,663; 4,371,533; 5,208,020; 5,416,064; 5,475,092; 5,585,499; 5,846,545; 6,333,410; 7,276,497; and 7,473,796, the disclosures of each of which are incorporated herein by reference as they pertain to maytansinoids and derivatives thereof.

In some embodiments, the antibody-drug conjugates (ADCs) of the present disclosure utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the following structural formula IV:

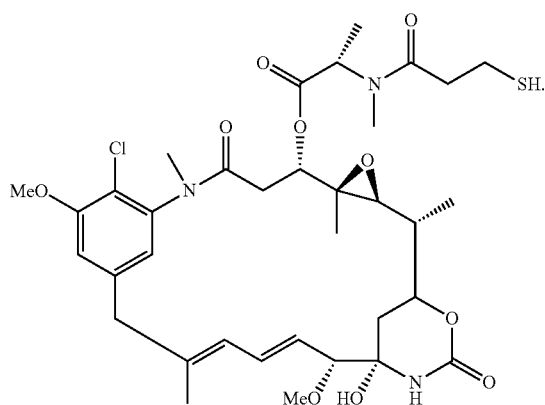

(IV)

In another embodiment, the conjugates of the present invention utilize the thiol-containing maytansinoid $N^{2'}$-deacetyl-$N^{2'}$(4-methyl-4-mercapto-1-oxopentyl)-maytansine (e.g., DM4) as the cytotoxic agent. DM4 is represented by the following structural formula V:

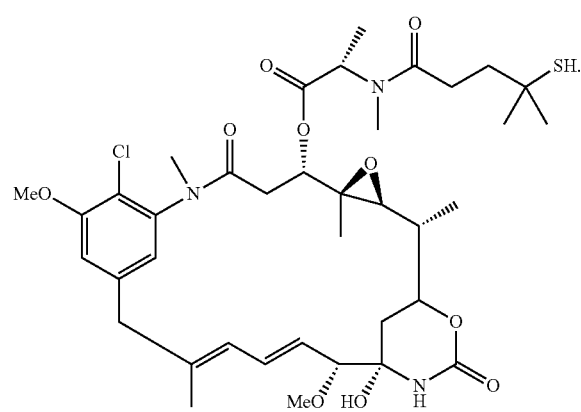

(V)

Another maytansinoid comprising a side chain that contains a sterically hindered thiol bond is $N^{2'}$-deacetyl-$N^{2'}$(4-mercapto-1-oxopentyl)-maytansine (termed DM3), represented by the following structural formula VI:

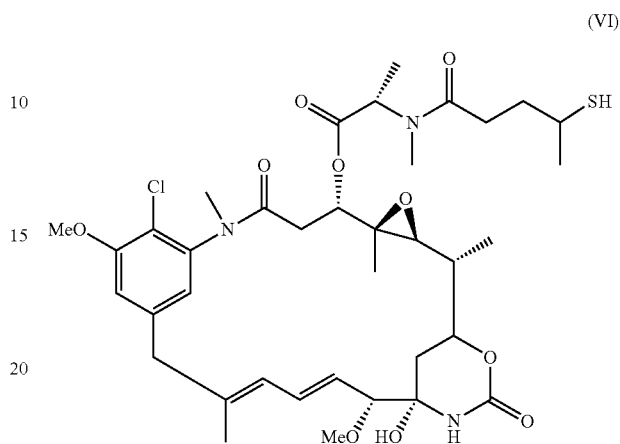

(VI)

Each of the maytansinoids taught in U.S. Pat. Nos. 5,208,020 and 7,276,497, can also be used in the conjugates of the present disclosure. In this regard, the entire disclosure of U.S. Pat. Nos. 5,208,020 and 7,276,697 is incorporated herein by reference.

Many positions on maytansinoids can serve as the position to covalently bond the linking moiety and, hence the antibodies or antigen-binding fragments thereof (-L-Z-Ab or -L-Z', as described herein). For example, the C-3 position having a hydroxyl group, the C-14 position modified with hydroxymethyl, the C-15 position modified with hydroxy and the C-20 position having a hydroxy group are all expected to be useful. In some embodiments, the C-3 position serves as the position to covalently bond the linker moiety, and in some particular embodiments, the C-3 position of maytansinol serves as the position to covalently bond the linking moiety. There are many linking groups known in the art for making antibody-maytansinoid conjugates, including, for example, those disclosed in U.S. Pat. Nos. 5,208,020, 6,441,163, and EP Patent No. 0425235 B1; Chari et al., Cancer Research 52:127-131 (1992); and U.S. 2005/0169933 A1, the disclosures of which are hereby expressly incorporated by reference. Additional linking groups are described and exemplified herein.

The present invention also includes various isomers and mixtures of maytansinoids and conjugates. Certain compounds and conjugates of the present invention may exist in various stereoisomeric, enantiomeric, and diastereomeric forms. Several descriptions for producing such antibody-maytansinoid conjugates are provided in U.S. Pat. Nos. 5,208,020; 5,416,064; 6,333,410; 6,441,163; 6,716,821; and 7,368,565, each of which is incorporated herein in its entirety.

Anthracyclines

In other embodiments, the antibodies and antigen-binding fragments thereof described herein can be conjugated to a cytotoxin that is an anthracycline molecule. Anthracyclines are antibiotic compounds that exhibit cytotoxic activity. Studies have indicated that anthracyclines may operate to kill cells by a number of different mechanisms including: 1) intercalation of the drug molecules into the DNA of the cell thereby inhibiting DNA-dependent nucleic acid synthesis; 2) production by the drug of free radicals which then react with cellular macromolecules to cause damage to the cells or 3) interactions of the drug molecules with the cell membrane [see, e.g., C. Peterson et al.," Transport And Storage Of Anthracycline In Experimental Systems And Human Leukemia" in *Anthracycline Antibiotics In Cancer Therapy*; N. R. Bachur, "Free Radical Damage" id. at pp. 97-102]. Because of their cytotoxic potential anthracyclines have been used in the treatment of numerous cancers such as leukemia, breast carcinoma, lung carcinoma, ovarian adenocarcinoma and sarcomas [see e.g., P. H- Wiernik, in *Anthracycline: Current Status And New Developments* p 11]. Commonly used anthracyclines include doxorubicin, epirubicin, idarubicin and daunomycin.

Representative examples of anthracyclines include, but are not limited to daunorubicin (Cerubidine; Bedford Laboratories), doxorubicin (Adriamycin; Bedford Laboratories; also referred to as doxorubicin hydrochloride, hydroxydaunorubicin, and Rubex), epirubicin (Ellence; Pfizer), and idarubicin (Idamycin; Pfizer Inc.) The anthracycline analog, doxorubicin (ADRIAMYCINO) is thought to interact with DNA by intercalation and inhibition of the progression of the enzyme topoisomerase II, which unwinds DNA for transcription. Doxorubicin stabilizes the topoisomerase II complex after it has broken the DNA chain for replication, preventing the DNA double helix from being resealed and thereby stopping the process of replication. Doxorubicin and daunorubicin (DAUNOMYCIN) are prototype cytotoxic natural product anthracycline chemotherapeutics (Sessa et al., (2007) Cardiovasc. Toxicol. 7:75-79).

One non-limiting example of a suitable anthracycline for use herein is PNU-159682 ("PNU"). PNU exhibits greater than 3000-fold cytotoxicity relative to the parent nemorubicin (Quintieri et al., Clinical Cancer Research 2005, 11, 1608-1617). PNU is represented by the structural formula:

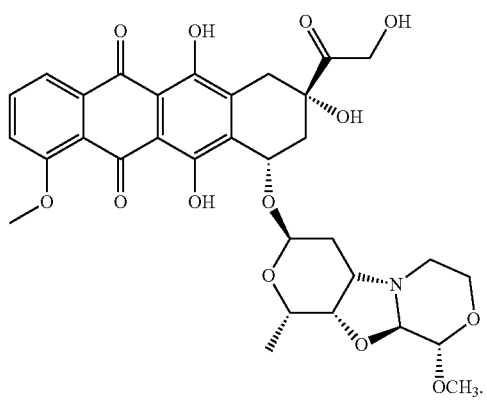

Multiple positions on anthracyclines such as PNU can serve as the position to covalently bond the linking moiety and, hence the anti-CD137 antibodies or antigen-binding fragments thereof as described herein. For example, linkers may be introduced through modifications to the hydroxymethyl ketone side chain.

In some embodiments, the cytotoxin is a PNU derivative represented by the structural formula:

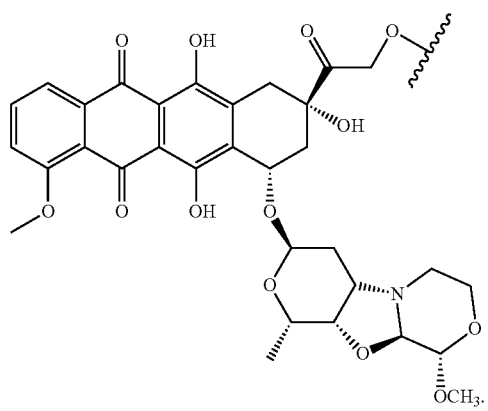

wherein the wavy line indicates the point of covalent attachment to the linker of the ADC as described herein.

In some embodiments, the cytotoxin is a PNU derivative represented by the structural formula:

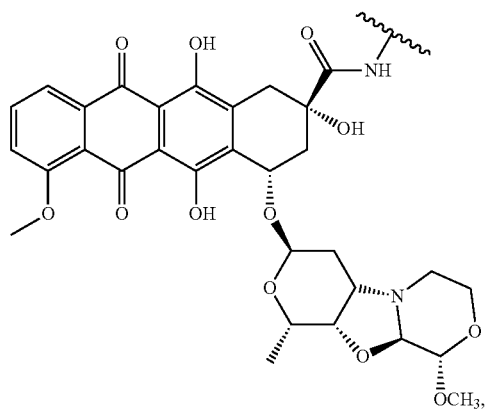

wherein the wavy line indicates the point of covalent attachment to the linker of the ADC as described herein.

Pyrrolobenzodiazepines (PBDs)

In other embodiments, the anti-CD137 antibodies or antigen-binding fragments thereof described herein can be conjugated to a cytotoxin that is a pyrrolobenzodiazepine (PBD) or a cytotoxin that comprises a PBD. PBDs may be produced by certain actinomycetes and have been shown to be sequence selective DNA alkylating compounds. PBD cytotoxins include, but are not limited to, anthramycin, dimeric PBDs, and those disclosed in, for example, Hartley, JA (2011) The development of pyrrolobenzodiazepines as antitumour agents. Expert Opin Inv Drug, 20(6), 733-744 and Antonow D, Thurston DE (2011) Synthesis of DNA-interactive pyrrolo[2,1-c][1,4]benzodiazepines (PBDs). Chem Rev 111: 2815-2864.

In some embodiments, the cytotoxin may be a pyrrolobenzodiazepine dimer represented by the structural formula:

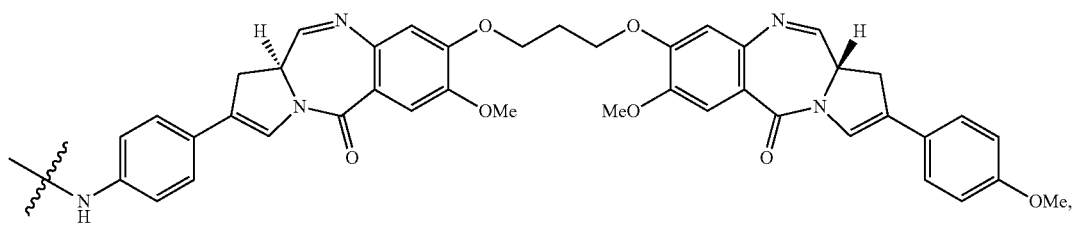 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

wherein the wavy line indicates the point of covalent attachment to the linker of the ADC as described herein. ADCs based on this PBD are disclosed in, for example, Sutherland et al., Blood 2013 122:1455-1463, which is incorporated by reference herein in its entirety.

In some embodiments, the cytotoxin may be a PBD dimer represented by the structural formula:

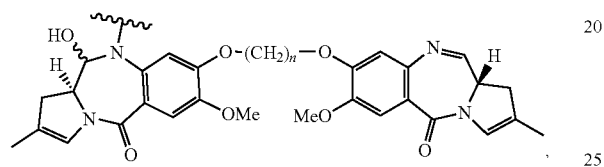

wherein n is 3 or 5, and wherein the wavy line indicates the point of covalent attachment to the linker of the ADC as described herein.

In some embodiments, the cytotoxin may be a PBD dimer represented by the structural formula:

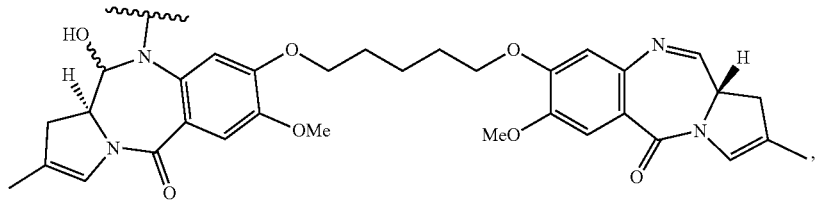

wherein the wavy line indicates the point of covalent attachment to the linker of the ADC as described herein.

In a specific embodiment, the cytotoxin may be a PBD dimer, which, when taken together with a linker and a reactive moiety Z', each as described herein, may be represented by the structure:

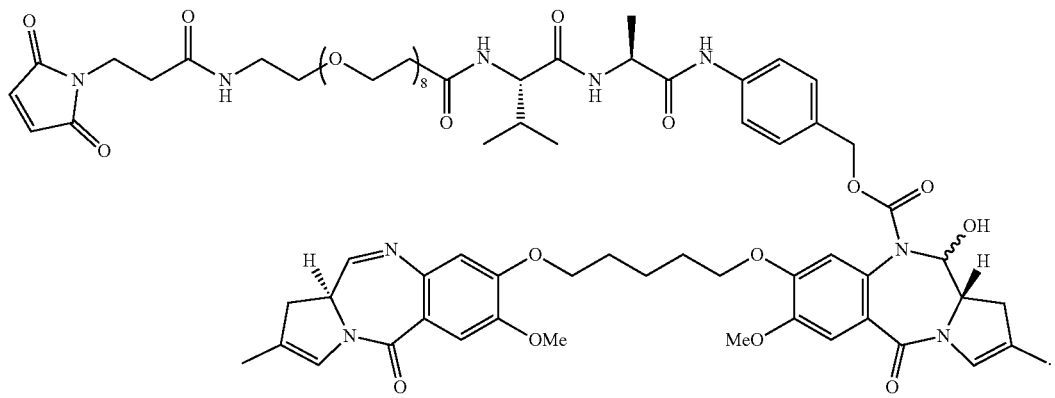

This particular cytotoxin-linker conjugate is known as tesirine (SG3249), and has been described in, for example, Howard et al., ACS Med. Chem. Lett. 2016, 7(11), 983-987, the disclosure of which is incorporated by reference herein in its entirety.

In a specific embodiment, the cytotoxin may be a PBD dimer, which, when taken together with a linker and a reactive moiety Z', each as described herein, may be represented by the structure:

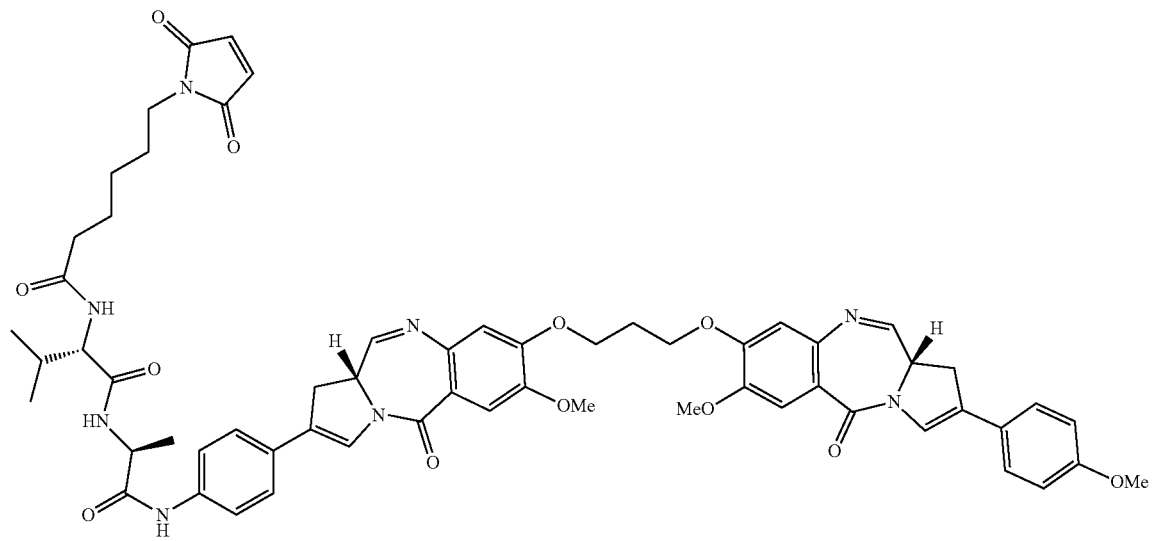 [SMILES: COc1ccc(C2=CN3C(=O)c4cc(OC)c(OCCCOc5cc6c(cc5OC)C(=O)N5C=C(c7ccc(NC(=O)[C@H](C)NC(=O)[C@@H](NC(=O)CCCCCN8C(=O)C=CC8=O)C(C)C)cc7)C[C@@H]5C=N6)cc4N=C[C@@H]3C2)cc1]

This particular cytotoxin-linker conjugate is known as talirine, and has been described, for example, in Mantaj et al., Angewandte Chemie International Edition English 2017, 56, 462-488, the disclosure of which is incorporated by reference herein in its entirety.

Calicheamicin

In other embodiments, the antibodies and antigen-binding fragments thereof described herein can be conjugated to a cytotoxin that is an enediyne antitumor antibiotic (e.g., calicheamicins, ozogamicin). The calicheamicin family of antibiotics are capable of producing double-stranded DNA breaks at sub-picomolar concentrations. Examples of calicheamicins suitable for use in the present invention are disclosed, for example, in U.S. Pat. Nos. 4,671,958; 4,970,198, 5,053,394, 5,037,651; and 5,079,233, which are incorporated herein in their entirety.

An exemplary calicheamicin is designated 71, which is herein referenced simply as gamma, and has the structural formula:

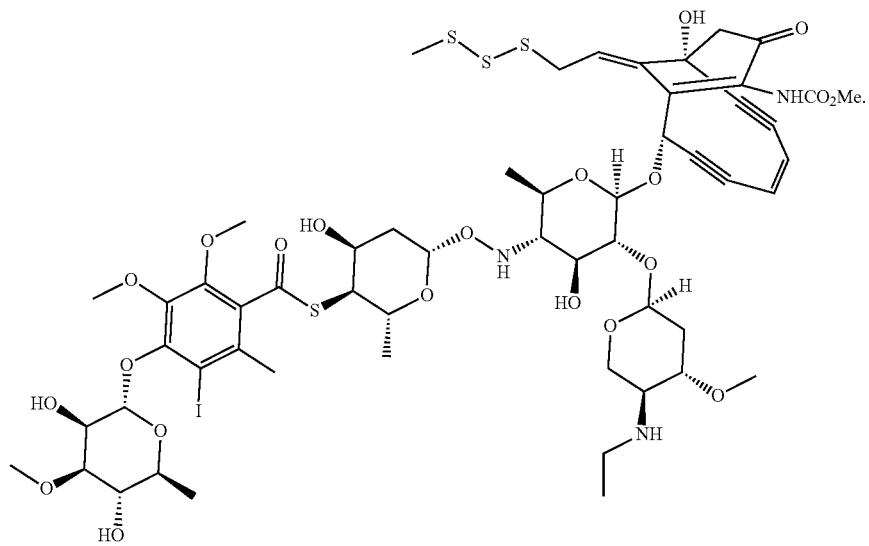

In some embodiments, the calicheamicin is a gamma-calicheamicin derivative or an N-acetyl gamma-calicheamicin derivative. Structural analogues of calicheamicin which may be used include, but are not limited to, those disclosed in, for example, Hinman et al., Cancer Research 53:3336-3342 (1993), Lode et al., Cancer Research 58:2925-2928 (1998), and the aforementioned U.S. patents. Calicheamicins contain a methyltrisulfide moiety that can be reacted with appropriate thiols to form disulfides, at the same time introducing a functional group that is useful in attaching a calicheamicin derivative to an anti-CD137 antibody or antigen-binding fragment thereof as described herein, via a linker. For the preparation of conjugates of the calicheamicin family, see U.S. Pat. Nos. 5,712,374; 5,714,586; 5,739,116; 5,767,285; 5,770,701; 5,770,710; 5,773,001; and 5,877,296 (all to American Cyanamid Company). Structural analogues of calicheamicin which may be used include, but are not limited to, those disclosed in, for example, Hinman et al., Cancer Research 53:3336-3342 (1993), Lode et al., Cancer Research 58:2925-2928 (1998), and the aforementioned U.S. patents to American Cyanamid.

In one embodiment, the cytotoxin of the ADC as disclosed herein is a calicheamicin disulfide derivative represented by the formula:

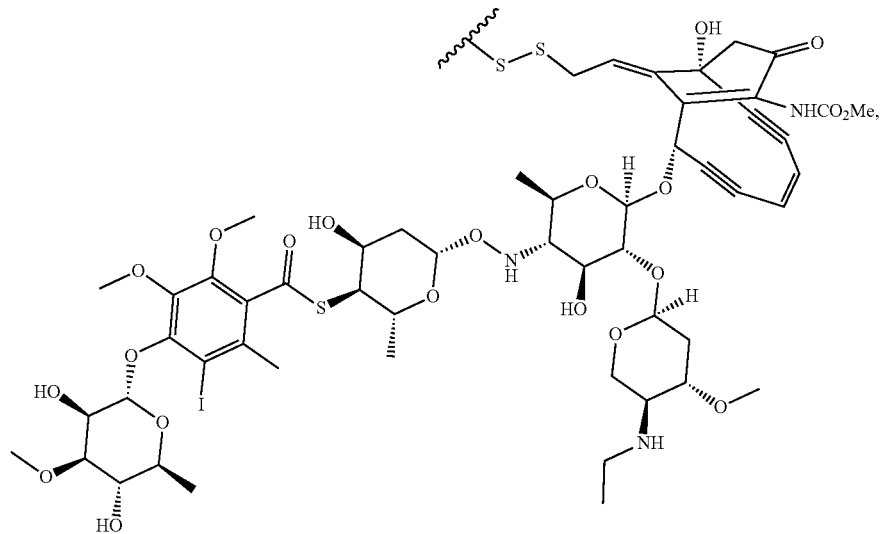

wherein the wavy line indicates the attachment point of the linker.

Additional Cytotoxins

In other embodiments, the antibodies and antigen-binding fragments thereof described herein can be conjugated to a cytotoxin other than or in addition to those cytotoxins disclosed herein above. Additional cytotoxins suitable for use with the compositions and methods described herein include, without limitation, 5-ethynyluracil, abiraterone, acylfulvene, adecypenol, adozelesin, aldesleukin, altretamine, ambamustine, amidox, amifostine, aminolevulinic acid, amrubicin, amsacrine, anagrelide, anastrozole, andrographolide, angiogenesis inhibitors, antarelix, antidorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitors, bicalutamide, bisantrene, bisaziridinylspermine, bisnafide, bistratene A, bizelesin, breflate, bleomycin A2, bleomycin B2, bropirimine, budotitane, buthionine sulfoximine, calcipotriol, calphostin C, camptothecin derivatives (e.g., 10-hydroxy-camptothecin), capecitabine, carboxamide-amino-triazole, carboxyamidotriazole, carzelesin, casein kinase inhibitors, castanospermine, cecropin B, cetrorelix, chlorins, chloroquinoxaline sulfonamide, cicaprost, cis-porphyrin, cladribine, clomifene and analogues thereof, clotrimazole, collismycin A, collismycin B, combretastatin A4, combretastatin analogues, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, 2'deoxycoformycin (DCF), deslorelin, dexifosfamide, dexrazoxane, dexverapamil, diaziquone, didemnin B, didox, diethylnorspermine, dihydro-5-azacytidine, dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epothilones, epithilones, epristeride, estramustine and analogues thereof, etoposide, etoposide 4'-phosphate (also referred to as etopofos), exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, homoharringtonine (HHT), hypericin, ibandronic acid, idoxifene, idramantone, ilmofosine, ilomastat, imidazoacridones, imiquimod, immunostimulant peptides, iobenguane, iododoxorubicin, ipomeanol, irinotecan, iroplact, irsogladine, isobengazole, jasplakinolide, kahalalide F, lamellarin-N triacetate, lanreotide, leinamycin, lenograstim, lentinan sulfate, leptolstatin, letrozole, lipophilic platinum compounds, lissoclinamide 7, lobaplatin, lometrexol, lonidamine, losoxantrone, loxoribine, lurtotecan, lutetium texaphyrin, lysofylline, masoprocol, maspin, matrix metalloproteinase inhibitors, menogaril, rnerbarone, meterelin, methioninase, metoclopramide, MIF inhibitor, ifepristone, miltefosine, mirimostim, mithracin, mitoguazone, mitolactol, mitomycin and analogues thereof, mitonafide, mitoxantrone, mofarotene, molgramostim, mycaperoxide B, myriaporone, N-acetyldinaline, N-substituted benzamides, nafarelin, nagrestip, napavin, naphterpin, nartograstim, nedaplatin, nemorubicin, neridronic acid, nilutamide, nisamycin, nitrullyn, octreotide, okicenone, onapristone, ondansetron, oracin, ormaplatin, oxaliplatin, oxaunomycin, paclitaxel and analogues thereof, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, phenazinomycin, picibanil, pirarubicin, piritrexim, podophyllotoxin, porfiromycin, purine nucleoside phosphorylase inhibitors, raltitrexed, rhizoxin, rogletimide, rohitukine, rubiginone B1, ruboxyl, safingol, saintopin, sarcophytol A, sargramostim, sobuzoxane, sonermin, sparfosic acid, spicamycin D, spiromustine, stipiamide, sulfinosine, tallimustine, tegafur, temozolomide, teniposide, thaliblastine, thiocoraline, tirapazamine, topotecan, topsentin, triciribine, trimetrexate, veramine, vinorelbine, vinxaltine, vorozole, zeniplatin, and zilascorb, among others.

Linkers

The term "Linker" as used herein means a divalent chemical moiety comprising a covalent bond or a chain of atoms that covalently attaches an anti-CD137 antibody or fragment thereof (Ab) to a drug moiety (D) to form antibody-drug conjugates (ADC) of formula I. Suitable linkers have two reactive termini, one for conjugation to an antibody and the other for conjugation to a cytotoxin. The antibody conjugation reactive terminus of the linker (reactive moiety, Z') is typically a site that is capable of conjugation to the antibody through a cysteine thiol or lysine amine group on the antibody, and so is typically a thiol-reactive group such as a double bond (as in maleimide) or a leaving group such as a chloro, bromo, iodo, or an R-sulfanyl group, or an amine-reactive group such as a carboxyl group; while the cytotoxin conjugation reactive terminus of the linker is typically a site that is capable of conjugation to the cytotoxin. Non-limiting examples for linker-cytotoxin conjugation include, for example, formation of an amide bond with a basic amine or carboxyl group on the cytotoxin, via a carboxyl or basic amine group on the linker, respectively, or formation of an ether or the like, via alkylation of an OH group on the cytotoxin, via e.g., a leaving group on the linker. In some embodiments, cytotoxin-linker conjugation is through formation of an amide bond with a basic amine or carboxyl group on the cytotoxin, and so the reactive substituent on the linker is respectively a carboxyl or basic amine group. When the term "linker" is used in describing the linker in conjugated form, one or both of the reactive termini will be absent (such as reactive moiety Z', having been converted to chemical moiety Z) or incomplete (such as being only the carbonyl of the carboxylic acid) because of the formation of the bonds between the linker and/or the cytotoxin, and between the linker and/or the antibody or antigen-binding fragment thereof. Such conjugation reactions are described further herein below.

A variety of linkers can be used to conjugate the antibodies, or antibody fragments, described to a cytotoxic molecule. In some embodiments, the linker is cleavable under intracellular conditions, such that cleavage of the linker releases the drug unit from the antibody in the intracellular environment. In yet other embodiments, the linker unit is not cleavable and the drug is released, for example, by antibody degradation. The linkers useful for the present ADCs are preferably stable extracellularly, prevent aggregation of ADC molecules and keep the ADC freely soluble in aqueous media and in a monomeric state. Before transport or delivery into a cell, the ADC is preferably stable and remains intact, i.e. the antibody remains linked to the drug moiety. The linkers are stable outside the target cell and may be cleaved at some efficacious rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the cytotoxic moiety. Stability of the ADC may be measured by standard analytical techniques such as mass spectroscopy, HPLC, and the separation/analysis technique LC/MS. Covalent attachment of the antibody and the drug moiety requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p. 234-242).

Suitable cleavable linkers include those that may be cleaved, for instance, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012, the disclosure of which is incorporated herein by reference as it pertains to linkers suitable for covalent conjugation). Suitable cleavable linkers may include, for example, chemical moieties such as a hydrazine, a disulfide, a thioether or a dipeptide.

Linkers hydrolyzable under acidic conditions include, for example, hydrazones, semicarbazones, thiosemicarbazones, cis-aconitic amides, orthoesters, acetals, ketals, or the like. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661, the disclosure of each of which is incorporated herein by reference in its entirety as it pertains to linkers suitable for covalent conjugation. Such linkers are relatively stable under neutral pH conditions, such as those in the blood, but are unstable at below pH 5.5 or 5.0, the approximate pH of the lysosome.

Linkers cleavable under reducing conditions include, for example, a disulfide. A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935, the disclosure of each of which is incorporated herein by reference in its entirety as it pertains to linkers suitable for covalent conjugation.

Linkers susceptible to enzymatic hydrolysis can be, e.g., a peptide-containing linker that is cleaved by an intracellular peptidase or protease enzyme, including, but not limited to, a lysosomal or endosomal protease. One advantage of using intracellular proteolytic release of the therapeutic agent is that the agent is typically attenuated when conjugated and the serum stabilities of the conjugates are typically high. In some embodiments, the peptidyl linker is at least two amino acids long or at least three amino acids long. Exemplary amino acid linkers include a dipeptide, a tripeptide, a tetrapeptide or a pentapeptide. Examples of suitable peptides include those containing amino acids such as Valine, Alanine, Citrulline (Cit), Phenylalanine, Lysine, Leucine, and Glycine. Amino acid residues which comprise an amino acid linker component include those occurring naturally, as well as minor amino acids and non-naturally occurring amino acid analogs, such as citrulline. Exemplary dipeptides include valine-citrulline (vc or val-cit) and alanine-phenylalanine (af or ala-phe). Exemplary tripeptides include glycine-valine-citrulline (gly-val-cit) and glycine-glycine-glycine (gly-gly-gly). In some embodiments, the linker includes a dipeptide such as Val-Cit, Ala-Val, or Phe-Lys, Val-Lys, Ala-Lys, Phe-Cit, Leu-Cit, Ile-Cit, Phe-Arg, or Trp-Cit. Linkers containing dipeptides such as Val-Cit or Phe-Lys are disclosed in, for example, U.S. Pat. No. 6,214,345, the disclosure of which is incorporated herein by reference in its entirety as it pertains to linkers suitable for covalent conjugation. In some embodiments, the linker includes a dipeptide selected from Val-Ala and Val-Cit.

Linkers suitable for conjugating the antibodies, or antibody fragments, described herein to a cytotoxic molecule include those capable of releasing a cytotoxin by a 1,6-elimination process. Chemical moieties capable of this elimination process include the p-aminobenzyl (PAB) group, 6-maleimidohexanoic acid, pH-sensitive carbonates, and other reagents as described in Jain et al., Pharm. Res. 32:3526-3540, 2015, the disclosure of which is incorporated herein by reference in its entirety as it pertains to linkers suitable for covalent conjugation.

In some embodiments, the linker includes a "self-immolative" group such as the afore-mentioned PAB or PABC (para-aminobenzyloxycarbonyl), which are disclosed in, for example, Carl et al., J. Med. Chem. (1981) 24:479-480; Chakravarty et al (1983) J. Med. Chem. 26:638-644; U.S. Pat. No. 6,214,345; US20030130189; US20030096743; U.S. Pat. Nos. 6,759,509; US20040052793; U.S. Pat. Nos. 6,218,519; 6,835,807; 6,268,488; US20040018194; WO98/13059; US20040052793; U.S. Pat. Nos. 6,677,435; 5,621,002; US20040121940; WO2004/032828). Other such chemical moieties capable of this process ("self-immolative linkers") include methylene carbamates and heteroaryl groups such as aminothiazoles, aminoimidazoles, aminopyrimidines, and the like. Linkers containing such heterocyclic self-immolative groups are disclosed in, for example, U.S. Patent Publication Nos. 20160303254 and 20150079114, and U.S. Pat. No. 7,754,681; Hay et al. (1999) Bioorg. Med. Chem. Lett. 9:2237; US 2005/0256030; de Groot et al (2001) J. Org. Chem. 66:8815-8830; and U.S. Pat. No. 7,223,837. In some embodiments, a dipeptide is used in combination with a self-immolative linker.

Linkers suitable for use herein further may include one or more groups selected from $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, heteroarylene, and combinations thereof, each of which may be optionally substituted. Non-limiting examples of such groups include $(CH_2)_p$, $(CH_2CH_2O)_p$, and —(C=O)$(CH_2)_p$— units, wherein p is an integer from 1-6, independently selected for each occasion.

In some embodiments, each $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_3$-$C_6$ cycloalkyl, heterocycloalkyl, aryl, or heteroaryl group may be optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

In some embodiments, each $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_3$-$C_6$ cycloalkyl, heterocycloalkyl, aryl, or heteroaryl group may optionally be interrupted by one or more heteroatoms selected from O, S and N.

In some embodiments, each $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_3$-$C_6$ cycloalkyl, heterocycloalkyl, aryl, or heteroaryl group may optionally be interrupted by one or more heteroatoms selected from O, S and N and may be optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

Suitable linkers may contain groups having solubility enhancing properties. Linkers including the $(CH_2CH_2O)_p$ unit (polyethylene glycol, PEG), for example, can enhance solubility, as can alkyl chains substituted with amino, sulfonic acid, phosphonic acid or phosphoric acid residues. Linkers including such moieties are disclosed in, for example, U.S. Pat. Nos. 8,236,319 and 9,504,756, the disclosure of each of which is incorporated herein by reference in its entirety as it pertains to linkers suitable for covalent conjugation. Further solubility enhancing groups include, for example, acyl and carbamoyl sulfamide groups, having the structure:

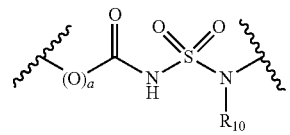

wherein a is 0 or 1; and $R^{10}$ is selected from the group consisting of hydrogen, $C_1$-$C_{24}$ alkyl groups, $C_3$-$C_{24}$ cycloalkyl groups, $C_1$-$C_{24}$ (hetero)aryl groups, $C_1$-$C_{24}$ alkyl(hetero)aryl groups and $C_1$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, each of which may be optionally substituted and/or optionally interrupted by one or more heteroatoms selected from O, S and $NR^{11}R^{12}$, wherein $R^{11}$ and $R^{12}$ are independently selected from the group consisting of hydrogen and $C_1$-$C_4$ alkyl groups; or $R^{10}$ is a cytotoxin, wherein the cytotoxin is optionally connected to N via a spacer moiety. Linkers containing such groups are described, for example, in U.S. Pat. No. 9,636,421 and U.S. Patent Application Publication No. 2017/0298145, the disclosures of which are incorporated herein by reference in their entirety as they pertain to linkers suitable for covalent conjugation to cytotoxins and antibodies or antigen-binding fragments thereof.

In some embodiments, the linker may include one or more of a hydrazine, a disulfide, a thioether, a dipeptide, a p-aminobenzyl (PAB) group, a heterocyclic self-immolative group, an optionally substituted $C_1$-$C_6$ alkyl, an optionally substituted $C_1$-$C_6$ heteroalkyl, an optionally substituted $C_2$-$C_6$ alkenyl, an optionally substituted $C_2$-$C_6$ heteroalkenyl, an optionally substituted $C_2$-$C_6$ alkynyl, an optionally substituted $C_2$-$C_6$ heteroalkynyl, an optionally substituted $C_3$-$C_6$ cycloalkyl, an optionally substituted heterocycloalkyl, an optionally substituted aryl, an optionally substituted heteroaryl, a solubility enhancing group, acyl, —(C=O)—, or —(CH$_2$CH$_2$O)$_p$— group, wherein p is an integer from 1-6. One of skill in the art will recognize that one or more of the groups listed may be present in the form of a bivalent (diradical) species, e.g., $C_1$-$C_6$ alkylene and the like.

In some embodiments, the linker includes a p-aminobenzyl group (PAB). In one embodiment, the p-aminobenzyl group is disposed between the cytotoxic drug and a protease cleavage site in the linker. In one embodiment, the p-aminobenzyl group is part of a p-aminobenzyloxycarbonyl unit. In one embodiment, the p-aminobenzyl group is part of a p-aminobenzylamido unit.

In some embodiments, the linker comprises a dipeptide selected from the group consisting of Phe-Lys, Val-Lys, Phe-Ala, Phe-Cit, Val-Ala, Val-Cit, and Val-Arg. In some embodiments, the linker comprises one or more of PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises a combination of one or more of a peptide, oligosaccharide, —(CH$_2$)$_p$—, —(CH$_2$CH$_2$O)$_p$—, PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises a —(C=O)(CH$_2$)$_p$— unit, wherein p is an integer from 1-6.

In some embodiments, the linker comprises a —(CH$_2$)$_n$— unit, where n is an integer from 2-6. In some embodiments, the linker includes —((CH$_2$)$_n$ where n is 6. In some embodiments, L-Z is

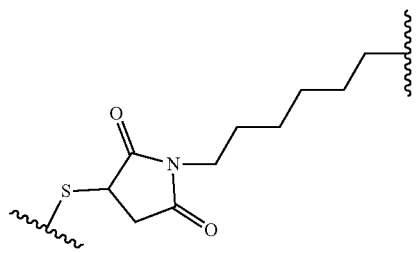

where S is a sulfur atom which represents the reactive substituent present within an antibody, or antigen-binding fragment thereof, that binds CD137 (e.g., from the —SH group of a cysteine residue).

In some embodiments, the linker comprises a ((CH$_2$)$_m$O)$_n$(CH$_2$)$_m$ group where n and m are each independently selected from 1, 2, 3, 4, 5, 6, 7, 8, 9, and 10; and a heteroaryl group, wherein the heteroaryl group is a triazole. In some embodiments, the ((CH$_2$)$_m$O)$_n$(CH$_2$)$_m$ group and triazole together comprise

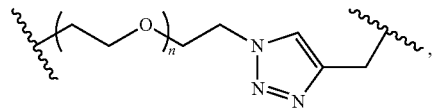

where n is from 1 to 10, and the wavy lines indicate attachment points to additional linker components, the chemical moiety Z, or the amatoxin. Other linkers that may be used in the methods and compositions described herein are described in US 2019/0144504, which is incorporated by reference herein.

In one specific embodiment, the linker comprises PAB-Ala-Val-propionyl, represented by the structure

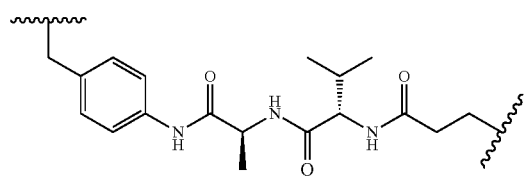 [SMILES: *CCC(=O)N[C@H](C(=O)N[C@@H](C)C(=O)Nc1ccc(C*)cc1)C(C)C]

wherein the wavy lines indicate attachment points to the cytotoxin and the reactive moiety Z'. In another specific embodiment, the linker comprises PAB-Cit-Val-propionyl, represented by the structure

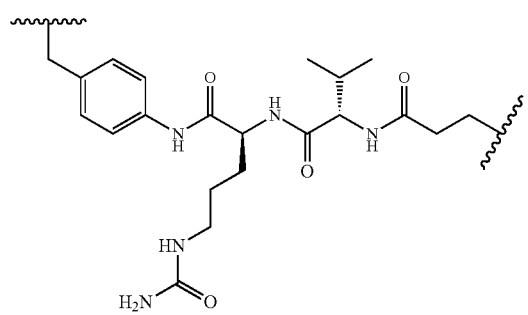 [SMILES: *CCC(=O)N[C@H](C(=O)N[C@@H](CCCNC(N)=O)C(=O)Nc1ccc(C*)cc1)C(C)C]

wherein the wavy lines indicate attachment points to the cytotoxin and the reactive moiety Z'. Such PAB-dipeptide-propionyl linkers are disclosed in, e.g., Patent Application Publication No. WO2017/149077, which is incorporated by reference herein in its entirety. Further, the cytotoxins disclosed in WO2017/149077 are incorporated by reference herein.

It will be recognized by one of skill in the art that any one or more of the chemical groups, moieties and features disclosed herein may be combined in multiple ways to form linkers useful for conjugation of the antibodies and cytotoxins as disclosed herein. Further linkers useful in conjunction with the compositions and methods described herein, are described, for example, in U.S. Patent Application Publication No. 2015/0218220, the disclosure of which is incorporated herein by reference in its entirety.

In certain embodiments, an intermediate, which is the precursor of the linker, is reacted with the drug moiety under appropriate conditions. In certain embodiments, reactive groups are used on the drug and/or the intermediate or linker. The product of the reaction between the drug and the intermediate, or the derivatized drug, is subsequently reacted with the antibody or antigen-binding fragment under appropriate conditions. Alternatively, the linker or intermediate may first be reacted with the antibody or a derivatized antibody, and then reacted with the drug or derivatized drug. Such conjugation reactions will now be described more fully.

A number of different reactions are available for covalent attachment of linkers or drug-linker conjugates to the antibody or antigen-binding fragment thereof. Suitable attachment points on the antibody molecule include the amine groups of lysine, the free carboxylic acid groups of glutamic acid and aspartic acid, the sulfhydryl groups of cysteine, and the various moieties of the aromatic amino acids. For instance, non-specific covalent attachment may be undertaken using a carbodiimide reaction to link a carboxy (or amino) group on a compound to an amino (or carboxy) group on an antibody moiety. Additionally, bifunctional agents such as dialdehydes or imidoesters may also be used to link the amino group on a compound to an amino group on an antibody moiety. Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates may also be used as coupling agents for covalently attaching drugs to binding agents. Other techniques are known to the skilled artisan and within the scope of the present disclosure.

Linkers useful in for conjugation to the antibodies or antigen-binding fragments as described herein include, without limitation, linkers containing chemical moieties Z formed by coupling reactions as depicted in Table 2, below. Curved lines designate points of attachment to the antibody or antigen-binding fragment, and the cytotoxic molecule, respectively.

TABLE 2

Exemplary chemical moieties Z formed by coupling reactions in the formation of antibody-drug conjugates

| Exemplary Coupling Reactions | Chemical Moiety Z Formed by Coupling Reactions |
|---|---|
| [3 + 2] Cycloaddition | 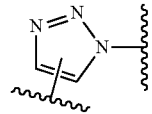 |
| [3 + 2] Cycloaddition | 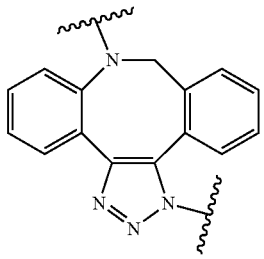 [SMILES: *N1Cc2ccccc2-c2c(nnn2*)-c2ccccc21] |
| [3 + 2] Cycloaddition, Esterification | 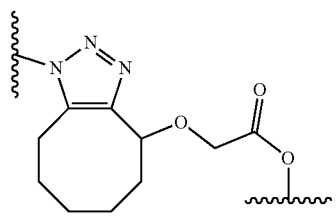 [SMILES: *OC(=O)COC1CCCCCc2c1nnn2*] |
| [3 + 2] Cycloaddition, Esterification | 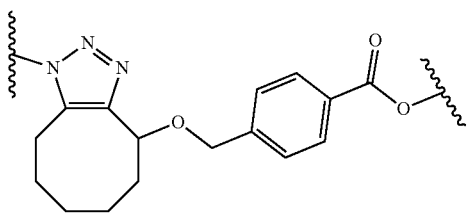 [SMILES: *OC(=O)c1ccc(COC2CCCCCc3c2nnn3*)cc1] |

TABLE 2-continued

Exemplary chemical moieties Z formed by coupling reactions in the formation of antibody-drug conjugates

| Exemplary Coupling Reactions | Chemical Moiety Z Formed by Coupling Reactions |
|---|---|
| [3 + 2] Cycloaddition, Esterification | *(structure: N-triazole fused to cyclooctane ring bearing F substituent and CH2-phenyl-C(O)O- linker)* |
| [3 + 2] Cycloaddition, Esterification | *(structure: N-triazole fused to cyclooctane ring bearing H substituent and CH2-phenyl-C(O)O- linker)* |
| [3 + 2] Cycloaddition, Esterification | *(structure: N-triazole fused to cyclooctane ring bearing gem-difluoro group and CH2-C(O)O- linker)* |
| [3 + 2] Cycloaddition, Esterification | *(structure: N-triazole fused to cyclooctane ring bearing gem-difluoro group and CH2-phenyl-C(O)O- linker)* |
| [3 + 2] Cycloaddition, Esterification | *(structure: N-triazole fused to cyclooctane ring bearing gem-difluoro group and O-CH2-C(O)O- linker)* |

TABLE 2-continued

Exemplary chemical moieties Z formed by coupling reactions in the formation of antibody-drug conjugates

| Exemplary Coupling Reactions | Chemical Moiety Z Formed by Coupling Reactions |
|---|---|
| [3 + 2] Cycloaddition, Esterification | |
| [3 + 2] Cycloaddition, Esterification | |
| [3 + 2] Cycloaddition, Esterification | |
| [3 + 2] Cycloaddition, Esterification | |

TABLE 2-continued

Exemplary chemical moieties Z formed by coupling reactions in the formation of antibody-drug conjugates

| Exemplary Coupling Reactions | Chemical Moiety Z Formed by Coupling Reactions |
|---|---|
| [3 + 2] Cycloaddition, Etherification | |
| [3 + 2] Cycloaddition | |
| Michael addition | |
| Michael addition | |
| Imine condensation, Amidation | |
| Imine condensation | |
| Disulfide formation | |
| Thiol alkylation | |

TABLE 2-continued

Exemplary chemical moieties Z formed by coupling reactions in the formation of antibody-drug conjugates

| Exemplary Coupling Reactions | Chemical Moiety Z Formed by Coupling Reactions |
|---|---|
| Condensation, Michael addition | 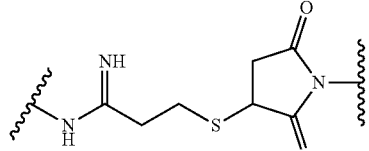 |

One of skill in the art will recognize that a reactive substituent Z' attached to the linker and a reactive substituent on the antibody or antigen-binding fragment thereof, are engaged in the covalent coupling reaction to produce the chemical moiety Z, and will recognize the reactive moiety Z'. Therefore, antibody-drug conjugates useful in conjunction with the methods described herein may be formed by the reaction of an antibody, or antigen-binding fragment thereof, with a linker or cytotoxin-linker conjugate, as described herein, the linker or cytotoxin-linker conjugate including a reactive substituent Z', suitable for reaction with a reactive substituent on the antibody, or antigen-binding fragment thereof, to form the chemical moiety Z.

As depicted in Table 2, examples of suitably reactive substituents on the linker and antibody or antigen-binding fragment thereof include a nucleophile/electrophile pair (e.g., a thiol/haloalkyl pair, an amine/carbonyl pair, or a thiol/α,β-unsaturated carbonyl pair, and the like), a diene/dienophile pair (e.g., an azide/alkyne pair, or a diene/α,β-unsaturated carbonyl pair, among others), and the like. Coupling reactions between the reactive substitutents to form the chemical moiety Z include, without limitation, thiol alkylation, hydroxyl alkylation, amine alkylation, amine or hydroxylamine condensation, hydrazine formation, amidation, esterification, disulfide formation, cycloaddition (e.g., [4+2] Diels-Alder cycloaddition, [3+2] Huisgen cycloaddition, among others), nucleophilic aromatic substitution, electrophilic aromatic substitution, and other reactive modalities known in the art or described herein. Preferably, the linker contains an electrophilic functional group for reaction with a nucleophilic functional group on the antibody, or antigen-binding fragment thereof.

Reactive substituents that may be present within an antibody, or antigen-binding fragment thereof, as disclosed herein include, without limitation, nucleophilic groups such as (i)N-terminal amine groups, (ii) side chain amine groups, e.g. lysine, (iii) side chain thiol groups, e.g. cysteine, and (iv) sugar hydroxyl or amino groups where the antibody is glycosylated. Reactive substituents that may be present within an antibody, or antigen-binding fragment thereof, as disclosed herein include, without limitation, hydroxyl moieties of serine, threonine, and tyrosine residues; amino moieties of lysine residues; carboxyl moieties of aspartic acid and glutamic acid residues; and thiol moieties of cysteine residues, as well as propargyl, azido, haloaryl (e.g., fluoroaryl), haloheteroaryl (e.g., fluoroheteroaryl), haloalkyl, and haloheteroalkyl moieties of non-naturally occurring amino acids. In some embodiments, the reactive substituents present within an antibody, or antigen-binding fragment thereof as disclosed herein include, are amine or thiol moieties. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

In some embodiments, the reactive moiety Z' attached to the linker is a nucleophilic group which is reactive with an electrophilic group present on an antibody. Useful electrophilic groups on an antibody include, but are not limited to, aldehyde and ketone carbonyl groups. The heteroatom of a nucleophilic group can react with an electrophilic group on an antibody and form a covalent bond to the antibody. Useful nucleophilic groups include, but are not limited to, hydrazide, oxime, amino, hydroxyl, hydrazine, thiosemicarbazone, hydrazine carboxylate, and arylhydrazide.

In some embodiments, Z is the product of a reaction between reactive nucleophilic substituents present within the antibodies, or antigen-binding fragments thereof, such as amine and thiol moieties, and a reactive electrophilic substituent Z'. For instance, Z' may be a Michael acceptor (e.g., maleimide), activated ester, electron-deficient carbonyl compound, and aldehyde, among others. Several representative and non-limiting examples of reactive substituents Z' and the resulting chemical moieties Z are provided in Table 3.

TABLE 3

Complementary reactive substituents and chemical moieties

| Functional Group on Antibody | Z' group | Z group |
|---|---|---|
| Naturally Occurring —SH |  | 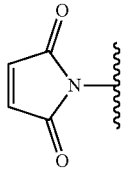 |
| | 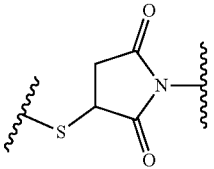 [SMILES: *SC1CC(=O)N(*)C1=O] |  |
| —NH₂ | 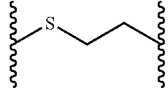 [SMILES: *CCS*] X |  |
| Synthetically Introduced ≡ |  N₃— | 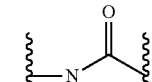 |
| —N₃ |  ≡ |  |
| | 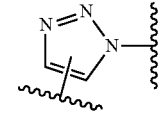 |  |
|  R = H or alkyl | H₂N—Y— (Y = O or NH) | 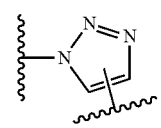 |

For instance, linkers suitable for the synthesis of ADCs include, without limitation, reactive substituents Z' such as maleimide or haloalkyl groups. These may be attached to the linker by reagents such as succinimidyl 4-(N-maleimidomethyl)-cyclohexane-L-carboxylate (SMCC), N-succinimidyl iodoacetate (SIA), sulfo-SMCC, m-maleimidobenzoyl-N-hydroxysuccinimidyl ester (MBS), sulfo-MBS, and succinimidyl iodoacetate, among others described, in for instance, Liu et al., 18:690-697, 1979, the disclosure of which is incorporated herein by reference as it pertains to linkers for chemical conjugation.

In some embodiments, the reactive substituent Z' attached to linker L is a maleimide, azide, or alkyne. An example of a maleimide-containing linker is the non-cleavable maleimidocaproyl-based linker, which is particularly useful for the conjugation of microtubule-disrupting agents such as auristatins. Such linkers are described by Doronina et al., Bioconjugate Chem. 17:14-24, 2006, the disclosure of which is incorporated herein by reference as it pertains to linkers for chemical conjugation.

In some embodiments, the reactive substituent Z' is —(C═O)— or —NH(C═O)—, such that the linker may be joined to the antibody, or antigen-binding fragment thereof, by an amide or urea moiety, respectively, resulting from reaction of the —(C═O)— or —NH(C═O)— group with an amino group of the antibody or antigen-binding fragment thereof.

In some embodiments, the reactive substituent is an N-maleimidyl group, halogenated N-alkylamido group, sulfonyloxy N-alkylamido group, carbonate group, sulfonyl halide group, thiol group or derivative thereof, alkynyl group comprising an internal carbon-carbon triple bond, (het-ero)cycloalkynyl group, bicyclo[6.1.0]non-4-yn-9-yl group, alkenyl group comprising an internal carbon-carbon double bond, cycloalkenyl group, tetrazinyl group, azido group, phosphine group, nitrile oxide group, nitrone group, nitrile imine group, diazo group, ketone group, (O-alkyl) hydroxylamino group, hydrazine group, halogenated N-maleimidyl group, 1,1-bis (sulfonylmethyl)methylcarbonyl group or elimination derivatives thereof, carbonyl halide group, or an allenamide group, each of which may be optionally substituted. In some embodiments, the reactive substituent comprises a cycloalkene group, a cycloalkyne group, or an optionally substituted (hetero)cycloalkynyl group.

Non-limiting examples of amatoxin-linker conjugates containing a reactive substituent Z' suitable for reaction with a reactive residue on the antibody or antigen-binding fragment thereof include, without limitation, 7'C-(4-(6-(maleimido)hexanoyl)piperazin-1-yl)-amatoxin; 7'C-(4-(6-(maleimido)hexanamido)piperidin-1-yl)-amatoxin; 7'C-(4-(6-(6-(maleimido)hexanamido)hexanoyl)piperazin-1-yl)-amatoxin; 7'C-(4-(4-((maleimido)methyl)cyclohexanecarbonyl)piperazin-1-yl)-amatoxin; 7'C-(4-(6-(4-((maleimido)methyl)cyclohexanecarboxamido)hexanoyl)piperazin-1-yl)-amatoxin; 7'C-(4-(2-(6-(maleimido)hexanamido)ethyl)piperidin-1-yl)-amatoxin; 7'C-(4-(2-(6-(6-(maleimido)hexanamido)hexanamido)ethyl)piperidin-1-yl)-amatoxin; 7'C-(4-(2-(4-((maleimido)methyl)cyclohexanecarboxamido)ethyl)piperidin-1-yl)-amatoxin; 7'C-(4-(2-(6-(4-((maleimido)methyl)cyclohexanecarboxamido)hexanamido)ethyl)piperidin-1-yl)-amatoxin; 7'C-(4-(2-(3-carboxypropanamido)ethyl)piperidin-1-yl)-amatoxin; 7'C-(4-(2-(2-bromoacetamido)ethyl)piperidin-1-yl)-amatoxin; 7'C-(4-(2-(3-(pyridin-2-yldisulfanyl)propanamido)ethyl)piperidin-1-yl)-amatoxin; 7'C-(4-(2-(4-(maleimido)butanamido)ethyl)piperidin-1-yl)-amatoxin; 7'C-(4-(2-(maleimido)acetyl)piperazin-1-yl)-amatoxin; 7'C-(4-(3-(maleimido)propanoyl)piperazin-1-yl)-amatoxin; 7'C-(4-(4-(maleimido)butanoyl)piperazin-1-yl)-amatoxin; 7'C-(4-(2-(6-(4-((maleimido)methyl)cyclohexanecarboxamido)hexanamido)ethyl)piperidin-1-yl)-amatoxin; 7'C-(3-((6-(maleimido)hexanamido)methyl)pyrrolidin-1-yl)-amatoxin; 7'C-(3-((6-(6-(maleimido)hexanamido)hexanamido)methyl)pyrrolidin-1-yl)-amatoxin; 7'C-(3-((4-((maleimido)methyl)cyclohexanecarboxamido)methyl)pyrrolidin-1-yl)-amatoxin; 7'C-(3-((6-((4-(maleimido)methyl)cyclohexanecarboxamido)hexanamido)methyl)pyrrolidin-1-yl)-amatoxin; 7'C-(4-(2-(6-(2-(aminooxy)acetamido)hexanamido)ethyl)piperidin-1-yl)-amatoxin; 7'C-(4-(2-(4-(2-(aminooxy)acetamido)butanamido)ethyl)piperidin-1-yl)-amatoxin; 7'C-(4-(4-(2-(aminooxy)acetamido)butanoyl)piperazin-1-yl)-amatoxin; 7'C-(4-(6-(2-(aminooxy)acetamido)hexanoyl)piperazin-1-yl)-amatoxin; 7'C-((4-(6-(maleimido)hexanamido)piperidin-1-yl)methyl)-amatoxin; 7'C-((4-(2-(6-(maleimido)hexanamido)ethyl)piperidin-1-yl)methyl)-amatoxin; 7'C-((4-(6-(maleimido)hexanoyl)piperazin-1-yl)methyl)-amatoxin; (R)-7'C-((3-((6-(maleimido)hexanamido)methyl)pyrrolidin-1-yl)methyl)-amatoxin; (S)-7'C-((3-((6-(maleimido)hexanamido)methyl)pyrrolidin-1-yl)methyl)-amatoxin; 7'C-((4-(2-(6-(6-(maleimido)hexanamido)hexanamido)ethyl)piperidin-1-yl)methyl)-amatoxin; 7'C-((4-(2-(4-((maleimido)methyl)cyclohexanecarboxamido)ethyl)piperidin-1-yl)methyl)-amatoxin; 7'C-((4-(2-(6-(4-((maleimido)methyl)cyclohexanecarboxamido)hexanamido)ethyl)piperidin-1-yl)methyl)-amatoxin; 7'C-((4-(2-(6-(maleimido)hexanamido)ethyl)piperazin-1-yl)methyl)-amatoxin; 7'C-((4-(2-(6-(6-(maleimido)hexanamido)hexanamido)ethyl)piperazin-1-yl)methyl)-amatoxin; 7'C-((4-(2-(4-((maleimido)methyl)cyclohexanecarboxamido)ethyl)piperazin-1-yl)methyl)-amatoxin; 7'C-((4-(2-(6-(4-((maleimido)methyl)cyclohexanecarboxamido)hexanamido)ethyl)piperazin-1-yl)methyl)-amatoxin; 7'C-((3-((6-(6-(maleimido)hexanamido)hexanamido)-S-methyl)pyrrolidin-1-yl)methyl)-amatoxin; 7'C-((3-((6-(6-(maleimido)hexanamido)hexanamido)-R-methyl)pyrrolidin-1-yl)methyl)-amatoxin; 7'C-((3-((4-((maleimido)methyl)cyclohexanecarboxamido)-S-methyl)pyrrolidin-1-yl)methyl)-amatoxin; 7'C-((3-((4-((maleimido)methyl)cyclohexanecarboxamido)-R-methyl)pyrrolidin-1-yl)methyl)-amatoxin; 7'C-((3-((6-(4-((maleimido)methyl)cyclohexanecarboxamido)hexanamido)methyl)pyrrolidin-1-yl)methyl)-amatoxin; 7'C-((4-(2-(3-carboxypropanamido)ethyl)piperazin-1-yl)methyl)-amatoxin; 7'C-((4-(6-(6-(maleimido)hexanamido)hexanoyl)piperazin-1-yl)methyl)-amatoxin; 7'C-((4-(6-(4-((maleimido)methyl)cyclohexanecarboxamido)hexanoyl)piperazin-1-yl)methyl)-amatoxin; 7'C-((4-(2-(maleimido)acetyl)piperazin-1-yl)methyl)-amatoxin; 7'C-((4-(3-(maleimido)propanoyl)piperazin-1-yl)methyl)-amatoxin; 7'C-((4-(4-(maleimido)butanoyl)piperazin-1-yl)methyl)-amatoxin; 7'C-((4-(2-(2-(maleimido)acetamido)ethyl)piperidin-1-yl)methyl)-amatoxin; 7'C-((4-(2-(4-(maleimido)butanamido)ethyl)piperidin-1-yl)methyl)-amatoxin; 7'C-((4-(2-(6-(4-((maleimido)methyl)cyclohexanecarboxamido)hexanamido)ethyl)piperidin-1-yl)methyl)-amatoxin; 7'C-((3-((6-(maleimido)hexanamido)methyl)azetidin-1-yl)methyl)-amatoxin; 7'C-((3-(2-(6-(maleimido)hexanamido)ethyl)azetidin-1-yl)methyl)-amatoxin; 7'C-((3-((4-((maleimido)methyl)cyclohexanecarboxamido)methyl)azetidin-1-yl)methyl)-amatoxin; 7'C-((3-(2-(4-((maleimido)methyl)cyclohexanecarboxamido)ethyl)azetidin-lyl)methyl)-amatoxin; 7'C-((3-(2-(6-(4-((maleimido)methyl)cyclohexanecarboxamido)hexanamido)ethyl)azetidin-1-yl)methyl)-amatoxin; 7'C-(((2-(6-(maleimido)-N-methylhexanamido)ethyl)(methyl)amino)methyl)-amatoxin; 7'C-(((4-(6-(maleimido)-N-methylhexanamido)butyl(methyl)amino)methyl)-amatoxin; 7'C-((2-(2-(6-(maleimido)hexanamido)ethyl)aziridin-1-yl)methyl)-amatoxin; 7'C-((2-(2-(6-(4-((maleimido)methyl)cyclohexanecarboxamido)hexanamido)ethyl)aziridin-1-yl)methyl)-amatoxin; 7'C-((4-(6-(6-(2-(aminooxy)acetamido)hexanamido)hexanoyl)piperazin-1-yl)methyl)-amatoxin; 7'C-((4-(1-(aminooxy)-2-oxo-6,9,12,15-tetraoxa-3-azaheptadecan-17-oyl)piperazin-1-yl)methyl)-amatoxin; 7'C-((4-(2-(2-(aminooxy)acetamido)acetyl)piperazin-1-yl)methyl)-amatoxin; 7'C-((4-(3-(2-(aminooxy)acetamido)propanoyl)piperazin-1-yl)methyl)-amatoxin; 7'C-((4-(4-(2-(aminooxy)acetamido)butanoyl)piperazin-1-yl)methyl)-amatoxin; 7'C-((4-(2-(6-(2-(aminooxy)acetamido)hexanamido)ethyl)piperidin-1-yl)methyl)-amatoxin; 7'C-((4-(2-(2-(2-(aminooxy)acetamido)acetamido)ethyl)piperidin-1-yl)methyl)-amatoxin; 7'C-((4-(2-(4-(2-(aminooxy)acetamido)butanamido)ethyl)piperidin-1-yl)methyl)-amatoxin; 7'C-((4-(20-(aminooxy)-4,19-dioxo-6,9,12,15-tetraoxa-3,18-diazaicosyl)piperidin-1-yl)methyl)-amatoxin; 7'C-(((2-(6-(2-(aminooxy)acetamido)-N-methylhexanamido)ethyl)(methyl)amino)methyl)-amatoxin; 7'C-(((4-(6-(2-(aminooxy)acetamido)-N-methylhexanamido)butyl)(methyl)amino)methyl)-amatoxin; 7'C-((3-((6-(4-((maleimido)methyl)cyclohexanecarboxamido)hexanamido)methyl)pyrrolidin-1-yl)-S-methyl)-amatoxin; 7'C-((3-((6-(4-((maleimido)methyl)cyclohexanecarboxamido)hexanamido)-R-methyl)pyrrolidin-1-yl)methyl)-amatoxin; 7'C-((4-(2-(2-bromoacetamido)ethyl)piperazin-1-yl)methyl)-amatoxin; 7'C-((4-(2-(2-bromoacetamido)ethyl)piperidin-1-yl)methyl)-amatoxin; 7'C-((4-(2-(3-(pyridine-2-yldisulfanyl)propanamido)ethyl)piperidin-1-yl)methyl)-amatoxin; 6'O-(6-(6-(maleimido)hexanamido)hexyl)-amatoxin; 6'O-(5-(4-((maleimido)methyl)cyclohexanecarboxamido)pentyl)-amatoxin; 6'O-(2-((6-(maleimido)hexyl)oxy)-2-oxoethyl)-amatoxin; 6'O-((6-(maleimido)hexyl)carbamoyl)-amatoxin; 6'O-((6-(4-((maleimido)methyl)cyclohexanecarboxamido)hexyl)carbamoyl)-amatoxin; 6'O-(6-(2-bromoacetamido)hexyl)-amatoxin; 7'C-(4-(6-(azido)hexanamido)piperidin-1-yl)-amatoxin; 7'C-(4-(hex-S-ynoylamino)piperidin-1-yl)- amatoxin; 7'C-(4-(2-(6-(maleimido)hexanamido)ethyl) piperazin-1-yl)-amatoxin; 7'C-(4-(2-(6-(6-(maleimido) hexanamido)hexanamido)ethyl)piperazin-1-yl)-amatoxin; 6'O-(6-(6-(11,12-didehydro-5,6-dihydro-dibenz[b,f]azocin-S-yl)-6-oxohexanamido)hexyl)-amatoxin; 6'O-(6-(hex-S-ynoylamino)hexyl)-amatoxin; 6'O-(6-(2-(aminooxy)acetylamido)hexyl)-amatoxin; 6'O-((6-aminooxy)hexyl)-amatoxin; and 6'O-(6-(2-iodoacetamido)hexyl)-amatoxin.

In some embodiments, the chemical moiety Z is selected from Table 2 or Table 3. In some embodiments, the chemical moiety Z is:

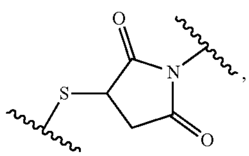

where S is a sulfur atom which represents the reactive substituent present within an antibody, or antigen-binding fragment thereof, such as an anti-CD-137 antibody.

In some embodiments, an amatoxin as disclosed herein is conjugated to a linker-reactive moiety -L-Z' having the following formula:

where the wavy line indicates the point of attachment to a substituent on the cytotoxin (e.g., an amatoxin). This linker-reactive substituent group L-Z' may alternatively be referred to as N-beta-maleimidopropionyl-Val-Ala-para-aminobenzyl (BMP-Val-Ala-PAB).

In some embodiments, an amatoxin as disclosed herein is conjugated to a linker-reactive moiety -L-Z' having the following formula:

where the wavy line indicates the point of attachment to a substituent on the cytotoxin (e.g., an amatoxin). This linker-reactive substituent group L-Z' may alternatively be referred to as N-beta-maleimidopropyl-Val-Cit-para-aminobenzyl (BMP-Val-Cit-PAB).

In some embodiments, the linker L and the chemical moiety Z, taken together as L-Z, is 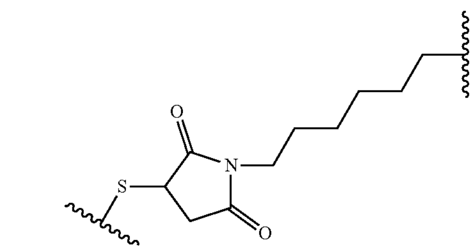 or 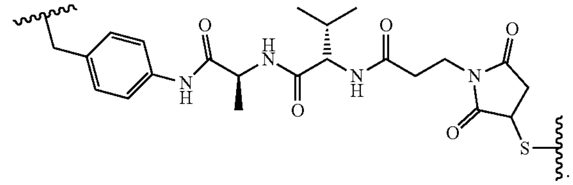 where S is a sulfur atom which represents the reactive substituent present within an antibody, or antigen-binding fragment thereof, such as an anti-CD-5 antibody. The wavy line at the linker terminus indicates the point of attachment to the amatoxin.

In some embodiments, the linker L and the chemical moiety Z, after conjugation to the antibody, taken together as L-Z-Ab, has the structure:

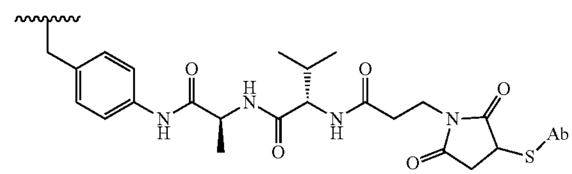

where S is a sulfur atom which represents the reactive substituent present within an antibody, or antigen-binding fragment thereof, such as an anti-CD-137 antibody. The wavy line at the linker terminus indicates the point of attachment to the amatoxin.

The foregoing linker moieties and amatoxin-linker conjugates, among others useful in conjunction with the compositions and methods described herein, are described, for example, in U.S. Patent Application Publication No. 2015/0218220 and Patent Application Publication No. WO2017/149077, the disclosure of each of which is incorporated herein by reference in its entirety.

The foregoing linker moieties and amatoxin-linker conjugates, among others useful in conjunction with the compositions and methods described herein, are described, for example, in U.S. Patent Application Publication No. 2015/0218220 and Patent Application Publication No. WO2017/149077, the disclosure of each of which is incorporated herein by reference in its entirety.

In one embodiment, the CD137 antibodies, or antigen-binding fragments, described herein may be bound to an amatoxin so as to form a conjugate represented by the formula Ab-Z-L-Am, wherein Ab is the CD137 antibody, or antigen-binding fragment thereof, L is a linker, Z is a chemical moiety and Am is an amatoxin, each as described herein.

In some embodiments, Am-L-Z-Ab is:
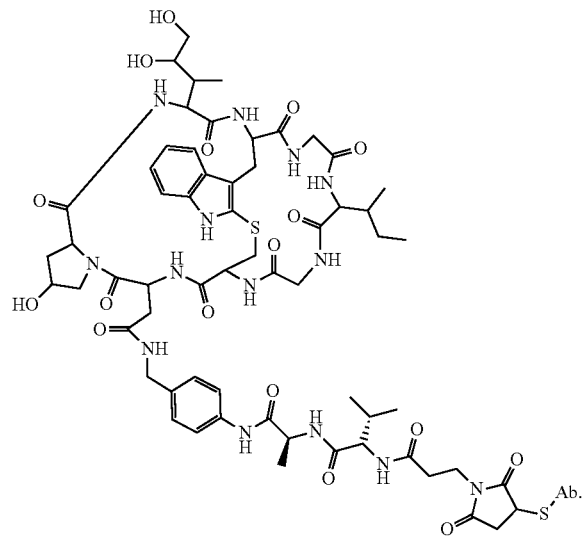
In some embodiments, Am-L-Z-Ab is:
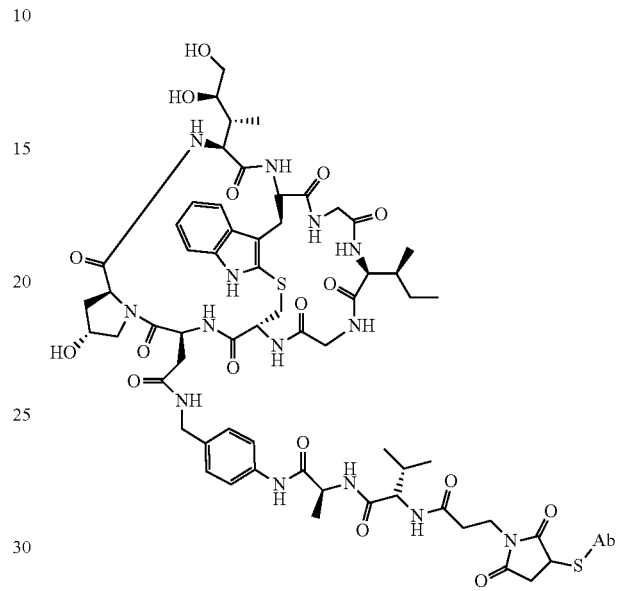
In some embodiments, Am-L-Z-Ab is:
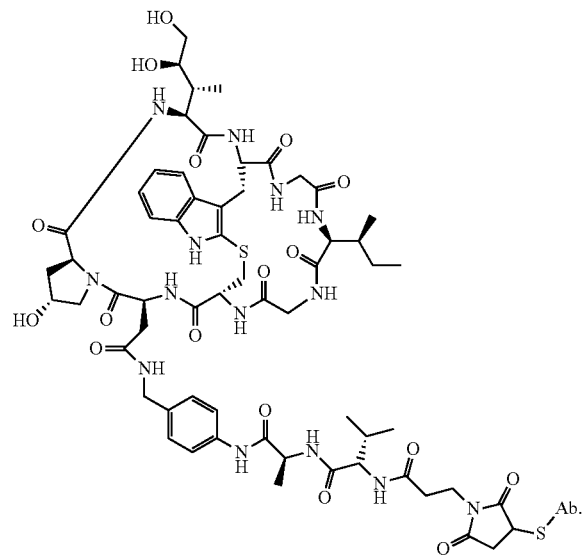
In some embodiments, Am-L-Z-Ab is:
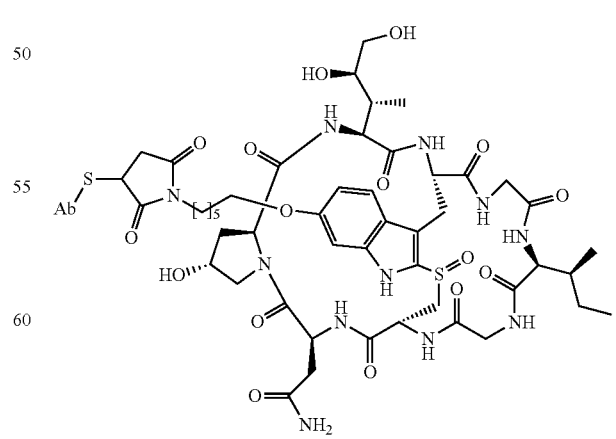

In some embodiments, Am-L-Z-Ab is:

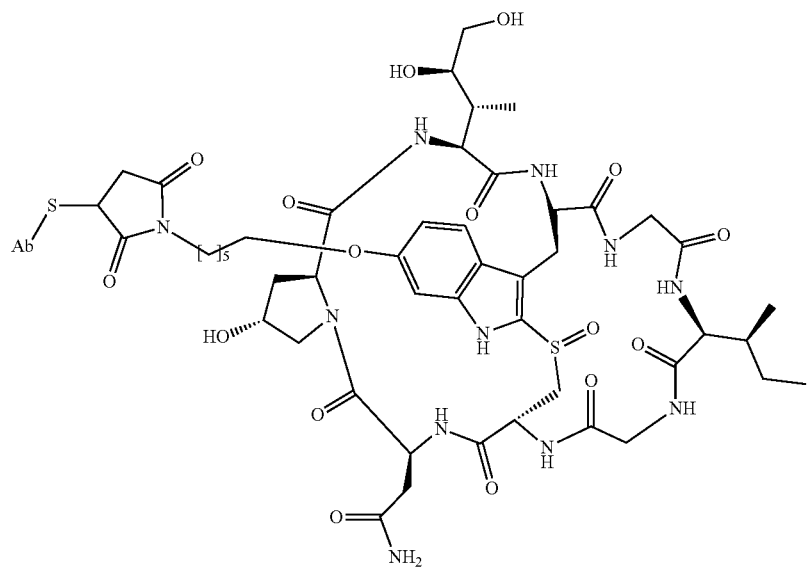

Preparation of Antibody-Drug Conjugates

In the ADCs of formula I as disclosed herein, an anti-CD137 antibody or antigen binding fragment thereof is conjugated to one or more cytotoxic drug moieties (D), e.g. about 1 to about 20 drug moieties per antibody, through a linker L and a chemical moiety Z as disclosed herein. The ADCs of the present disclosure may be prepared by several routes, employing organic chemistry reactions, conditions, and reagents known to those skilled in the art, including: (1) reaction of a reactive substituent of an antibody or antigen binding fragment thereof with a bivalent linker reagent to form Ab-Z-L as described herein above, followed by reaction with a drug moiety D; or (2) reaction of a reactive substituent of a drug moiety with a bivalent linker reagent to form D-L-Z', followed by reaction with a reactive substituent of an antibody or antigen binding fragment thereof as described herein above. Additional methods for preparing ADC are described herein.

In another aspect, the anti-CD137 antibody or antigen binding fragment thereof has one or more lysine residues that can be chemically modified to introduce one or more sulfhydryl groups. The ADC is then formed by conjugation through the sulfhydryl group's sulfur atom as described herein above. The reagents that can be used to modify lysine include, but are not limited to, N-succinimidyl S-acetylthioacetate (SATA) and 2-Iminothiolane hydrochloride (Traut's Reagent).

In another aspect, the anti-CD137 antibody or antigen binding fragment thereof can have one or more carbohydrate groups that can be chemically modified to have one or more sulfhydryl groups. The ADC is then formed by conjugation through the sulfhydryl group's sulfur atom as described herein above.

In yet another aspect, the anti-CD137 antibody can have one or more carbohydrate groups that can be oxidized to provide an aldehyde (—CHO) group (see, for e.g., Laguzza, et al., J. Med. Chem. 1989, 32(3), 548-55). The ADC is then formed by conjugation through the corresponding aldehyde as described herein above. Other protocols for the modification of proteins for the attachment or association of cytotoxins are described in Coligan et al., Current Protocols in Protein Science, vol. 2, John Wiley & Sons (2002), incorporated herein by reference.

Methods for the conjugation of linker-drug moieties to cell-targeted proteins such as antibodies, immunoglobulins or fragments thereof are found, for example, in U.S. Pat. Nos. 5,208,020; 6,441,163; WO2005037992; WO2005081711; and WO2006/034488, all of which are hereby expressly incorporated by reference in their entirety.

Routes of Administration and Dosing

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

ADCs described herein can be administered to a patient (e.g., a human patient suffering from an immune disease or cancer) in a variety of dosage forms. For instance, ADCs described herein can be administered to a patient suffering from an immune disease or cancer in the form of an aqueous solution, such as an aqueous solution containing one or more pharmaceutically acceptable excipients. Suitable pharmaceutically acceptable excipients for use with the compositions and methods described herein include viscosity-modifying agents. The aqueous solution may be sterilized using techniques known in the art.

Pharmaceutical formulations comprising anti-CD137 ADCs as described herein are prepared by mixing such ADC with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol;

alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

The amount of ADC administered should be sufficient to deplete cells, e.g., activated T cells, which reject autologous cell therapy, e.g., CAR cell therapy. The determination of a therapeutically effective dose is within the capability of practitioners in this art, however, as an example, in embodiments of the method described herein utilizing systemic administration of an ADC for the treatment of an immune disease or cancer, an effective human dose will be in the range of 0.1-150 mg/kg (e.g., 5 mg/kg, 10 mg/kg, 25 mg/kg, 50 mg/kg, 75 mg/kg, 100 mg/kg, 150 mg/kg etc.). The route of administration may affect the recommended dose. Repeated systemic doses are contemplated in order to maintain an effective level, e.g., to reduce the risk of CAR-T cell rejection, depending on the mode of administration adopted.

The anti-CD137 ADCs described herein may be administered by a variety of routes, such as orally, transdermally, subcutaneously, intranasally, intravenously, intramuscularly, intraocularly, or parenterally. The most suitable route for administration in any given case will depend on the particular ADC, the patient, pharmaceutical formulation methods, administration methods (e.g., administration time and administration route), the patient's age, body weight, sex, severity of the diseases being treated, the patient's diet, and the patient's excretion rate.

The effective dose of an anti-CD137 ADC described herein can range, for example from about 0.001 to about 100 mg/kg of body weight per single (e.g., bolus) administration, multiple administrations, or continuous administration, or to achieve an optimal serum concentration (e.g., a serum concentration of 0.0001-5000 g/mL) of the anti-CD137 ADC. A dose of the anti-CD137 ADC may be administered one or more times (e.g., 2-10 times) per day, week, or month to a human subject who has had, is concomitantly receiving, or will be receiving CAR therapy at a time point following delivery of the anti-CD137 ADC. An anti-CD137 ADC may be administered to the human patient one time or as multiple doses. In one embodiment, the anti-CD137 ADC can be administered in an amount sufficient to reduce the quantity of host-reactive T cells, for example, by 10%, 20%, 30%, 40%, 50%, 60%, 70%, 80%, 90%, 95%, or more prior to CAR therapy.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention. The data in Examples 1-3 was previously presented in International Patent Application No. WO2018/134787 (published Jul. 26, 2018), the entire contents of which are incorporated herein by reference.

Example 1. In Vitro Analysis of an Anti-CD137-Amanitin Antibody Drug Conjugate (ADC) Using an In Vitro T Cell Killing Assay Cryopreserved negatively-selected primary human T cells were thawed and stimulated with anti-CD3/anti-CD28 beads (Invitrogen) at a bead:cell ratio of 0.5:1. At the start of the assay, 2e4 T cells were seeded per well of a 384 well plate and ADCs were added to the wells at various concentrations between 0.003 nm and 30 nm before being placed in an incubator with 37° C. and 5% $CO_2$. Following 4 days of culture, cells were analyzed by flow cytometry. Cells were stained with a viability marker Live/Dead Yellow (Invitrogen) and run on a volumetric flow cytometer. Numbers of viable, activated cells (FIG. 1A) and viable, non-activated cells (FIG. 1B) were determined by FSC vs SSC. A non-specific human IgG conjugated to amanitin (hIgG-amanitin) served as a negative control. Thus control was compared to two different ADCs: 1) chimeric anti-CD137 antibody BBK2 conjugated to amanitin (CD137-Amanitin); and 2) an ADC including an antibody specific a T-cell antigen conjugated to Amanitin (anti-Tcell-Amanitin). The anti-Tcell-Amanitin ADC served as a positive control as it was expected to bind and kill both activated and non-activated T cells.

Figure 1B:
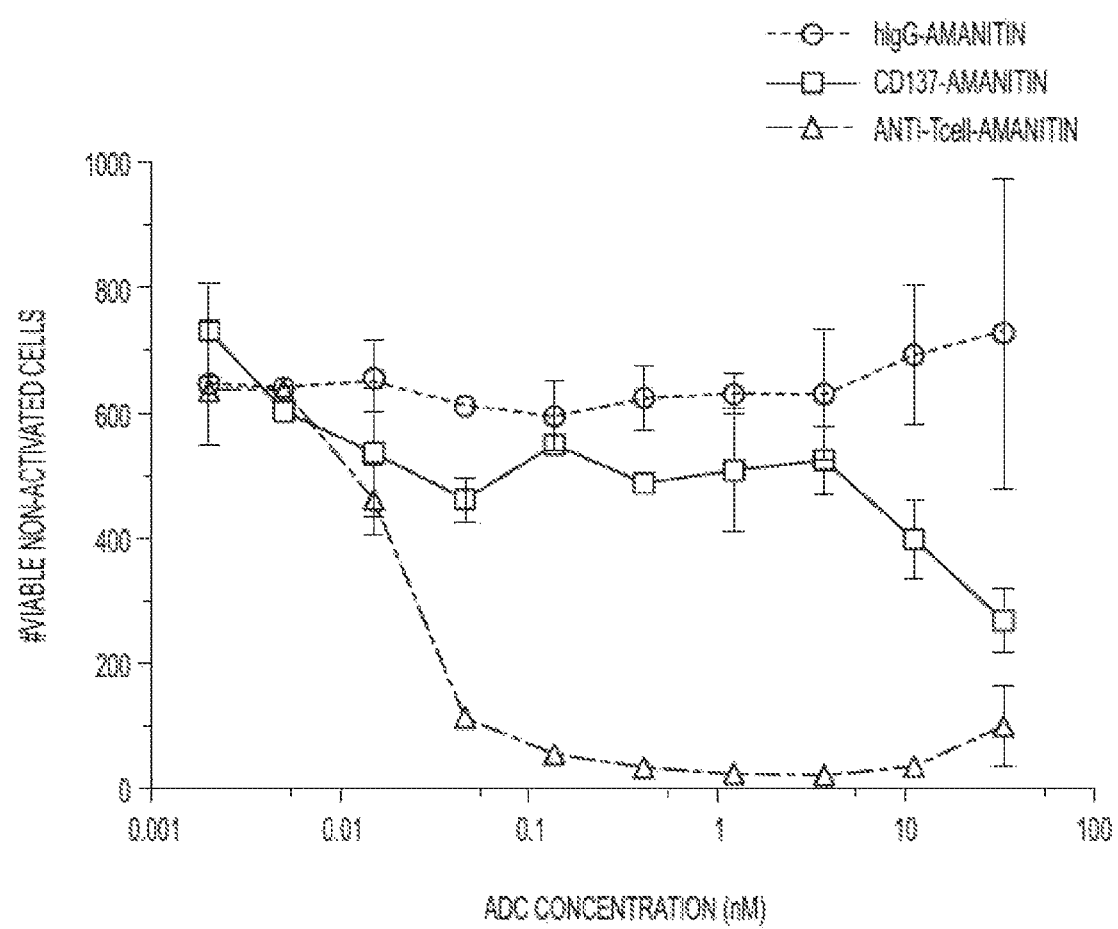

As shown in FIGS. 1A and 1B, the anti-CD137-amanitin ADC (i.e., "CD137-Amanitin) specifically killed activated T cells and did not appreciably kill non-activated (resting, steady-state) T cells. In addition, the positive control (i.e., the "anti-Tcell-Amanitin" ADC), which was an ADC that specifically targeted both activated and non-activated T cells, killed both activated and non-activated T cells.

Example 2. Analysis of the Prevention of GvHD Using a Xeno-GvHD Mouse Model

The ability of an anti-CD137-amanitin ADC to prevent the formation or occurrence of GvHD was assessed in vivo using a xeno-GvHD mouse model. Female, 6-8-week-old NSG mice were irradiated (200cGy) and transplanted the following day with $6 \times 10^6$ human peripheral blood mononuclear cells (PBMCs) to generate the GvHD mouse model. One day later, animals were dosed (at 3 mg/kg) with an anti-CD137-amanitin ADC (i.e., "CD137-Amanitin") or with various control reagents (i.e., buffer alone ("PBS"), an anti-CD137 antibody ("CD137 Naked"), or an amanitin-based ADC that is not specific to CD137 ("Isotype-Amanitin")). The anti-CD137 antibody used in this example in the ADCs and as a naked antibody was chimeric BBK2.

Animals were followed closely daily after dosing for signs of GvHD and/or decreased body conditions including, but not limited to, hunched posture, ruffled fur, weight loss, and/or limited activity. Animals with severe body condition concerns, or those animals that showed weight loss >20%, were sacrificed and their tissues were analyzed for human cells. Peripheral blood and spleens of mice were stained with a cocktail of antibodies, including hCD45, mCD45, hCD3, and hCD137 antibodies, red blood cell were lysed, and analyzed by flow cytometry. The number of human T cells in the blood were defined as hCD45+CD3+ and normalized to input blood volume. The percent survival as a function of days post-treatment is provided in FIG. 2. The number of human T cells in the peripheral blood as a function of days post-transplant is provided in FIG. 3.

Figure 2:
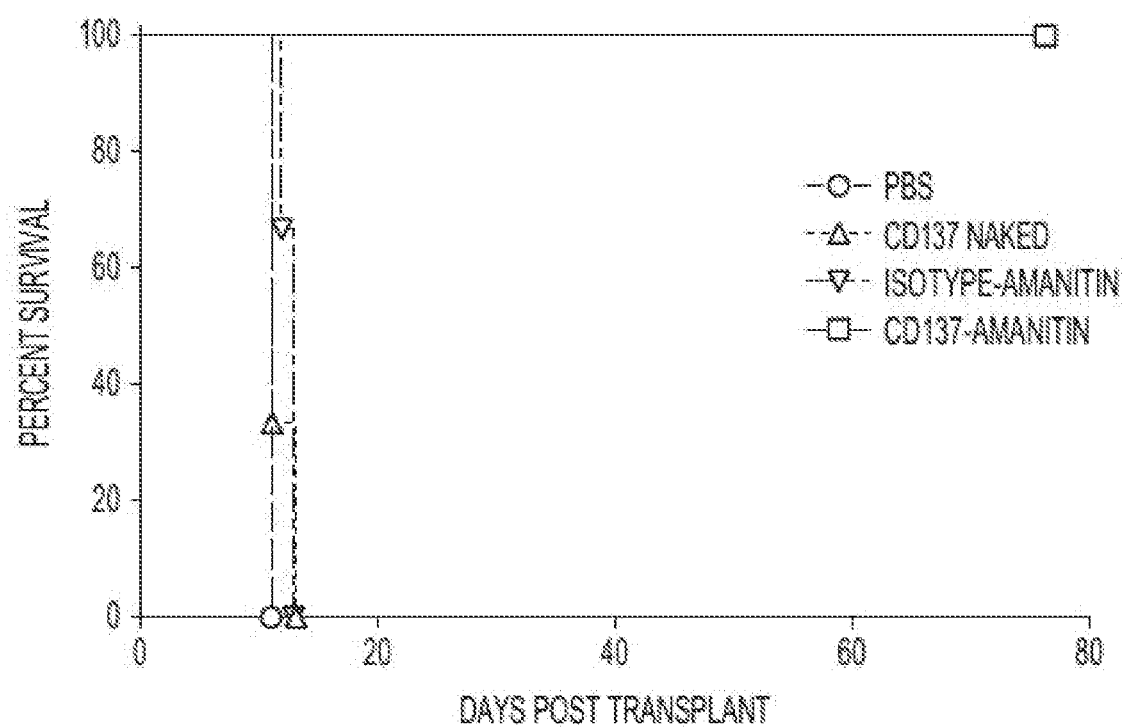
FIG. 2 graphically depicts the results of an in vivo assay comparing the percent survival of mice (y-axis) as a function of days post-transplant (x-axis) for an anti-CD137-amanitin ADC in comparison to controls PBS, an anti-CD137 antibody (naked), and isotype-amanitin in a NSG mouse xeno-GvHD model.
Figure 3:
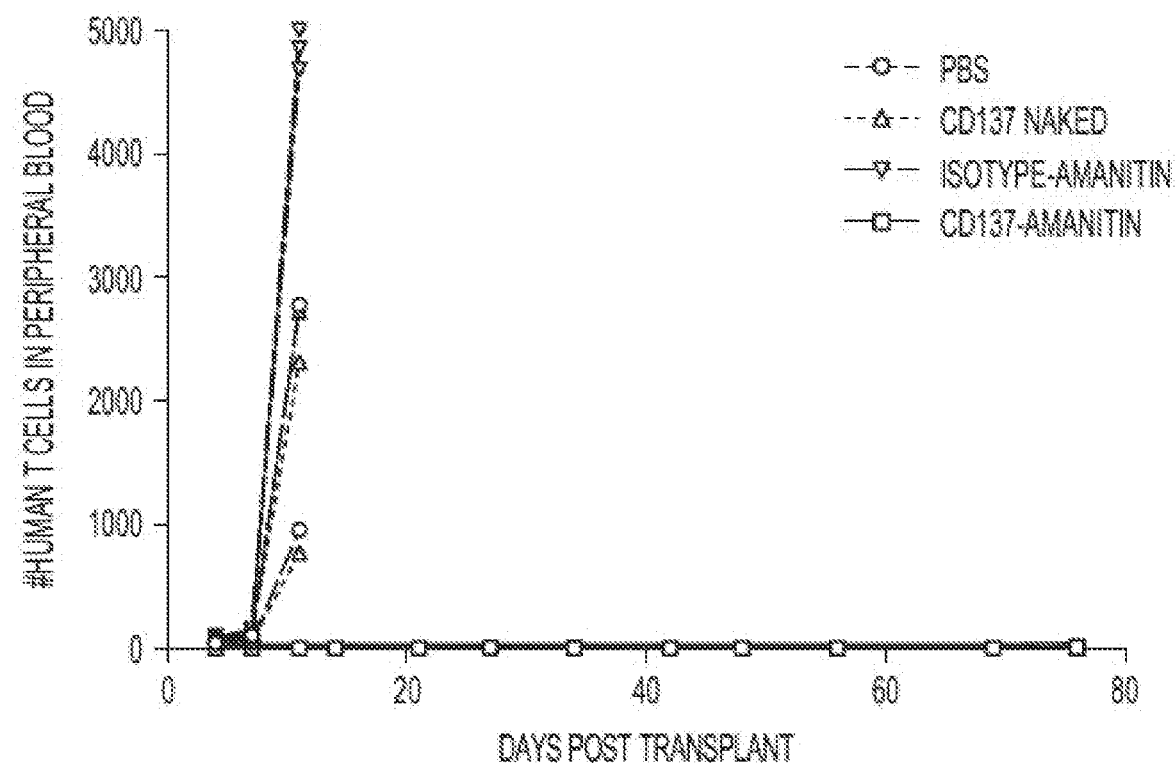
FIG. 3 graphically depicts the results of an in vivo assay comparing the number of human T cells detected in the peripheral blood (y-axis) as a function of days post-transplant (x-axis) for an anti-CD137-amanitin ADC in comparison to controls PBS, an anti-CD137 antibody (naked), and isotype-amanitin in a NSG mouse xeno-GvHD model.

As demonstrated in FIG. 2, the animals treated with a single dose of the anti-CD137-amanitin ADC ("CD137-Amanitin") showed essentially complete prevention of GvHD, even at 80 days post-transplant, while the animals treated with a control (i.e., PBS, an anti-CD137 antibody (naked), and isotype-amanitin) all died within 11 to 13 days post-transplant. These results also indicate that the anti-CD137-amanitin ADC was well-tolerated in all animals and that a single dose of the anti-CD137-amanitin ADC was sufficient to completely prevent GvHD (as opposed to requiring multiple doses). As demonstrated in FIG. 3, no human T cells were detectable in the peripheral blood of mice over a period of at least 70 days after the transplant in anti-CD137-amanitin treated mice, while animals treated with a control were characterized as having human T cells detectable in the peripheral blood of mice several days post-transplant, indicating the development of GvHD in the animals treated with a control.

Figure 4A:
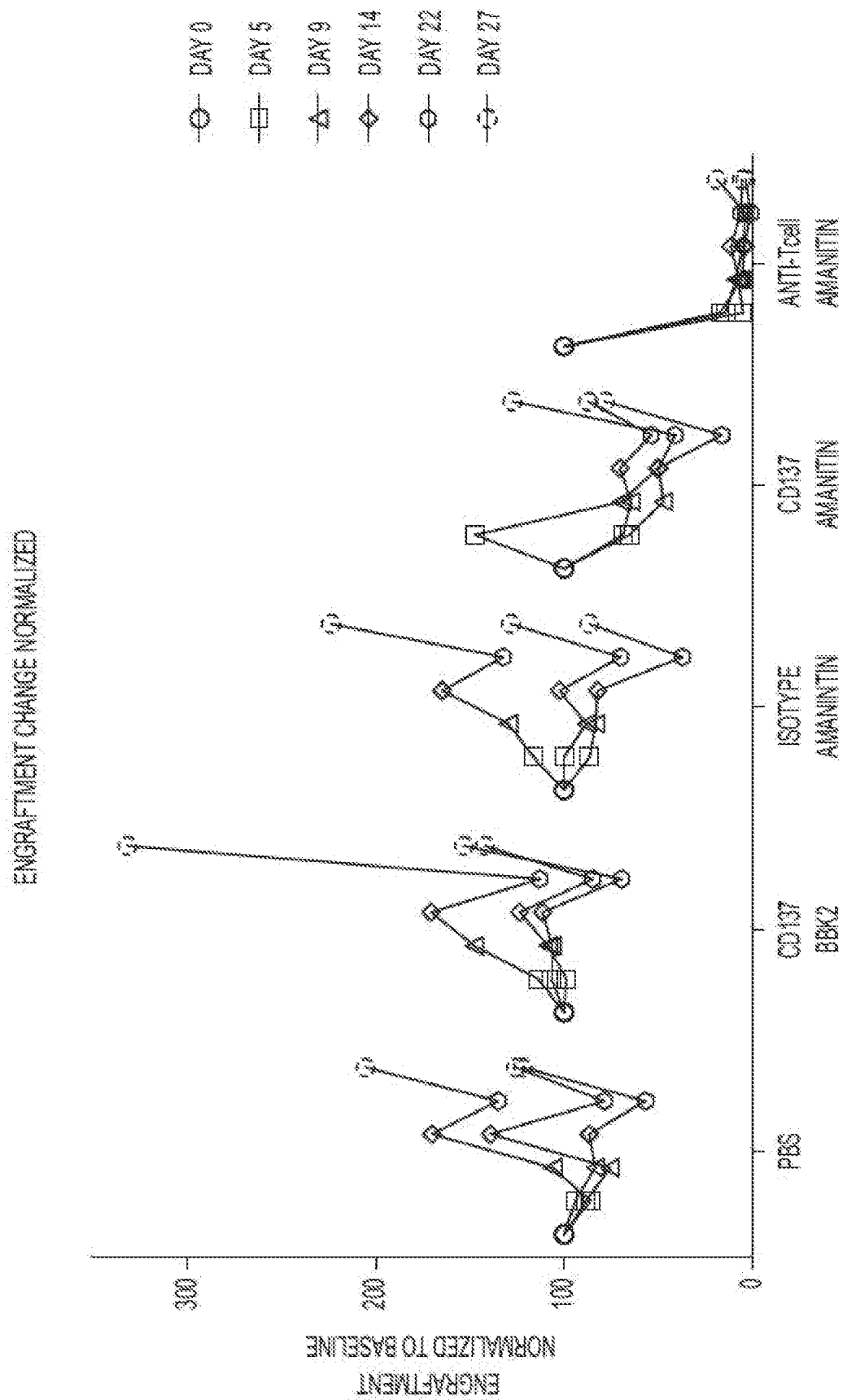
FIGS. 4A and 4B graphically depict the results of in vivo assays for determining engraftment rates (FIG. 4A) and T cell frequency (FIG. 4B) in a humanized NSG-SGM3 mouse model where engraftment and T cell frequency were measured at day 5, day 9, day 14, day 22 and at day 27 post-transplant for an anti-CD137-amanitin ADC in comparison to controls PBS, an anti-CD137-BBK antibody (naked), an isotype-amanitin, and an anti-Tcell-Amanitin ADC in a NSG mouse xeno-GvHD model.
Figure 4B:
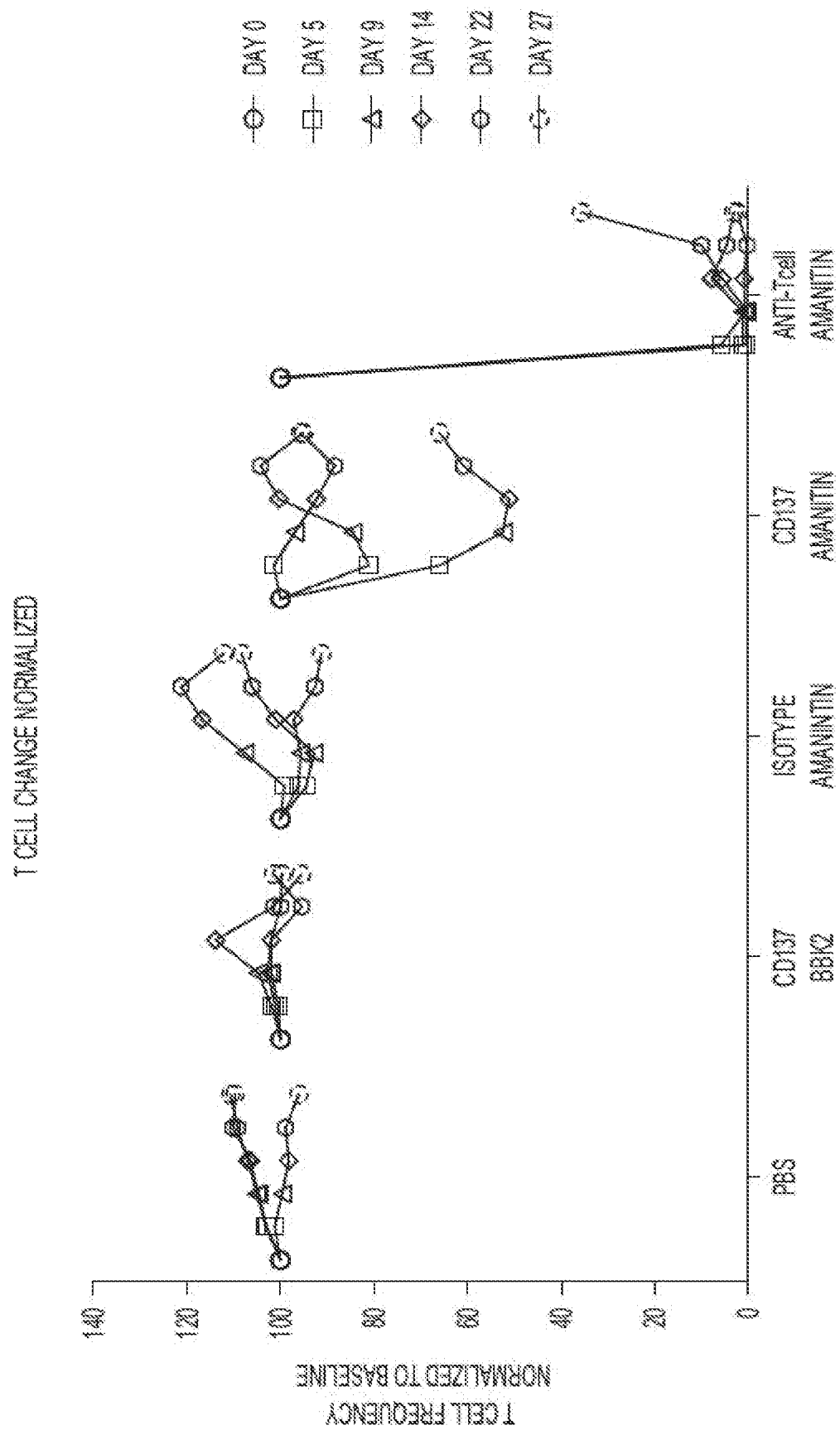

Example 3. Determination of Engraftment Rates and Steady-State T Cell Depletion in a hNSG-SGM3 Mouse Model Female, humanized NSG-SGM3 mice were evaluated for baseline human hematopoietic (overall and T-cell) engraftment rates in the peripheral blood by flow cytometry using hCD45, mCD45, hCD3, and hCD137 antibodies. Mice were randomized and then treated with CD137-Amanitin ADC (chimeric BBK2-Amanitin ADC), Isotype-Amanitin ADC, or an anti-T cell Amanitin ADC, each at a dose of 3 mg/kg. Engraftment and T cell depletion in the periphery of the mice was measured at day 5, day 9, day 14, day 22 and day 27 post treatment (FIGS. 4A and 4B). Peripheral blood was stained to evaluate changes in chimerism and T cell numbers. Equivalent amounts of blood were run on a volumetric flow cytometer and absolute counts were determined based on event numbers. Decreases in engraftment and T cell numbers was normalized to baseline values.

The results in FIGS. 4A and 4B indicate that the anti-CD137-amanitin ADC was well-tolerated in this mouse model. Further, engraftment and T cell frequency (after normalizing to baseline) remained near baseline levels, with a moderate to transient decrease in engraftment and T cell frequency for the anti-CD137-amanitin ADC treated mice. These data indicate that there is generally a lack of T cell depletion in steady-state humanized NSG mice, which indicates that the immune function can be preserved in anti-CD137-amanitin ADC treated mice because most of the T cells are not depleted. To the contrary, mice treated with an ADC that specifically targets an alternate T cell marker ("anti-Tcell-Amanitin") demonstrated complete ablation of engraftment and T cell numbers.

The heavy and light chain amino acid sequences of chimeric BBK2 described in the above examples are set forth in SEQ ID NOs: 11 and 12, respectively.

Example 4: Administration of Allogeneic CAR-T Cells in a Mouse Model

The following study is performed to assess the level of CAR-T cells present in an allogeneic recipient under different conditions.

A murine allogeneic CAR-T model is used for this study. One suitable model is described in Ghosh et al., *Nature Medicine* (2017), 23(2):242-249.

A first treatment group of mice is treated with a priming dose of allogeneic T cells, by administration of $1\times10^7$ to $1\times10^9$ cells/kg by intravenous infusion at Day 0. On Day 3, the mice are administered an anti-CD137-α-amanitin ADC at a dose of 3 mg/kg. On Day 10, after the ADC has substantially cleared from the blood of the mice, mice are administered allogeneic CAR-T cells. The CAR-T cells are from the same donor as the allogeneic T cells administered on Day 0.

A second treatment group of mice is treated using the same protocol as the first treatment group, but is administered an unconjugated anti-CD137 antibody on Day 3, in place of the anti-CD137 ADC.

A third treatment group of mice is treated using the same protocol as the first treatment group, but is administered an isotype control antibody conjugated to α-amanitin on Day 3, in place of the anti-CD137 ADC.

A fourth treatment group of mice is treated using the same protocol as the first treatment group, but is administered a priming dose of autologous T cells at Day 0, in place of the allogeneic T cells.

A fifth treatment group of mice is administered allogeneic CAR-T cells at Day 10, without prior treatment.

A sixth treatment group of mice is administered autologous CAR-T cells at Day 10, without prior treatment.

The number of CAR-T cells present in spleen and peripheral blood of mice from each treatment group is determined at Day 14, Day 17, and Day 30. The number of CD137+ activated T cells in the spleen and peripheral blood of mice from each treatment group is determined at Day 9. Mice are monitored for symptoms of GVHD and the presence of CAR-T cells throughout the study.

Example 5: Administration of an Anti-CD137 Antibody Drug Conjugate to a Human Patient to Prevent Rejection of an Allogeneic Cell Therapy A human patient is selected to receive an allogeneic cell therapy, such as an allogeneic CAR cell therapy. To inhibit or prevent the rejection of the allogeneic cells, an anti-CD137 antibody drug conjugate (ADC) is administered in accordance with the methods disclosed herein. The physician carries out the following treatment steps.

First, an initial amount of an allogeneic cell is intravenously administered to the patient in an amount sufficient to elicit a priming immune response to the allogeneic cell. In the priming step, allogeneic cells are administered to the patient to elicit an immune response resulting in endogenous activated CD137+ T cells.

Subsequently, the patient is administered an anti-CD137 ADC comprising an anti-CD137 antibody conjugated to a cytotoxin via a linker. The anti-CD137 ADC is administered in an amount effective to deplete endogenous CD137+ activated T cells. The level of CD137+ activated T cells is assessed in the patient following administration of the anti-CD137 ADC to confirm depletion.

Next, the patient is administered a therapeutically effective amount of allogeneic cells expressing a CAR. The allogeneic cells are derived from the same donor as the cells administered to the patient during the priming step. Acceptance of the allogeneic cells in the recipient patient is promoted and the risk of host versus graft (HvG) reactions is reduced, relative to patients receiving an allogeneic cell therapy without priming and administration of an anti-CD137 ADC.

TABLE 4

Sequence Summary

| Sequence Identifier | Description | Sequence |
|---|---|---|
| SEQ ID NO: 1 | Human CD137 | MGNSCYNIVATLLLVLNFERTRSLQDPCSNCP AGTFCDNNRNQICSPCPPNSFSSAGGQRTCDIC RQCKGVFRTRKECSSTSNAECDCTPGFHCLGA GCSMCEQDCKQGQELTKKGCKDCCFGTEND QKRGICRPWTNCSLDGKSVLVNGTKERDVVC GPSPADLSPGASSVTPPAPAREPGHSPQIISFFL ALTSTALLFLLFELTLRFSVVKRGRKKLLYIFK QPFMRPVQTTQEEDGCSCRFPEEEEGGCEL |
| SEQ ID NO: 2 | CD8 hinge | AKPTTTPAPRPPTPAPTIASQPLSLRPEACRPAA GGAVHTRGLDFA |
| SEQ ID NO: 3 | Hybrid CD8 - CD28 hinge | AKPTTTPAPRPPTPAPTIASQPLSLRPEACRPAA GGAVHTRGLDFAPRKIEVMYPPPYLDNEKSN GTIIHVKGKHLCPSPLFPGPSKP |
| SEQ ID NO: 4 | CD3 transmembrane domain | LDPKLCYLLDGILFIYGVILTALFLRVK |
| SEQ ID NO: 5 | CD3 transmembrane domain | LCYLLDGILFIYGVILTALFL |
| SEQ ID NO: 6 | CD28 transmembrane domain | FWVLVVVGGVLACYSLLVTVAFIIFWV |
| SEQ ID NO: 7 | CD28 transmembrane domain (fragment) | IEVMYPPPYLDNEKSNGTIIHVKGKHLCPSPLF PGPSKPFWVLVVVGGVLACYSLLVTVAFIIFW V |
| SEQ ID NO: 8 | CD3 zeta signaling region | RVKFSRSADAPAYQQGQNQLYNELNLGRREE YDVLDKRRGRDPEMGGKPRRKNPQEGLYNEL QKDKMAEAYSEIGMKGERRRGKGHDGLYQG LSTATKDTYDALHMQALPPR |
| SEQ ID NO: 9 | 4-1BB (CD137) co-stimulatory signaling region | KRGRKKLLYIFKQPFMRPVQTTQEEDGCSCRF PEEEEGGCEL |
| SEQ ID NO: 10 | CD28 co-stimulatory signaling region, | RSKRSRLLHSDYMNMTPRRPGPTRKHYQPYA PPRDFAAYRS |
| SEQ ID NO: 11 | BBK2 heavy chain (variable region underlined) | QVQLQQPGAELVRPGASVKLSCKASGYTFTS YWINWVKQRPGQGLEWIGNIYPSDSYTNYNQ KFKDKATLTVDKSSNTVYMQLNSPTSEDSAV YYCTRNGVEGYPHYYAMEYWGQGTSVTVSS ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPELLGGPSVFLFPPK PKDTLMISRTPEVTCVVVDVSHEDPEVKFNW YVDGVEVHNAKTKPREEQYNSTYRVVSVLTV LHQDWLNGKEYKCKVSNKALPAPIEKTISKA KGQPREPQVYTLPPSRDELTKNQVSLTCLVKG FYPSDIAVEWESNGQPENNYKTTPPVLDSDGS FFLYSKLTVDKSRWQQGNVFSCSVMHEALHN HYTQKSLSLSPGK |
| SEQ ID NO: 12 | BBK2 light chain (variable region underlined) | DIQMTQTTSALSASLGDRVTIGCRASQDLSNH LYWYQQKPDGTVKLLIYYTSRLHSGVPSRESG SGSGTDYSLTIRNLEQEDVATYFCQQGYTLPY TFGGGTKLEIKRTVAAPSVFIFPPSDEQLKSGT ASVVCLLNNFYPREAKVQWKVDNALQSGNS QESVTEQDSKDSTYSLSSTLTLSKADYEKHKV YACEVTHQGLSSPVTKSFNRGEC |
| SEQ ID NO: 13 | VH CDR1 of BBK2 (as defined in Lee et al.) | SGYTFTSYW |

TABLE 4-continued

Sequence Summary

| Sequence Identifier | Description | Sequence |
|---|---|---|
| SEQ ID NO: 14 | VH CDR2 of BBK2 (as defined in Lee et al.) | NIYPSDSYT |
| SEQ ID NO: 15 | VH CDR3 of BBK2 (as defined in Lee et al.) | TRNGVEGYPHYYAME |
| SEQ ID NO: 16 | VL CDR1 of BBK2 (as defined in Lee et al.) | SQDLSNH |
| SEQ ID NO: 17 | VL CDR2 of BBK2 (as defined in Lee et al.) | YYTS |
| SEQ ID NO: 18 | VL CDR3 of BBK2 (as defined in Lee et al.) | CQQGYTLPY |
| SEQ ID NO: 19 | VH CDR1 of BBK2 (Kabat) | SYWIN |
| SEQ ID NO: 20 | VH CDR2 of BBK2 (Kabat) | NIYPSDSYTNYNQKFKD |
| SEQ ID NO: 21 | VH CDR3 of BBK2 (Kabat) | NGVEGYPHYYAMEY |
| SEQ ID NO: 22 | BBK2 Heavy Chain Variable Region | QVQLQQPGAELVRPGASVKLSCKASGYTFTS YWINWVKQRPGQGLEWIGNIYPSDSYTNYNQ KFKDKATLTVDKSSNTVYMQLNSPTSEDSAV YYCTRNGVEGYPHYYAMEYWGQGTSVTVSS |
| SEQ ID NO: 23 | VL CDR1 of BBK2 (Kabat) | RASQDLSNHLY |
| SEQ ID NO: 24 | VL CDR2 of BBK2 (Kabat) | YTSRLHS |
| SEQ ID NO: 25 | VL CDR3 of BBK2 (Kabat) | QQGYTLPYT |
| SEQ ID NO: 26 | BBK2 Light Chain Variable Region | DIQMTQTTSALSASLGDRVTIGCRASQDLSNH LYWYQQKPDGTVKLLIYYTSRLHSGVPSRFSG SGSGTDYSLTIRNLEQEDVATYFCQQGYTLPY TFGGGTKLEIK |
| SEQ ID NO: 27 | Linker | AGGGGS |
| SEQ ID NO: 28 | Linker | GGGGSGGGGSGGGGS |

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. A method for treating or reducing rai versus host disease of allogeneic cells transplanted into a human subject, the method comprising
   (a) administering to the human subject a first amount of an allogeneic cell, wherein
   the first amount is sufficient to elicit a priming response to the allogeneic cell in the human subject;
   (b) administering an anti-CD 137 antibody drug conjugate (ADC) to the human subject such that endogenous CD137+ activated T cells are depleted, wherein the anti-CD137 ADC comprises an anti-CD137 antibody, or antigen-binding fragment thereof, conjugated to a cytotoxin via a linker; and
   (c) administering a therapeutically effective amount of an allogeneic cell expressing a CAR to the human subject, wherein the allogeneic cell is the same type of allogeneic cell administered in (a), and wherein the CAR comprises an extracellular domain that binds to a tumor antigen, a transmembrane domain, and a cytoplasmic signaling domain;
   wherein the cytotoxin is an RNA polymerase inhibitor, and
   wherein the RNA polymerase inhibitor is an amanitin selected from the group consisting of α-amanitin, β-amanitin, γ-amanitin, ε-amanitin, amanin, amaninamide, amanullin, amanullinic acid, and proamanullin.

2. The method of claim 1, the method comprising administering the first amount of the allogeneic cell to the human subject between about 48 hours to about 7 days before step (b).

3. The method of claim 1, the method comprising administering the therapeutically effective amount of the allogeneic cell expressing the CAR to the human subject between about 24 hours to about 14 days after step (b).

4. A method of treating or reducing graft versus host disease of allogeneic cells transplanted into a human subject, the method comprising
   (a) administering an anti-CD137 ADC to the human subject, wherein the anti-CD137 ADC comprises an anti-CD137 antibody, or antigen-binding fragment thereof, conjugated to a cytotoxin via a linker, and wherein the human subject is characterized as having activated T cells directed to an allogeneic cell that was previously administered to the human subject; and
   (b) administering a therapeutically effective amount of an allogeneic cell expressing a CAR to the human subject, wherein the allogeneic cell is the same type of allogeneic cell described in (a), and wherein the CAR comprises an extracellular domain that binds to a tumor antigen, a transmembrane domain, and a cytoplasmic signaling domain,
   wherein the cytotoxin is an RNA polymerase inhibitor, and
   wherein the RNA polymerase inhibitor is an amanitin selected from the group consisting of α-amanitin, β-amanitin, γ-amanitin, ε-amanitin, amanin, amaninamide, amanullin, amanullinic acid, and proamanullin.

5. The method of claim 4, the method comprising administering the effective amount of the allogeneic cell expressing the CAR to the human subject between about 24 hours to about 14 days after step (a).

6. The method of claim 1, wherein the allogeneic cell is an allogeneic T cell or an allogeneic NK cell.

7. The method of claim 1, wherein the effective amount of the allogeneic cell expressing the CAR is about $2\times10^6$ to about $3.0\times10^8$ cells/kg.

8. The method of claim 1, wherein the human subject has cancer or an autoimmune disease.

9. The method of claim 1, wherein the anti-CD137 antibody, or antigen-binding fragment thereof, comprises a heavy chain variable region comprising a CDR1, a CDR2, and a CDR3 having an amino acid sequence as set forth in SEQ ID NOs: 19, 20, and 21, respectively, and comprises a light chain variable region comprising a CDR1, a CDR2, and a CDR3 having an amino acid sequence as set forth in SEQ ID NOs: 23, 24, and 25, respectively.

10. The method of claim 9, wherein the anti-CD137 antibody, or antigen-binding fragment thereof, is chimeric or humanized.

11. The method of claim 1, wherein the anti-CD137 antibody, or antigen-binding fragment thereof, is an IgG1 isotype or an IgG4 isotype.

12. The method of claim 1, wherein the linker of the ADC is N-beta-maleimidopropionyl-Val-Ala-para-aminobenzyl (BMP-Val-Ala-PAB).

13. The method of claim 1, wherein the ADC is represented by the following structures:

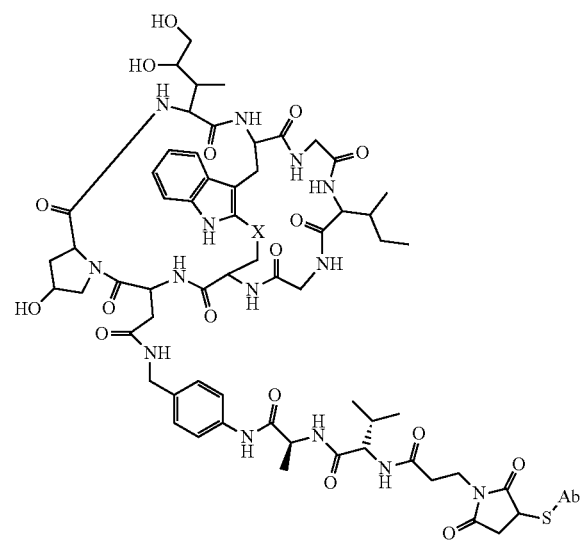

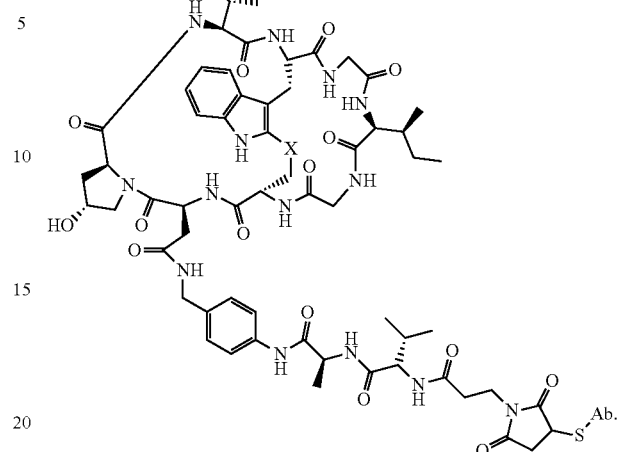

14. The method of claim 1, wherein the ADC is represented by:

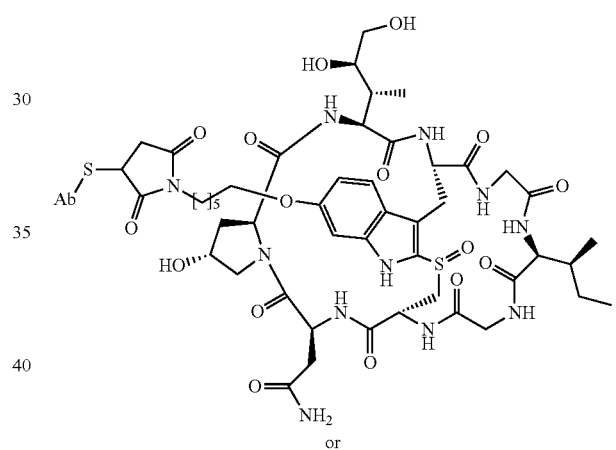

or

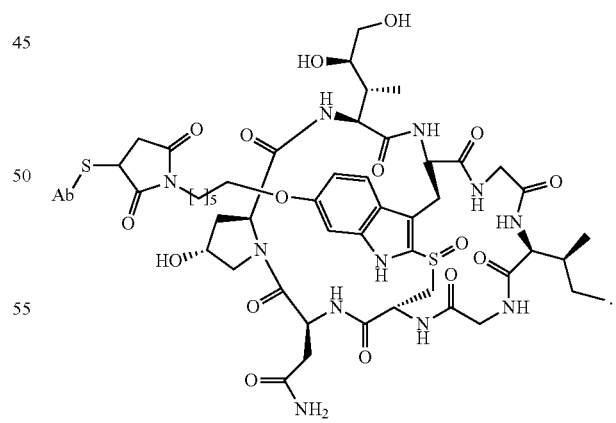

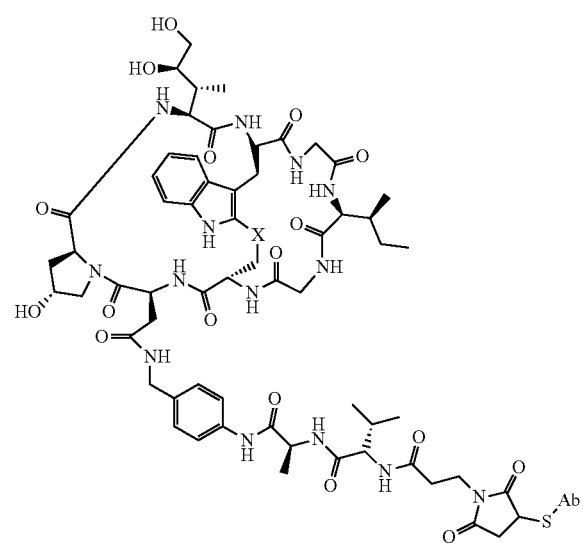

15. The method of claim 1, wherein the ADC has a serum half-life of 3 days or less.

16. The method of claim 1, wherein the extracellular domain comprises an scFv antibody or a single chain T cell receptor (scTCR).

17. The method of claim 1, wherein the extracellular domain comprises a non-immunoglobulin scaffold protein.

18. The method of claim 1, wherein the extracellular domain of the CAR binds to a tumor antigen selected from the group consisting of CD19, CD22, CD3, CD7, BCMA, CD137, CD20, AFP, GPC3, MUC1, mesothelin, CD38, PD1, EGFR, MG7, TACI, CEA, PSCA, CEA, HER2, CD33, ROR2, NKR-2, PSCA, CD28, TAA, NKG2D, or CD123.

19. The method of claim 1, wherein the cytoplasmic signaling domain of the CAR comprises a CD28 cytoplasmic signaling domain, a CD3 zeta cytoplasmic signaling domain, an OX40 cytoplasmic signaling domain, and/or a CD137 cytoplasmic signaling domain.

20. The method of claim 1, wherein the cytoplasmic signaling domain of the CAR comprises a CD3 zeta cytoplasmic signaling domain.

21. The method of claim 8, wherein the cancer is leukemia, adult advanced cancer, pancreatic cancer, non-resectable pancreatic cancer, colorectal cancer, metastatic colorectal cancer, ovarian cancer, triple-negative breast cancer, hematopoietic/lymphoid cancer, colon cancer liver metastasis, small cell lung cancer, non-small cell lung cancer, B-cell lymphoma, relapsed or refractory B-cell lymphoma, follicular lymphoma, mantle cell lymphoma, diffuse large cell lymphoma, relapsed or refractory diffuse large cell lymphoma, anaplastic large cell lymphoma, primary mediastinal B-cell lymphoma, recurrent mediastinal, refractory mediastinal large B-cell lymphoma, large B-cell lymphoma, Hodgkin lymphoma, non-Hodgkin lymphoma, relapsed or refractory non-Hodgkin lymphoma, refractory aggressive non-Hodgkin lymphoma, B-cell non-Hodgkin lymphoma, refractory non-Hodgkin lymphoma, colorectal carcinoma, gastric carcinoma, pancreatic carcinoma, triple-negative invasive breast carcinoma, renal cell carcinoma, lung squamous cell carcinoma, hepatocellular carcinoma, urothelial carcinoma, leukemia, B-cell leukemia, B-cell acute lymphocytic leukemia, B-cell acute lymphoblastic leukemia, adult acute lymphoblastic leukemia, B-cell prolymphocytic leukemia, childhood acute lymphoblastic leukemia, refractory childhood acute lymphoblastic leukemia, acute leukemia, acute lymphoblastic leukemia, acute lymphocytic leukemia, prolymphocytic leukemia, chronic lymphocytic leukemia, acute myeloid leukemia, recurrent plasma cell myeloma, refractory plasma cell myeloma, multiple myeloma, relapsed or refractory multiple myeloma, multiple myeloma of bone, malignant glioma of brain, myelodysplastic syndrome, EGFR-positive colorectal cancer, glioblastoma multiforme, neoplasms, blastic plasmacytoid dendritic cell neoplasms, liver metastases, solid tumors, advanced solid tumors, mesothelin positive tumors, or hematological malignancies.

22. The method of claim 1, wherein the amanitin is selected from the group consisting of β-amanitin, γ-amanitin, ε-amanitin, amanin, amaninamide, amanullin, amanullinic acid, and proamanullin.

23. A method for transplanting allogeneic cells into a human subject, the method comprising
   (a) administering to the human subject a first amount of allogeneic cell effective to activate endogenous T cells directed to the allogeneic cell;
   (b) administering an anti-CD137 antibody drug conjugate (ADC) to the human subject such that a level of endogenous CD137+ activated T cells in a biological sample from the human subject is reduced by at least 5% relative to a level of endogenous CD137+ activated T cells in a biological sample of the same type from the human subject taken after step a) prior to administration of said anti-CD137 antibody drug conjugate (ADC), wherein the anti-CD137 ADC comprises an anti-CD137 antibody, or antigen-binding fragment thereof, conjugated to a cytotoxin via a linker; and
   (c) administering a therapeutically effective amount of an allogeneic cell expressing a CAR to the human subject, wherein the allogeneic cell is the same type of allogeneic cell administered in (a), and wherein the CAR comprises an extracellular domain that binds to a tumor antigen, a transmembrane domain, and a cytoplasmic signaling domain;
   wherein the cytotoxin is an RNA polymerase inhibitor, and
   wherein the RNA polymerase inhibitor is an amanitin selected from the group consisting of α-amanitin, β-amanitin, γ-amanitin, ε-amanitin, amanin, amaninamide, amanullin, amanullinic acid, and proamanullin.

* * * * *